US010266698B2

(12) United States Patent
Vargas Cano et al.

(10) Patent No.: US 10,266,698 B2
(45) Date of Patent: Apr. 23, 2019

(54) COLORANT COMPOUNDS DERIVED FROM GENIPIN OR GENIPIN CONTAINING MATERIALS

(71) Applicant: ECOFLORA S.A.S., Sabaneta, Antioquia (CO)

(72) Inventors: Esteban Vargas Cano, Itagui (CO); Luis Fernando Echeverri Lopez, Medellin (CO); Juan Fernando Gil Romero, Medellin (CO); Edwin Andrés Correa Garcés, Medellin (CO); Sandra Patricia Zapata Porras, Medellin (CO)

(73) Assignee: ECOFLORA S.A.S., Sabaneta (CO)

( * ) Notice: Subject to any disclaimer, the term of this patent is extended or adjusted under 35 U.S.C. 154(b) by 0 days.

(21) Appl. No.: 15/807,435

(22) Filed: Nov. 8, 2017

(65) Prior Publication Data

US 2018/0127587 A1 May 10, 2018

Related U.S. Application Data

(62) Division of application No. 15/166,391, filed on May 27, 2016, now Pat. No. 9,890,286, which is a division of application No. 14/285,325, filed on May 22, 2014, now Pat. No. 9,376,569.

(60) Provisional application No. 61/836,072, filed on Jun. 17, 2013, provisional application No. 61/826,391, filed on May 22, 2013.

(51) Int. Cl.

| | |
|---|---|
| ***A23L 5/43*** | (2016.01) |
| ***A61K 8/84*** | (2006.01) |
| ***A61K 47/34*** | (2017.01) |
| ***C09B 23/04*** | (2006.01) |
| ***C09B 61/00*** | (2006.01) |
| ***C09B 67/22*** | (2006.01) |
| ***C09B 67/54*** | (2006.01) |

(52) U.S. Cl.

CPC ................ *C09B 61/00* (2013.01); *A23L 5/43* (2016.08); *A61K 8/84* (2013.01); *A61K 47/34* (2013.01); *C09B 23/04* (2013.01); *C09B 67/0034* (2013.01); *C09B 67/0096* (2013.01); *A23V 2002/00* (2013.01); *A61K 2800/30* (2013.01)

(58) Field of Classification Search

CPC ..... C09B 61/00; C09B 23/04; C09B 67/0034; C09B 67/0096; A23L 5/43; A61K 8/84; A61K 47/34

USPC ....................................................... 514/772.7

See application file for complete search history.

(56) References Cited

U.S. PATENT DOCUMENTS

| | | | |
|---|---|---|---|
| 4,247,698 | A | 1/1981 | Toyama et al. |
| 4,347,356 | A | 8/1982 | Touyama et al. |
| 4,878,921 | A | 11/1989 | Koga et al. |
| 7,279,189 | B2 | 10/2007 | Lauro |
| 7,649,014 | B2 | 1/2010 | Zhang et al. |
| 7,927,637 | B2 | 4/2011 | Echeverry et al. |
| 9,376,569 | B2 | 6/2016 | Cano et al. |
| 2005/0008746 | A1 | 1/2005 | Beck et al. |
| 2008/0260668 | A1 | 10/2008 | Vidalenc |
| 2009/0223000 | A1 | 9/2009 | Ferreira |
| 2009/0246343 | A1 | 10/2009 | Wu et al. |
| 2010/0083448 | A1 | 4/2010 | Lopez et al. |
| 2012/0114772 | A1 | 5/2012 | Roesler et al. |
| 2013/0115252 | A1 | 5/2013 | Wu et al. |
| 2013/0202703 | A1 | 8/2013 | Sadano |
| 2013/0345427 | A1 | 12/2013 | Echeverry et al. |
| 2016/0376442 | A1 | 12/2016 | Cano et al. |

FOREIGN PATENT DOCUMENTS

| | | | |
|---|---|---|---|
| CN | 101104745 | | 1/2008 |
| CN | 101735642 | A | 6/2010 |
| CN | 101831469 | A | 9/2010 |
| CN | 101899484 | A | 12/2010 |
| CN | 102014670 | A | 4/2011 |
| CN | 102171292 | A | 8/2011 |
| CN | 102174608 | A | 9/2011 |
| CN | 102448327 | A | 5/2012 |
| CN | 104685004 | A | 6/2015 |
| JP | 52-053932 | | 4/1977 |
| JP | 52-053934 | | 4/1977 |
| JP | 55-164625 | | 12/1980 |
| JP | 57-81466 | | 5/1982 |
| JP | 57-209958 | | 12/1982 |
| JP | 61-47167 | | 3/1986 |
| JP | 64-22820 | | 1/1989 |
| JP | 5-339134 | | 12/1993 |
| JP | 7-310023 | | 11/1995 |
| JP | 8-301739 | | 11/1996 |
| WO | WO 2009/120579 | A1 | 10/2009 |
| WO | WO 2012/043173 | A1 | 4/2012 |
| WO | WO 2014/001910 | A1 | 1/2014 |
| WO | WO 2014/188275 | A2 | 11/2014 |

OTHER PUBLICATIONS

Wen; J. Food Sci. 2002, 67, 155-161. (Year: 2002).*

Djerassi, C., et al., "Naturally Occurring Oxygen Heterocyclics. IX. Isolation and Characterization of Genipin," *Journal of Organic Chemistry* 25:2174-2177, American Chemical Society, United States (1960).

(Continued)

*Primary Examiner* — Daniel R Carcanague

(74) *Attorney, Agent, or Firm* — Sterne, Kessler, Goldstein & Fox P.L.L.C.

(57) ABSTRACT

The present disclosure provides colorant compounds and methods of isolation of the colorant compounds derived from a reaction of genipin and an amine. The colorant compositions comprise purified compounds (e.g., a purified polymer or a purified dimer) obtained from multiple fractioning by chromatography of the reaction resulting material. The purified polymer or dimer can be used as a colorant by itself or in combination with another colorant for imparting color to a food, a drug, a cosmetic, a medical device, and textile products.

24 Claims, 38 Drawing Sheets

(56) References Cited

OTHER PUBLICATIONS

Fujikawa, S., et al., "Structure of Genipocyanin $G_1$, A Spontaneous Reaction Product Between Genipin and Glycine," *Tetrahedron Letters* 28(40):4699-4700, Pergamon Journals Ltd., United Kingdom (1987).
Fujikawa, S., et al., "Brilliant Skyblue Pigment Formation from Gardenia Fruits," *J. Ferment. Technol.* 65(4):419-424, Elsevier Science B.V., Netherlands (1987).
Jnouye, H. et al., "Structure of Blue Pseudoazulene-Skeleton Pigment derived from Genipin and Amino acids," 26th Symposium on the Chemistry of Natural Product, Kyoto, pp. 577-584, (Abstract) 1983.
Moritome, N., et al., "Properties of red pigments prepared from geniposidic acid and amino acids," *J Sci Food Agric* 79:810-814, Society of Chemical Industry, London (1999).
Muller, J., "Analytical Characterization of a Lyophilized Juice Sample of *Genipa americana* and a Blue Colorant Based on the Juice," AnalytiCon Discovery, Nov. 14, 2010, 28 pages.
Pino, Chala. "Handmade extraction of coloring natural, an alternative of use of the biological diversity of Choco, Columbia" *Acta Biologica Colombiana* 8(2):95-98, (2003) Abstract.
Touyama, R., et al., "Studies on the Blue Pigments Produced from Genipin and Methylamine. I. Structures of the Brownish-Red Pigments, Intermediates Leading to the Blue Pigments," *Chem. Pharm. Bull.* 42(3):668-673, Pharmaceutical Society of Japan, Japan (1994).
International Search Report for International Application PCT/IB2013/001854, European Patent Office, Netherlands, dated Oct. 24, 2013.
STN Database Registry Record: CAS Registry No. 1313734-13-2, entered STN Jul. 26, 2011.
STN Database Registry Record: CAS Registry No. 1313734-14-3, entered STN Jul. 26, 2011.
International Search Report for International Patent Application No. PCT/IB2014/001735, European Patent Office, Rijswijk, Netherlands, dated Jan. 7, 2015.
Office Action dated Oct. 1, 2014, from U.S. Appl. No. 13/532,757, inventors, Echeverry, L.F., et al., filed Jun. 25, 2012.
STN Database Registry Record: CAS Registry No. 1314879-21-4, entered STN Aug. 4, 2011.
Office Action dated Apr. 30, 2015, from U.S. Appl. No. 13/532,757, inventors, Echeverry, L.F., et al., filed Jun. 25, 2012.
Paik, Y.-S., et al., "Physical Stability of the Blue Pigments Formed from Geniposide of Gardenia Fruits: Effects of pH, Temperature, and Light," *J. Agric. Food Chem* 49:430-432, American Chemical Society, United States (2001).
Park, J.-E., et al., "Separation and Characterization of Water Soluble Blue Pigments Formed from Geniposide of Gardenia Fruits," *Agric. Chem. Biotechnol.* 44(4):190-193, Korean Society of Agricultural Chemistry and Biotechnology, Korea (2001).
Yang, Z., et al., "Isolation and Purification of Gardenia Blue Pigment with Ultra Filtration," *Modern Food Science Technology* 24:352-356, Gai Kan Bianjibn, China (2008).
Elkins, E., et al., "Characterization of Commercially Produced Pineapple Juice Concentrate," *J. Food Compos. Anal.*, 10(4): 285-298 (1997).
Fontana, A. J., et al., "Kinetics of Deterioration of Pineapple Concentrate," *J. Food Sci.*, 58(6): 1411-1417 (1993).
Hodgson, A. S., et al., "Pineapple Juice," *Fruit Juice Processing Technology*, pp. 378-435, Agscience, Inc., Aburundale, Florida (1993).

* cited by examiner

D11-0299-1_AD101542-02 (RIPAC_000_0632_2H2)
linear mode (m/z 2.000-10.000)

FIGs. 13A-D

Calibration curve 1

F(x)= 3859.3x – 17442.2 $R^2$=0.9996

Calibration Curve

ID# : 1
Name : polymer
Quantitative Method : External Standard
Function : f(x)=3859.3*x-17442.2
Rr1=0.9998319 Rr2=0.9996639
MeanRF:3461.25 RFSD:274.747 RFRSD:7.9378
FitType : Linear
ZeroThrough : Not Through
Weighted Regression : None
Detector Name : PDA

| # | Conc. (Ratio) | MeanArea | Area | Area%RSD |
|---|---|---|---|---|
| 1 | 20.000 | 59829.8 | 55371 | 6.485234 |
| | | | 61683 | |
| | | | 62436 | |
| 2 | 40.000 | 136139.1 | 133449 | 2.166034 |
| | | | 135676 | |
| | | | 139292 | |
| 3 | 60.000 | 216762.2 | 214550 | 0.896955 |
| | | | 218199 | |
| | | | 217538 | |
| 4 | 80.000 | 288039.0 | 285794 | 0.689672 |
| | | | 289569 | |
| | | | 288755 | |
| 5 | 100.000 | 369810.3 | 370080 | 0.067876 |
| | | | 369767 | |
| | | | 369584 | |

Calibration curve 2

$F(x) = 3061.54x - 25237.4$ $R^2=0.9900$

Calibration Curve

ID# : 1
Name : polymer
Quantitative Method : External Standard
Function : f(x)=3061.54*x-25237.4
Rr1=0.9950339 Rr2=0.9900925
MeanRF:2539.27 RFSD:256.801 RFRSD:10.1132
FitType : Linear
ZeroThrough : Not Through
Weighted Regression : None
Detector Name : PDA

| # | Conc. (Ratio) | MeanArea | Area | Area%RSD |
|---|---|---|---|---|
| 1 | 20.000 | 47612.3 | 50823 | 6.870823 |
| | | | 47730 | |
| | | | 44283 | |
| 2 | 40.000 | 88938.0 | 87849 | 1.100045 |
| | | | 89742 | |
| | | | 89223 | |
| 3 | 60.000 | 148535.3 | 148612 | 0.059414 |
| | | | 148555 | |
| | | | 148439 | |
| 4 | 80.000 | 217910.2 | 219994 | 1.260417 |
| | | | 218939 | |
| | | | 214798 | |
| 5 | 100.000 | 289280.6 | 286539 | 1.113932 |
| | | | 288472 | |
| | | | 292830 | |

Calibration curve 3

$F(x)= 3549.64x - 47048.3$ $R^2=0.9931$

Calibration Curve

ID# : 1
Name : polymer
Quantitative Method : External Standard
Function : f(x)=3549.64*x-47048.3
Rr1=0.9965751 Rr2=0.9931619
MeanRF:2855.35 RFSD:216.025 RFRSD:7.56563
FitType : Linear
ZeroThrough : Not Through
Weighted Regression : None
Detector Name : PDA

| # | Conc. (Ratio) | MeanArea | Area | Area%RSD |
|---|---|---|---|---|
| 2 | 40.000 | 102011.5 | 101274 | 0.643404 |
| | | | 102227 | |
| | | | 102533 | |
| 3 | 60.000 | 155442.0 | 155081 | 0.732321 |
| | | | 156717 | |
| | | | 154528 | |
| 4 | 80.000 | 236675.9 | 234058 | 0.563785 |
| | | | 236572 | |
| | | | 235791 | |
| | | | 236352 | |
| | | | 239006 | |
| | | | 237117 | |
| | | | 237351 | |
| | | | 237299 | |
| | | | 236537 | |
| 5 | 100.000 | 311576.2 | 308494 | 0.861545 |
| | | | 313402 | |
| | | | 312833 | |

Calibration curve 4

F(x)=2940.95x – 13807.3 $R^2$=0.9912

Calibration Curve

ID# : 1
Name : polymer
Quantitative Method : External Standard
Function : f(x)=2940.95*x-13807.3
Rr1=0.9956348 Rr2=0.9912887
MeanRF:2588.18 RFSD:310.057 RFRSD:11.9798
FitType : Linear
ZeroThrough : Not Through
Weighted Regression : None
Detector Name : PDA

| # | Conc. (Ratio) | MeanArea | Area | Area%RSD |
|---|---|---|---|---|
| 1 | 20.000 | 42343.7 | 41013 | 2.004462 |
| | | | 43358 | |
| | | | 42481 | |
| | | | 42587 | |
| | | | 42280 | |
| 2 | 40.000 | 114661.4 | 107585 | 4.401369 |
| | | | 115399 | |
| | | | 119518 | |
| | | | 116144 | |
| 3 | 60.000 | 156368.8 | 143415 | 7.174533 |
| | | | 162726 | |
| | | | 162966 | |
| 4 | 80.000 | 212209.1 | 216977 | 1.578108 |
| | | | 209356 | |
| | | | 212149 | |
| | | | 208805 | |
| | | | 213758 | |
| 5 | 100.000 | 287664.5 | 290206 | 1.596849 |
| | | | 290426 | |
| | | | 282362 | |

Calibration curve 5

F(x)= 3025.25x – 25644.1 $R^2$=0.9989

Calibration Curve

ID# : 1
Name : polymer
Quantitative Method : External Standard
Function : f(x)=3025.25*x-25644.1
Rr1=0.9994861 Rr2=0.9989725
MeanRF:2453.48 RFSD:338.933 RFRSD:13.8144
FitType : Linear
ZeroThrough : Not Through
Weighted Regression : None
Detector Name : PDA

| # | Conc. (Ratio) | MeanArea | Area | Area%RSD |
|---|---|---|---|---|
| 1 | 20.000 | 37772.7 | 37151 | 2.804797 |
| | | | 38996 | |
| | | | 37172 | |
| 2 | 40.000 | 93034.5 | 90264 | 4.729834 |
| | | | 90731 | |
| | | | 98109 | |
| 3 | 60.000 | 155240.1 | 152298 | 3.735540 |
| | | | 151501 | |
| | | | 161920 | |
| 4 | 80.000 | 212985.5 | 212056 | 0.400524 |
| | | | 213733 | |
| | | | 213167 | |
| 5 | 100.000 | 280322.7 | 276941 | 1.119342 |
| | | | 280888 | |
| | | | 283140 | |

Calibration curve 6

F(x)=2868.62x – 28101.7 $R^2$=0.9966

Calibration Curve

ID# : 1
Name : polymer
Quantitative Method : External Standard
Function : f(x)=2868.62*x-28101.7
Rr1=0.9983355 Rr2=0.9966738
MeanRF:2252.3 RFSD:334.26 RFRSD:14.8408
FitType : Linear
ZeroThrough : Not Through
Weighted Regression : None
Detector Name : PDA

| # | Conc. (Ratio) | MeanArea | Area | Area%RSD |
|---|---|---|---|---|
| 1 | 20.000 | 34176.6 | 35174 | 2.600203 |
| | | | 33886 | |
| | | | 33470 | |
| 2 | 40.000 | 85597.5 | 85864 | 0.727498 |
| | | | 86042 | |
| | | | 84886 | |
| 3 | 60.000 | 136418.7 | 137543 | 0.760084 |
| | | | 135500 | |
| | | | 136213 | |
| 4 | 80.000 | 200092.9 | 197787 | 1.052954 |
| | | | 201917 | |
| | | | 200576 | |
| 5 | 100.000 | 263790.5 | 261806 | 0.0660733 |
| | | | 264493 | |
| | | | 265073 | |

<< PDA >>

ID#1 Compound Name: polymer

| Title | Ret. Time | Area |
|---|---|---|
| segunda fraccion resina.lcd | 10.356 | 5719322 |
| Fraccion H20.lcd | 10.292 | 2174924 |
| polimero 10 mg$50mL_2.lcd | 10.354 | 1398017 |
| polimero 10.1mg$100mL_3.lcd | 10.298 | 629447 |

Methionine

Proline

1

2

<<PDA>>

ID#1 Compound Name: polymer

| Title | Ret. Time | Area |
|---|---|---|
| 1+2_2.lcd | 10.494 | 13911495 |
| Me – Gly_3.lcd | 10.457 | 10744815 |
| RN.lcd | 10.391 | 6434140 |

COLORANT COMPOUNDS DERIVED FROM GENIPIN OR GENIPIN CONTAINING MATERIALS

CROSS-REFERENCE TO RELATED APPLICATIONS

This application a divisional application of U.S. patent application Ser. No. 15/166,391, filed May 27, 2016, which is a divisional application of U.S. patent application Ser. No. 14/285,325, filed May 22, 2014, which claims priority benefit to U.S. Provisional Appl. No. 61/826,391, filed on May 22, 2013, and U.S. Provisional Appl. No. 61/836,072, filed on Jun. 17, 2013, the contents of which are hereby incorporated by reference in their entirety.

BACKGROUND OF THE INVENTION

Statement of Access and Benefit Sharing (ABS)

In compliance with the principles of ABS of the Convention of Biological Diversity and its implementing Nagoya Protocol, access to the genetic resources was obtained through agreements with ethnic communities and the authorities charged by Colombian legislation with administering their collective territories. The assignee has also entered into agreements with several community entrepreneurial initiatives that coordinate local production and supply dynamics with commercial partners. Through a shareholding agreement, these community-owned suppliers share in the financial benefits of commercialization of the genetic resources. Additional benefit sharing is provided through Fundación Espavé, a nonprofit organization that is a member of the Union for Ethical BioTrade and that trains local producers on sustainable sourcing in the Pacific rainforest.

1. Field of the Invention

The present disclosure is related to colorant compounds isolated from a reaction of *Genipa americana* juice, genipin or genipin analogs and an amine, compositions comprising the same, and methods of making and using the same.

2. Background of the Invention

Distrust of consumers in the use of synthetic colorants, mainly because of their toxicity, has led to the research and development of natural color compounds. These compounds have been utilized for many centuries, but recent technology advances allowed these colorants to be industrially and commercially viable and be able to compete with the synthetic ones. See "Market Brief in the European Union for selected natural ingredients derived from native species; *Genipa americana*," presented in United Nations Conference on Trade and Development (2005). Internationally, natural colours such as blue and black colorants of *Genipa americana* are used by both the food, the cosmetics and the textile industry.

Methods of preparing blue colorants have been reported. For example, a method to make a pH stable blue colorant, derived from the mix of unprocessed raw juice obtained from *Genipa americana* fruit pulp and glycine, was described in Echeverri et al. (U.S. Pat. No. 7,927,637), the content of which is incorporated herein by reference in its entirety. Other examples of preparing blue colorants include JP Patent publication Nos. 52053932A2 and 52053934A2, H. Okuyama et al., which describe a blue-violet colorant made from a spontaneous reaction of primary amines with genipin; and Wu et al (WO 2009/120579), which describes mixing the *Genipa americana* juice with other fruit juices (e.g. watermelon) and amino acids. These existing methods generally use the resulted crude mixture without further purification, possibly due to the difficulty recognized in the art for purifying the mixtures. See Touyama R. et al., Studies on the Blue Pigments Produced from genipin and methylamine. I. Structures of the Brownish-Red Pigments, Intermediates Leading to the Blue Pigments, Chem Pharm. Bull 42, 66, 1994 (the blue pigment derived from a reaction of genipin or structural analogs and amino acids have been "found to be an intractable mixture of high molecular polymers on the basis of its chromatographic behavior, un-analyzable $^{13}$C-NMR spectrum and by molecular weight measurements"). There has been a limited description of the blue pigment material molecular structure since this material is almost soluble only in water due to its very high polarity which results in hard TLC monitoring. A polymer of 9000 molecular weight has been reported (see H. Jnouye, Y. et al., 26th Symposium on the Chemistry of Natural Product, Kyoto, Abstr. pp 577-584, 1983). More recently, Wu and Horn (U.S. Pub. No. 2013/0115252) described a method of enriching genipin from *Genipa americana* and the uses of enriched genipin material. However, the "genipin-rich extract" is disclosed as being 30-97% (w/w) genipin with the remainder of the composition including moisture, fat, small amounts of acids and nitrogen-containing compounds, with the balance being carbohydrates (see U.S. Pub. No. 2013/0115252, page 3, left column).

SUMMARY OF THE INVENTION

The present invention contributes to overcome the lack of knowledge regarding the molecular structures of the blue pigment material derived from a reaction of genipin with an amino-acid. Provided herein are colorant compositions comprising substantially purified colorant compounds (e.g., polymers), and methods of isolating colorant compounds and methods of using the isolated colorant compounds.

Certain embodiments are directed to a substantially purified compound of formula 1A or formula 1B, a geometric isomer thereof, a tautomer thereof, a salt thereof, or a combination thereof;

Formula 1A

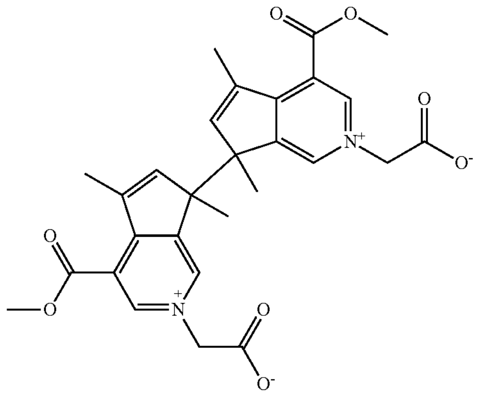

-continued

Formula 1B

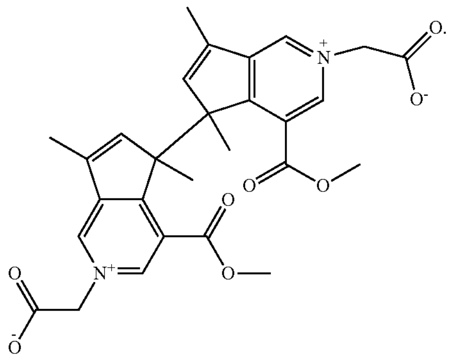

Certain embodiments are directed to a substantially purified compound of formula 2, 3A, or 3B, a geometric isomer thereof, a tautomer thereof, a salt thereof, or a combination thereof;

Formula 2

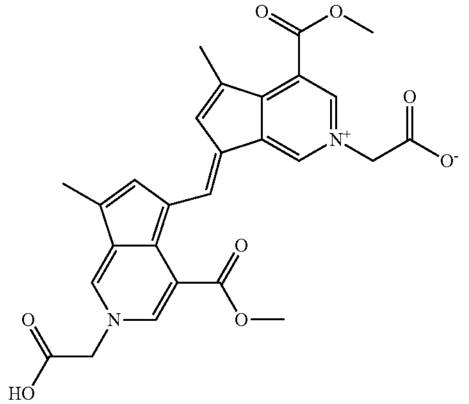

Formula 3A

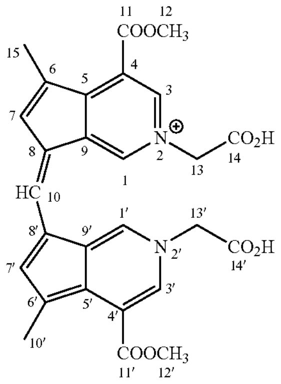

Formula 3B

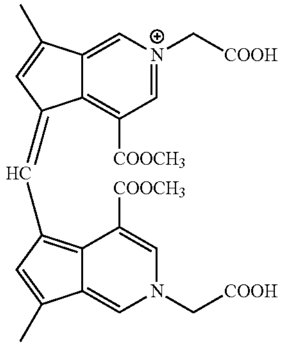

Certain embodiments are directed to a colorant composition comprising a polymer of Formula 4:

$$T^1\left(-A-CH_2-\right)_n-T^2$$ Formula 4, a geometric isomer thereof, a tautomer thereof, or a salt thereof, wherein n is an integer from 2 to 200;

wherein each A is independently selected from the group consisting of formula 5A, formula 5B, formula 5C, a geometric isomer thereof, a tautomer thereof, a salt thereof, and a combination thereof:

Formula 5A

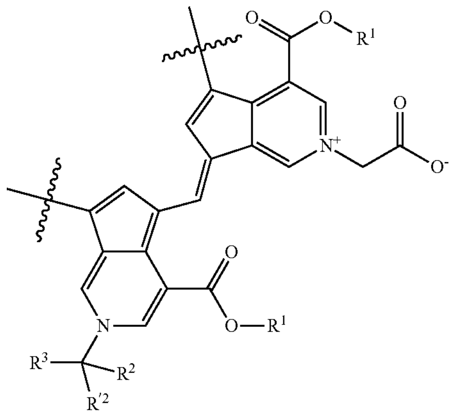

Formula 5B

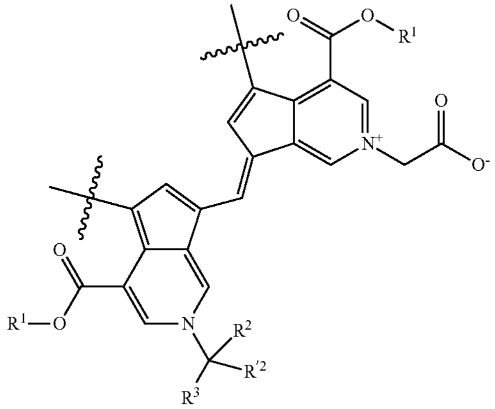

Formula 5C

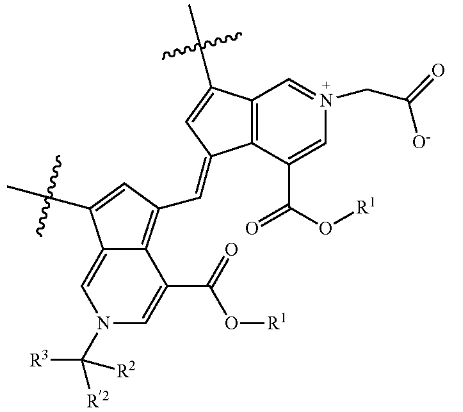

wherein:

$R^1$ is hydrogen, methyl, ethyl, propyl, isopropyl, butyl, sec-butyl, isobutyl, or tert-butyl;

$R^2$ and $R'^2$ are independently hydrogen, or $C_{1-10}$ alkyl;

$R^3$ is hydrogen or COOH;

and wherein $T^1$ is hydrogen or a methyl group; and $T^2$ is hydrogen or $A\text{-}T^1$, wherein A and $T^1$ are defined above;

wherein the colorant composition is substantially free of a first additional compound selected from the group consisting of formula 6, formula 7, formula 8, a geometric isomer thereof, a tautomer thereof, and a salt thereof:

Formula 6

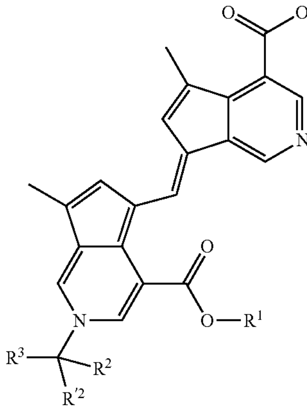

Formula 7

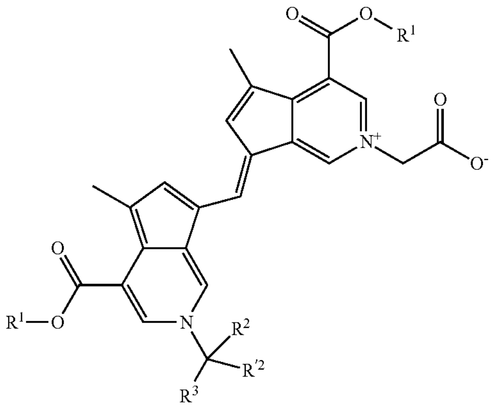

Formula 8

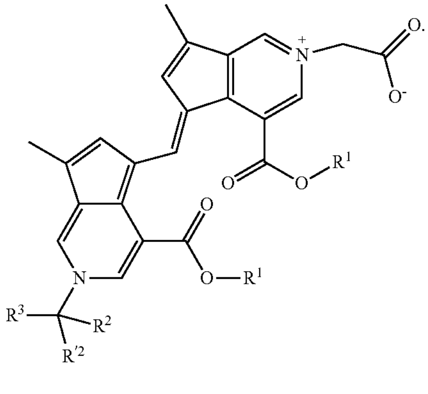

In some embodiments, a colorant composition comprises a polymer of Formula 4:

$$T^1\text{-}(\text{-A-CH}_2\text{—})_n\text{-}T^2 \quad \text{Formula 4,}$$

a geometric isomer thereof, a tautomer thereof, or a salt thereof, wherein n is an integer from 2 to 20;

wherein each A is independently selected from the group consisting of formula 5'A, formula 5'B, formula 5'C, a geometric isomer thereof, a tautomer thereof, a salt thereof, and a combination thereof:

Formula 5'A

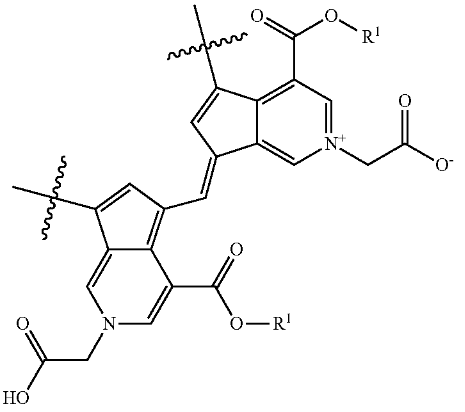

Formula 5'B

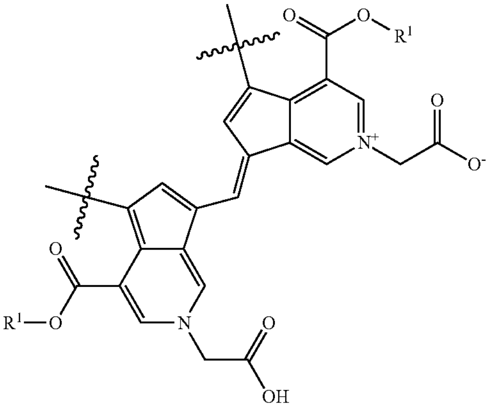

Formula 5'C

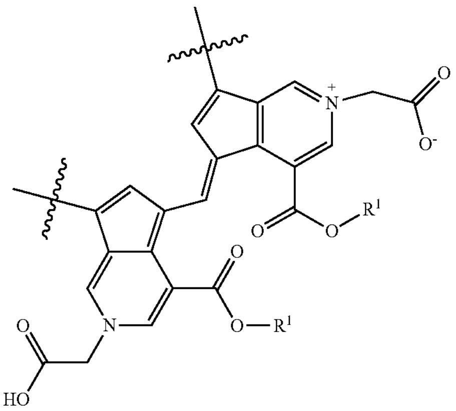

wherein:

$R^1$ is hydrogen, methyl, ethyl, propyl, isopropyl, butyl, sec-butyl, isobutyl, or tert-butyl;

and wherein $T^1$ is hydrogen or a methyl group; and $T^2$ is hydrogen or $A\text{-}T^1$, wherein A and $T^1$ are defined above;

wherein the colorant composition is substantially free of a first additional compound selected from the group consisting of formula 2', formula 3'A, formula 3'B, a geometric isomer thereof, a tautomer thereof, and a salt thereof:

Formula 2'

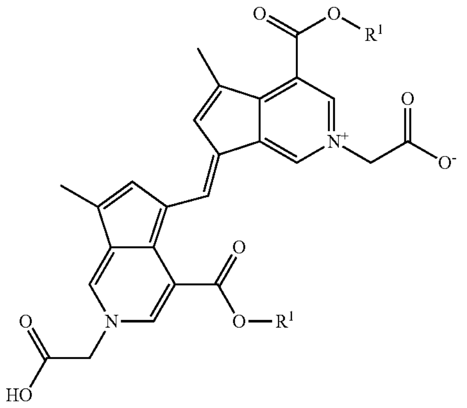

Formula 3'A

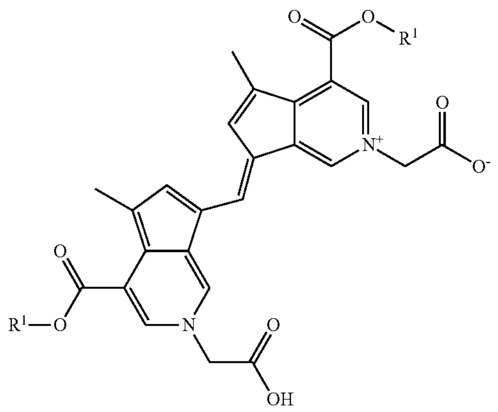

Formula 3'B

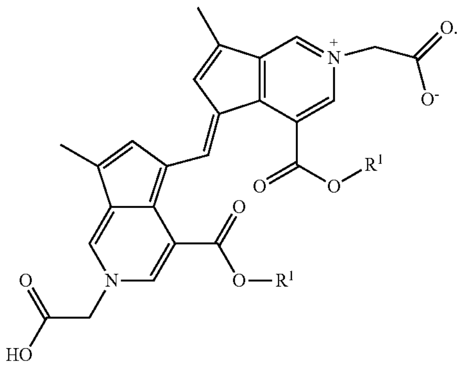

In some embodiments, $R^1$ is methyl. In some embodiments, total weight of the first additional compound is less than 1% by weight of the polymer.

Certain embodiments are directed to a substantially purified compound of formula 3'A (Me) or formula 3'B (Me), a geometric isomer thereof, a tautomer thereof, a salt thereof, or a combination thereof:

Formula 3'A (Me)

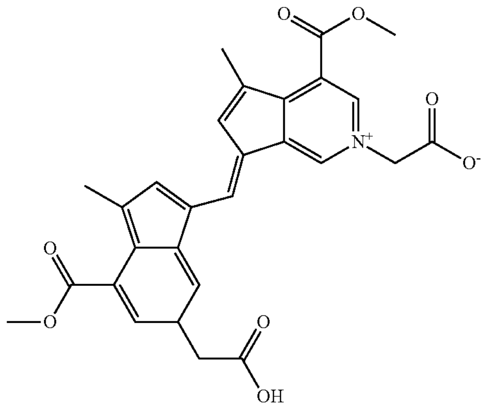

Formula 3'B (Me)

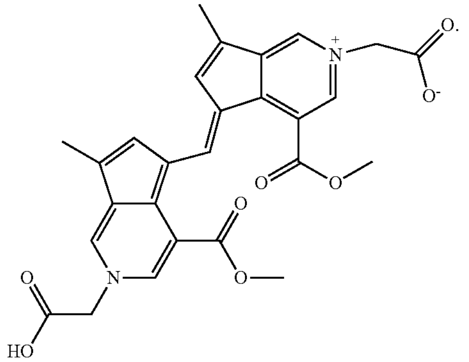

Certain embodiments are directed to a substantially purified polymer of Formula 4:

$$T^1\text{-}(\text{-A-CH}_2\text{-})_n\text{-}T^2 \quad \text{Formula 4,}$$

a geometric isomer thereof, a tautomer thereof, or a salt thereof, wherein n is an integer from 2 to 20;

wherein each A is of formula 5'A (Me), a geometric isomer thereof, a tautomer thereof, or a salt thereof:

Formula 5'A (Me)

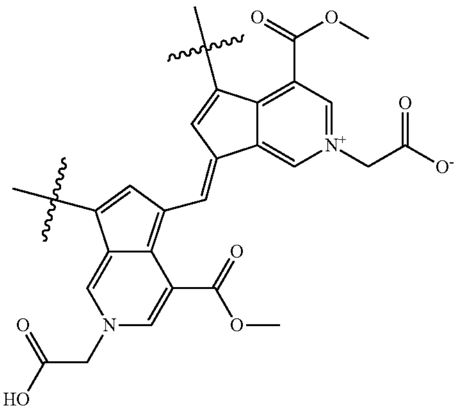

wherein $T^1$ is hydrogen or a methyl group; and $T^2$ is hydrogen A-$T^1$, or wherein A and $T^1$ are defined above.

Certain embodiments are directed to purified colorant compounds and methods of isolation of the colorant compounds derived from a reaction of genipin and glycine. In some embodiments, the colorant compounds are derived from a reaction of purified genipin (e.g., more than 80%, 85%, 90%, 95%, or 99% by weight) and glycine. In some embodiments, the colorant compounds are derived from a reaction of glycine and a juice containing genipin. In some embodiments, the colorant compounds are derived from a reaction of glycine and a fruit juice derived from *Genipa americana*. In some embodiments, the colorant compounds are derived from a reaction of a purified glycine with genipin, wherein the genipin is a purified genipin (e.g., more than 80%, 85%, 90%, 95%, or 99% by weight) or a juice containing genipin. In some embodiments, the colorant compounds are derived from a reaction of genipin and a mixture containing glycine (e.g., a juice containing glycine, or a dry mix containing glycine such as a juice concentrate containing glycine), wherein the genipin is a purified genipin (e.g., more than 80%, 85%, 90%, 95%, or 99% by weight) or a juice containing genipin. In some embodiments, the colorant compounds are derived from a reaction of a juice containing glycine (e.g., a fruit juice such as a juice derived from watermelon, white grape, pineapple, lychee, cantaloupe, banana, orange, apple, pear, lemon, passion fruit, red grape, blueberry, tamarind, peach, papaya, acai, plum, guava, tangerine, borojo, cupuacu, goji, or kiwi) and a juice containing genipin (e.g., a fruit juice such as a juice derived from *Genipa americana*). In some embodiments, the colorant compounds are derived from a reaction of a juice derived from watermelon and a juice derived from *Genipa americana*.

Certain embodiments are directed to a method of isolating colorant compounds, the method comprising: extracting a blue mixture derived from a reaction of genipin and glycine with an alcoholic solvent to produce an alcohol-soluble fraction and an alcohol-insoluble fraction; and purifying either the alcohol-soluble fraction or the alcohol insoluble fraction. In some embodiments, the blue mixture is a dry powder (e.g., a lyophilized powder) derived from the reaction of genipin and glycine.

Certain embodiments are directed to a substantially purified colorant compound comprising a purified polymer of Formula 4, a geometric isomer thereof, a tautomer thereof, or a salt thereof. In some embodiments, the substantially purified colorant compound comprises a dimer of formula 2, 3'A (Me), or 3'B (Me). In some embodiments, the substantially purified colorant compound, e.g., a polymer (e.g., of Formula 4, a geometric isomer thereof, a tautomer thereof, or a salt thereof), is free of carbohydrates, e.g., sugars. In some embodiments, the substantially purified colorant compound comprises a polymer (e.g., of Formula 4, a geometric isomer thereof, a tautomer thereof, or a salt thereof) at least 80%, 85%, 90%, 95%, 99%, or 100% free of carbohydrates and at least 80%, 85%, 90%, 95%, 99%, or 100% free of other impurities, e.g., monomers, dimers, fatty acids, fat, proteins and/or organic acids.

In some embodiments, a method of imparting blue color to a substrate comprises contacting the substrate with a colorant composition described herein. In some embodiments, the substrate is a food item, a drug or nutraceutical product, a cosmetic product, or a medical device. In some embodiments, the colorant composition comprises a purified polymer of Formula 4, a geometric isomer thereof, a tautomer thereof, or a salt thereof. In some embodiments, the colorant composition comprises a substantially pure dimer of formula 2, 3'A (Me), or 3'B (Me).

BRIEF DESCRIPTION OF THE DRAWINGS

FIGS. 19A-C show, for each amino acid, (19A) Glycine, Lysine, and Valine, (19B) Methionine and Proline, and (19C) Tyrosine and Tryptophan, the following: HPLC spectra of reaction products of *Genipa americana* juice with the amino acid using a method of Example 6; an enlarged view of HPLC region where a polymer is identified; and UV-vis spectra of selected signal.

DETAILED DESCRIPTION OF THE INVENTION

Definitions

Figure 1B:
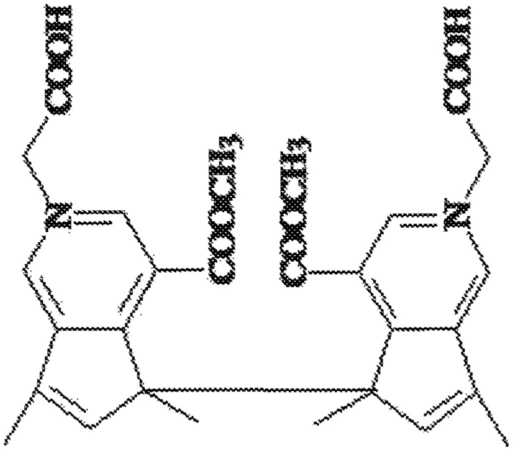
FIGS. 1A-B show chemical formulas for both isomeric forms of compound No. 1.
Figure 1A:
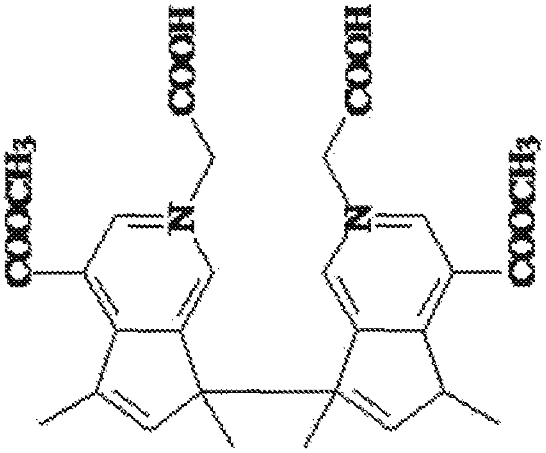
Figure 2A:
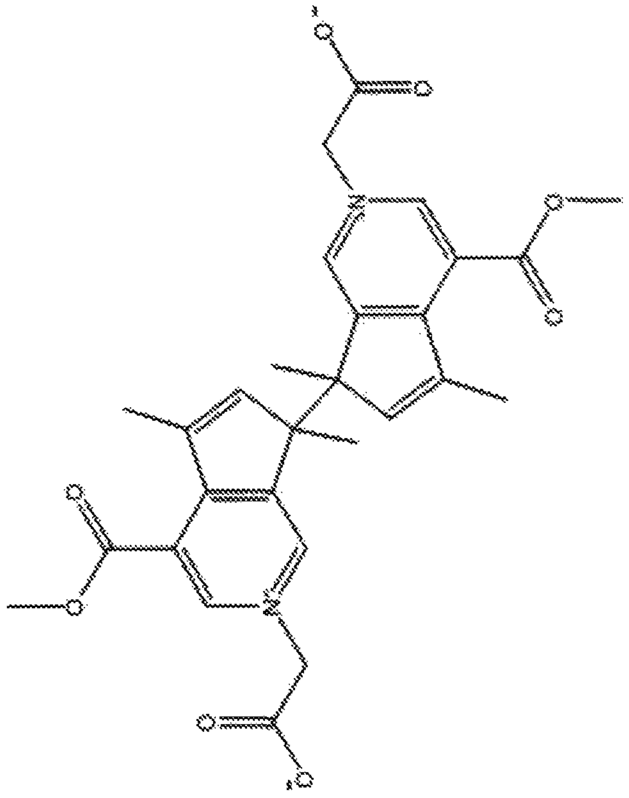
FIGS. 2A-B show another representation of the chemical formulas for both isomeric forms of compound No. 1.
Figure 2B:
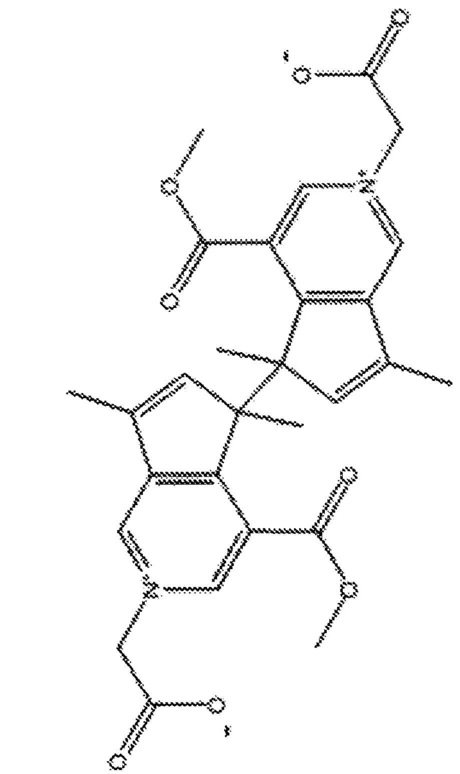

As used herein, the term "polymer" means a chemical compound or mixture of compounds formed by polymerization and consisting essentially of repeating structural units.

A purified polymer herein can be understood as a purified single chemical compound with a specific molecular structure and a fixed number of repeating structural units. A purified polymer can also be understood as a mixture of polymeric compounds formed in a polymerization reaction with various degree of polymerization (i.e., the number of repeating structural units can be different).

Scheme 1 shows an exemplary polymerization reaction of reactant 1 (e.g., genipin, $R^1$=Me) and reactant 2 (e.g., glycine, $R^3$=COOH, $R^2$ and $R'^2$ are H). A purified polymer from the reaction described in Scheme 1 can then be an isolated polymer composition of a certain purity (e.g., containing more than 75%, 80%, 85%, 90%, or 95% of polymer by weight) of a single polymeric molecule (a single polymer molecule of Formula 4 means that $T^1$, $T^2$, A and n in the formula are fixed). A purified polymer from the reaction described in Scheme 1 can also be an isolated polymer composition of a certain purity (e.g., containing more than 75%, 80%, 85%, 90%, or 95% of polymer by weight) of a mixture of polymeric compounds formed in the reaction mixture that share the same repeating structural units but with varying degree of polymerization (e.g., in Formula 4, the polymeric compounds would have the same value of A, but with different value of n).

Scheme 1

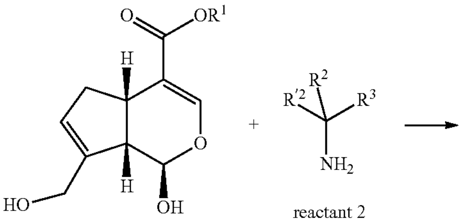

reactant 1 reactant 2

$$T^1-(A-CH_2)_n-T^2$$

Formula 4

In certain embodiments, the polymer herein is characterized by a molecular formula, e.g., Formula 4, a geometric isomer thereof, a tautomer thereof, or a salt thereof. As used herein, the term "a polymer of Formula 4" or polymers of formula 4 means a polymer or polymers having a structure according to Formula 4, or a geometric isomer thereof, a tautomer thereof, or a salt thereof. In certain embodiments, the polymer herein is characterized by physical data (e.g., spectral data, molecular weight distribution). Methods for characterization of a polymer are known in the art. For example, a polymer can be characterized by spectroscopic methods (e.g., IR, UV/vis, NMR, MS, etc.); and molecular weight of a polymer can be analyzed to obtain a number average molecular weight ($M_n$), and/or weight average molecular weight ($M_w$).

The term geometric isomers as used herein mean isomers of identical structure except with different configurations at the double bond(s) (i.e., E or Z isomer, or cis/trans isomer). For illustration, Scheme 2 shows an example of a pair of two geometric isomers, where the only difference between the two isomers is the configuration at the double bond.

Scheme 2

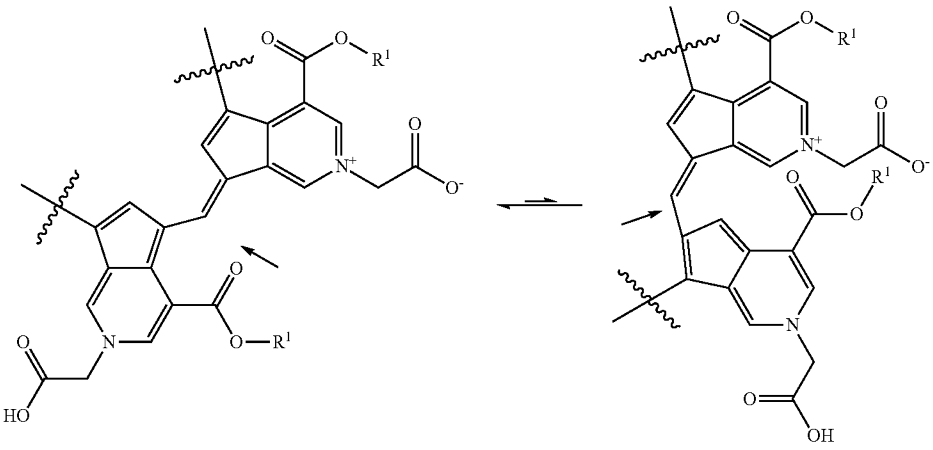

geometric isomer 1 geometric isomer 2

The term tautomers or tautomeric isomers as used herein means compounds that can be interconvertible through tautomerization. Tautomerization is known in the art and generally refers to a reaction as shown in Scheme 3A. In most cases, group G in the reaction is hydrogen.

Scheme 3A

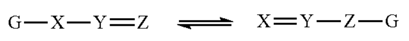

tautomer 1 tautomer 2

A further example of tautomers is shown in Scheme 3B. Scheme 3B is not to be understood as a showing of all possible tautomer structures.

Scheme 3B

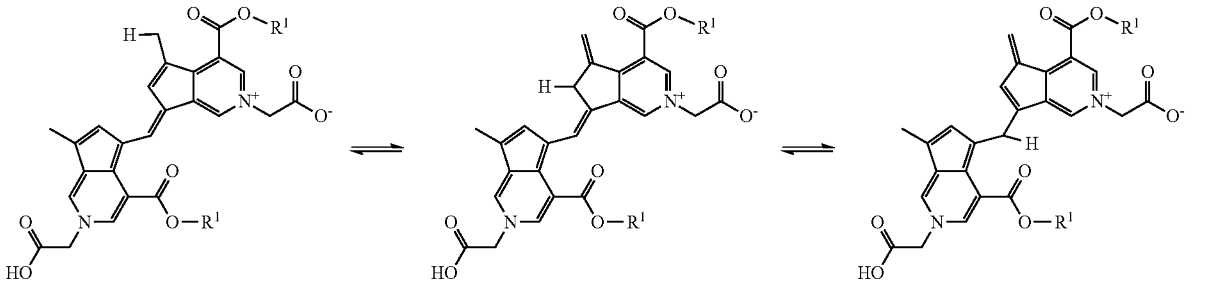

tautomer 1 tautomer 2 tautomer 3

The arrows used in Schemes 2, 3A, and 3B are for illustration purposes and are not to be construed as the actual equilibrium between the isomers or tautomers.

As used herein, the term "salt" is understood to include both internal salt or external salt, unless specified otherwise. Examples of external salts include salts having a cation as a counterion, such as an alkaline metal ion (e.g., $Na^+$, $K^+$, etc.), an alkaline earth metal ion (e.g., $Mg^{2+}$, $Ca^{2+}$, etc.), ammonium ion (e.g., $NH_4^+$, or an organic ammonium ion), etc. Examples of external salts also include salts having an anion as a counterion, such as an inorganic anion (e.g., $Cl^-$, $SO_4^{2-}$, $Br^-$, $HSO_4^-$, etc.) or an organic anion (e.g., a carboxylic acid anion such as a formate, acetate, etc.).

As used herein, compounds No. 1, 2, and 3 refer to the compounds isolated from a reaction of genipin and glycine as described in the Examples section.

As used herein, a dimer or a dimeric compound means a compound consisting essentially of two monomers. Examples of dimers include compounds No. 1, No. 2, No. 3, and compounds of formula 1A, 1B, 2, 3A, 3B, 2', 3'A, 3'B, 3'A (Me), 3'B (Me), 6, 7, and 8.

As used herein, "substantially free of" a compound (e.g., a first additional compound, a second additional compound, or a combination thereof) means total weight of the compound is less than 5% by weight of a reference (e.g., a polymer of Formula 4. a geometric isomer thereof, a tautomer thereof, or a salt thereof). In some embodiments, "substantially free of" a compound means total weight of the compound is less than 4.5%, less than 4%, less than 3%, less than 2%, less than 1%, less than 0.5%, less than 0.1%, or less than 0.01% by weight of a reference (e.g., a polymer of Formula 4. a geometric isomer thereof, a tautomer thereof, or a salt thereof). In some embodiments, a composition (e.g., a colorant composition) "substantially free of" a compound means the composition is free of the compound. In some embodiments, "substantially free of" a compound means total weight of the compound is 0.01-5%, 0.01-4.5%, 0.01-4%, 0.01-3%, 0.01-2%, 0.01-1%, 0.01-0.5%, or 0.01-0.1% by weight of a reference (e.g., a polymer of Formula 4. a geometric isomer thereof, a tautomer thereof, or a salt thereof).

As used herein, the term "a substantially purified" or a substantially pure compound (e.g., a substantially purified polymer, a substantially purified dimer) means a compound having a purity of greater than 80% (e.g., more than 80%, 85%, 90%, 95%, or 99% by weight (e.g., dry weight, i.e., not counting volatile components such as solvents (e.g., water, $CH_3CN$, MeOH, EtOH, etc.)). In some embodiments, a substantially pure polymer of formula 4, a geometric isomer thereof, a tautomer thereof, or a salt thereof, comprises greater than 80%, 85%, 90%, 95%, or 99% of the polymer, geometric isomer thereof, tautomer thereof, or salt thereof by dry weight.

The term purified genipin used herein refers to a substance that comprises more than 80%, 85%, 90%, 95%, or 99% by weight of genipin. Similarly, the term purified glycine used herein refers to a substance that comprises more than 80%, 85%, 90%, 95%, or 99% by weight of glycine.

Purity of colorants of this disclosure can be measured by known analytical methods (e.g., high-performance liquid chromatography (HPLC) analysis). Thus, quantification of a compound (e.g., a dimer, a polymer) in a sample can be achieved by utilizing HPLC methods, e.g., similar to the methods described in the Examples section.

Colorant Compositions Comprising a Dimer

The present invention provides colorant compounds and their molecular structural formulas and methods of isolation of the colorant compounds derived from a reaction of *Genipa americana* genipin and glycine. In some embodiments, the compounds are obtained from multiple fractioning by chromatography of the reaction resulting material. In some embodiments, the molecular structural formulas are determined by $^1$H nuclear magnetic resonance spectroscopy ($^1$HNMR), J-Modulation (JMOD), $^1$H Correlation Spectroscopy (COSY $^1$H-$^1$H) experiments, and other molecular structural tools analysis.

In some embodiments, a colorant compound of the formula 3A (in the present application, formula 3A is for compound No. 3 in the preferred isomeric form):

Formula 3A

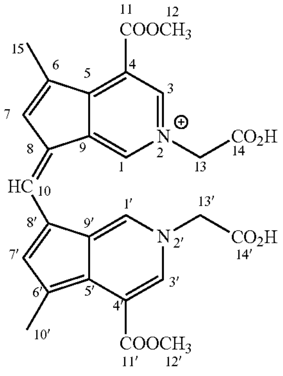

In another embodiment, the colorant compound has the isomeric form of formula 3B (in the present application, formula 3B is for compound No. 3 in an isomeric form):

Formula 3B

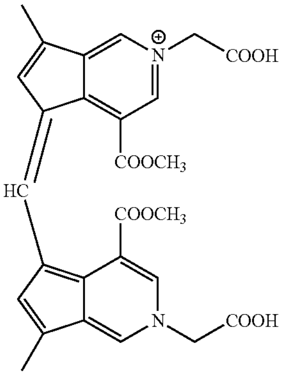

Certain embodiments are directed to a method of isolating the colorant compound of formula 3A:

Formula 3A

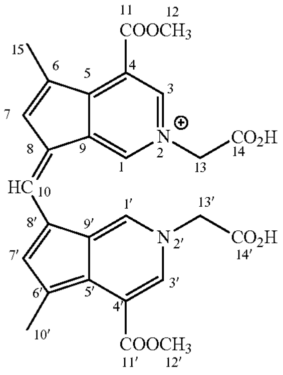

Wherein the methods comprises:

A. Isolating genipin from *Genipa americana* juice;

B. Reacting glycine with said genipin to obtain a material soluble in methanol;

C. Separating by chromatography the material soluble in methanol into S1, S2, S3, and S4 fractions.

D. Separating again by chromatography the S3 fraction into S31, S32, S33 and S34 fractions. Isolating by reverse phase chromatography from the S33 fraction the compound of formula I.

A less preferred embodiment is directed to a method of isolating a compound having the isomeric form of Formula 3B:

Formula 3B

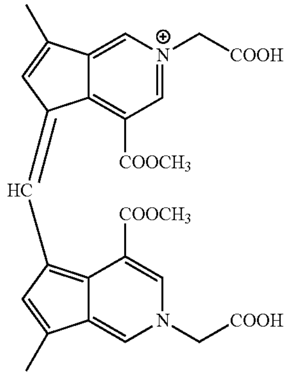

the method comprising:

A. Isolating genipin from *Genipa americana* juice;

B. Reacting glycine with said genipin to obtain a material soluble in methanol;

C. Separating by chromatography the material soluble in methanol into S1, S2, S3, and S4 fractions.

D. Separating again by chromatography the S3 fraction into S31, S32, S33 and S34 fractions.

E. Isolating by reverse phase chromatography from the S33 fraction the compound of formula I.

Figure 3A:
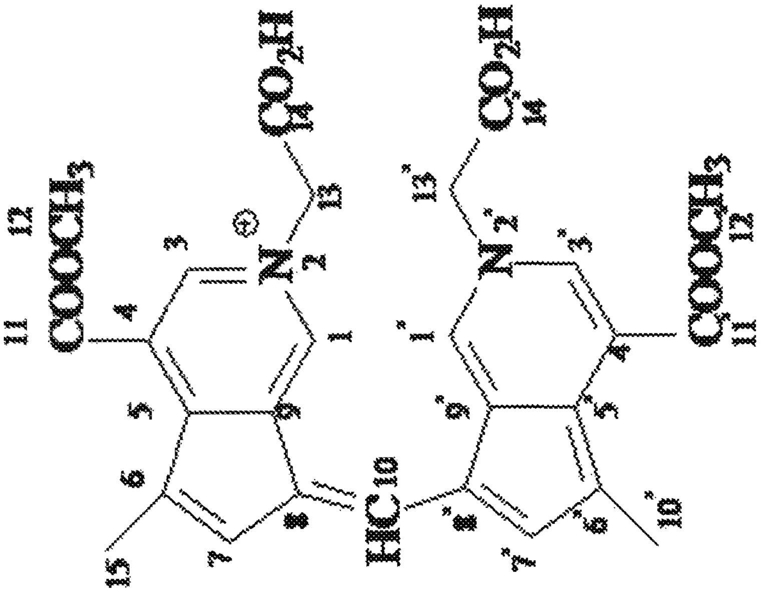
FIGS. 3A-B show chemical formulas for both isomeric forms of compound No. 3.
Figure 3B:
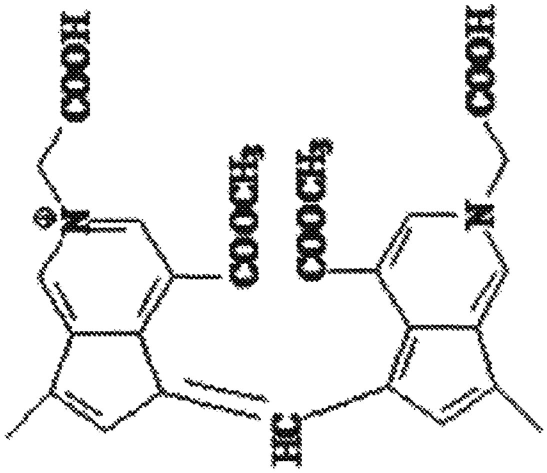
Figure 4A:
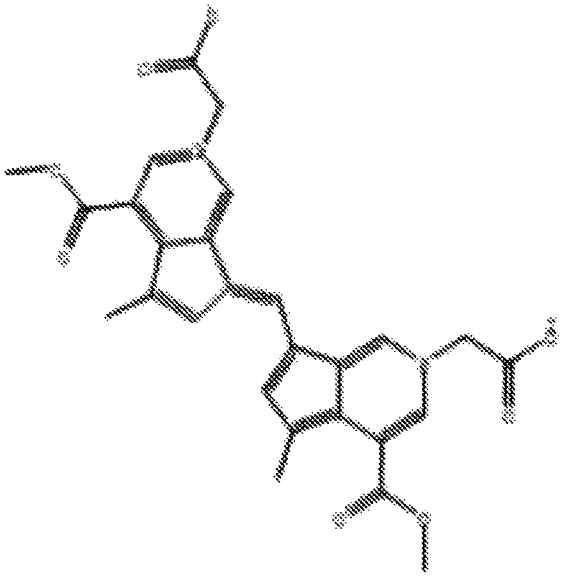
FIGS. 4A-B shows another representation of the chemical formulas for both isomeric forms of compound No. 3.
Figure 4B:
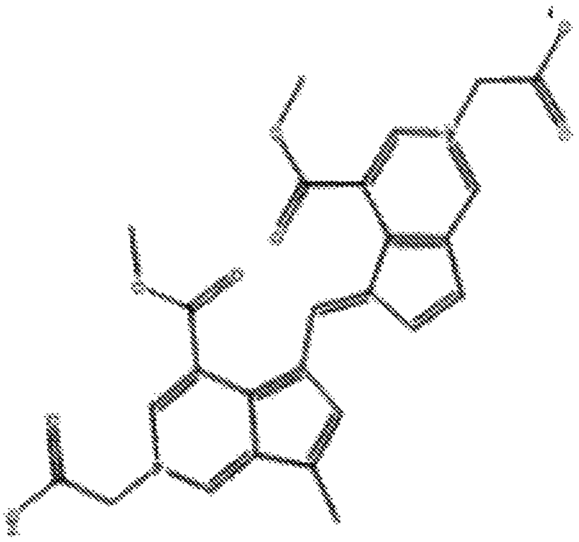
Figure 6:
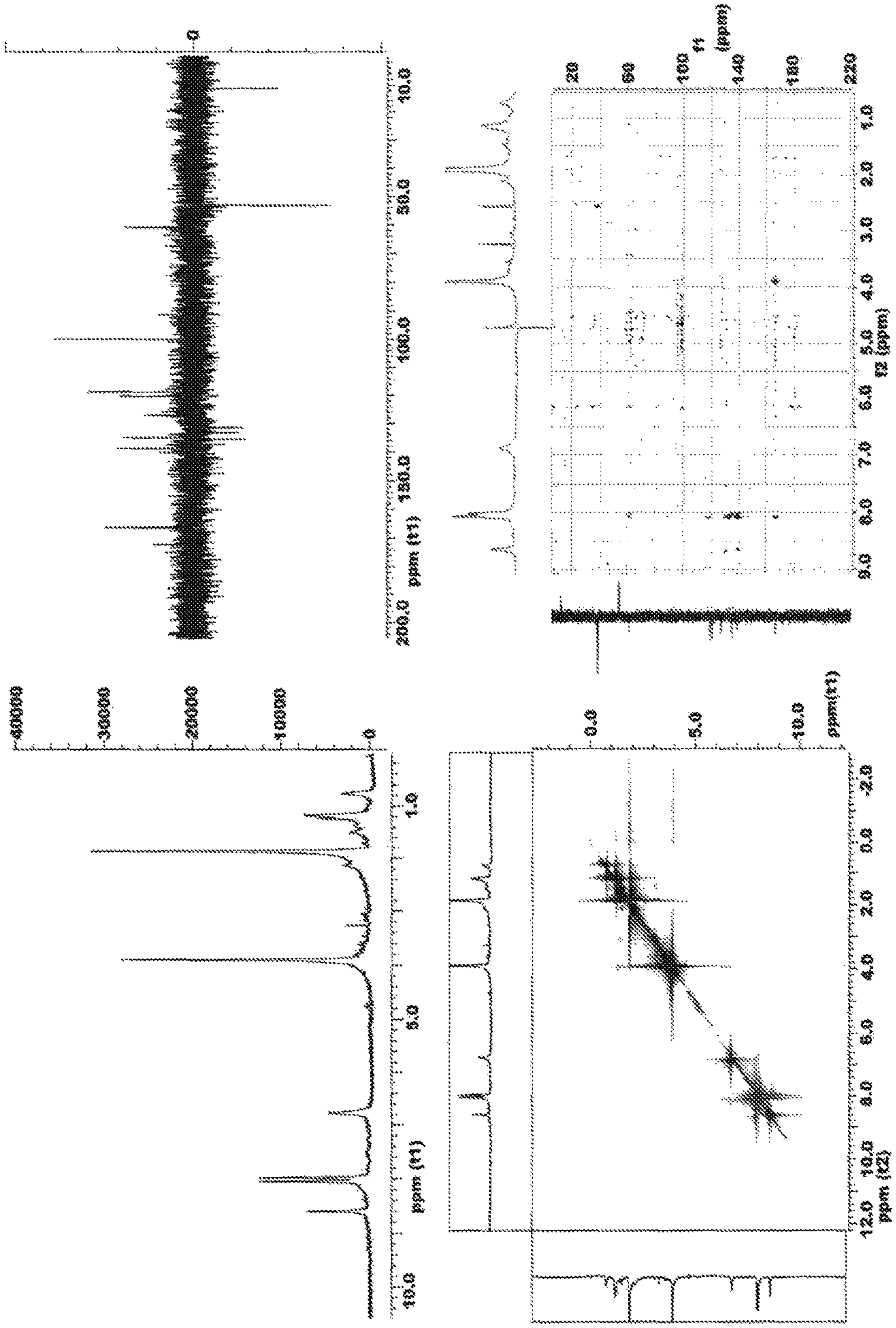
FIG. 6 shows an NMR spectroscopy spectra of compound 3 isolated from a reaction of genipin and glycine.

FIGS. 3A and 4A show representations of the chemical formula for the preferred isomeric form of compound No. 3. Compound No. 3 is a very dark blue colorant substance. FIGS. 3B and 4B shows the less preferred isomeric form of compound No. 3. FIG. 6 shows the nuclear magnetic resonance (NMR) spectroscopy profile of compound No. 3. Analysis of the NMR spectroscopy profile of compound No. 3. Shows:

$^{1}$H NMR (400 MHz, $D_2O$). δ 8.6, 8.0, 7.9, 6.7, 3.90, 1.8 ppm.

$^{13}$C NMR (100 MHz). δ 172.2, 166.3, 138.8, 135.6, 135.1, 133.3, 131.4, 127.1, 120.46, 118.9, 61.0, 53.3, 11.2 ppm.

m/z 505 [M+H]

Further analysis of compound No. 3 showed that:

The mass spectra of the compound 3 displayed m/z=505 $[M+H]^+$. in mass spectrometry, so indicating an isomer of the compound previously described. However, the $^{1}$H and $^{13}$CNM spectra were very different to that one. In the proton spectra, the following singlets were detected: δ 8.0, δ 7.9, and δ 6.7 (2H each one) and one additional singlet at δ 8.6 integrating for 1H. Other signals were a singlet at δ 4.7 (N—CH2) and two methyl groups at δ 3.9 ($OCH_3$) and δ 1.8 ($CH_3$ vinyl. According to JMOD experiment, the following carbon atoms were observed too: a carboxyl group at δ 172.2, a methylester at δ 166.3, (COOH), five quaternary carbon atoms at δ 138.8, δ 135.1, δ 127.1, δ 120.4, δ 118.9, four methines at δ 135.6, δ 133.3, δ 131.4, δ 131.4, one methylene (N—$CH_2$) at δ 61.0 and two methyl groups at δ 53.3 ($OCH_3$) and δ 11.2 ($CH_3$ vinyl). The structure of each monomer unit was assigned according to HMBC experiment: signals at δ 7.9 and δ 8.0 were assigned to protons of the pyridil group, since a long range correlation to the N-methylene group at δ 61.0 was detected; additionally the last proton display $^3J$ coupling to the methylester carbonyl at δ 172.2. Besides other important coupling was shown between the singlet at δ 131.4 (C-7) with protons of the methyl group. The low amounts of aromatic and vinyl proton indicated the presence of a symmetric dimeric molecule such as is showed in FIGS. 3A-3B. Two structures could be assigned to this molecule, according to the relative orientation of the methylester group (FIGS. 3A-3B), but structure B has a low probability due to steric hindrance, again.

Figure 7:
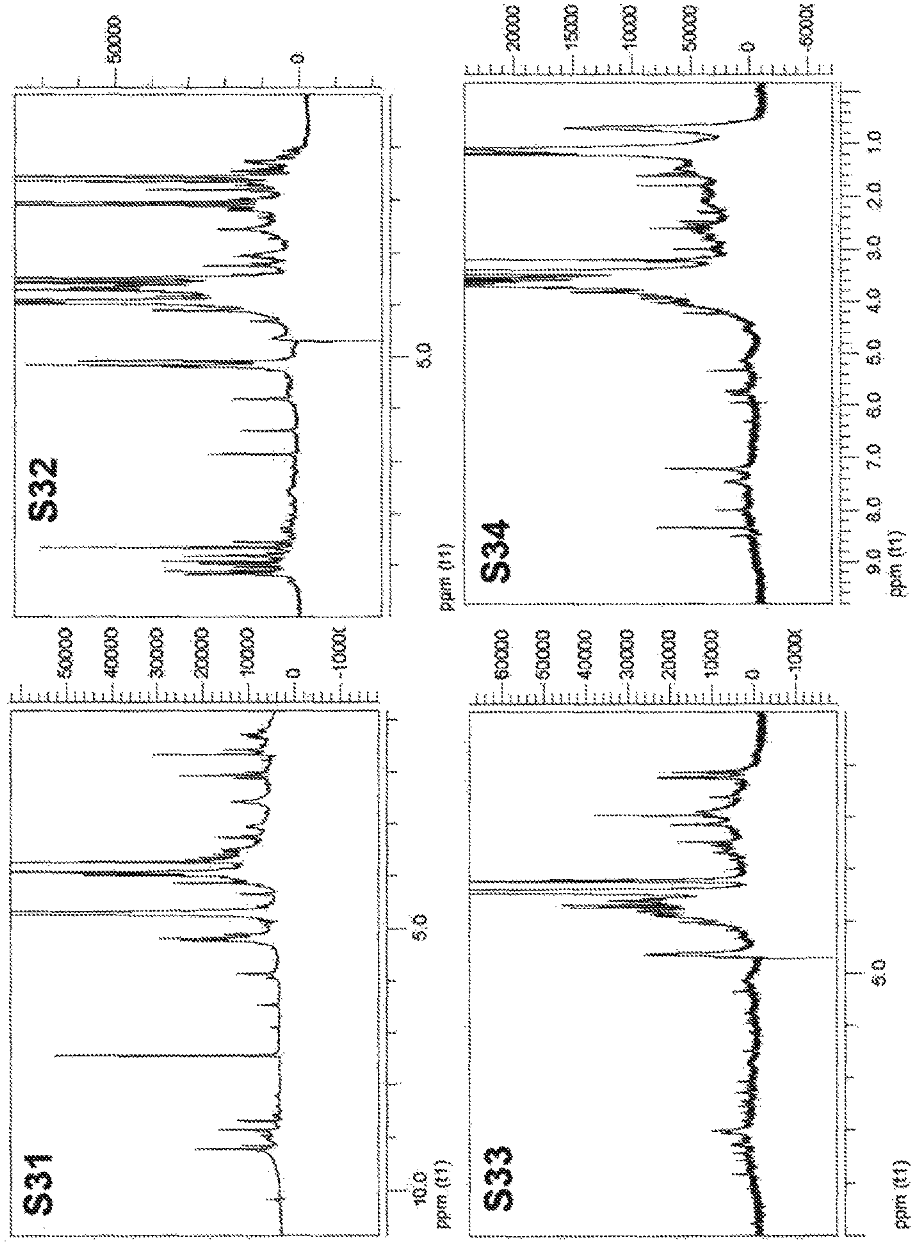
FIG. 7 shows NMR spectra for the S31, S32, S33, and S34 fractions (derived from the S3 fraction) isolated from a reaction of genipin and glycine.

In another embodiment, a method of isolating the colorant compound No. 3 comprises:

A. Isolating genipin from *Genipa americana* juice;
B. Reacting glycine with said genipin to obtain a material soluble in methanol;
C. Separating by chromatography the material soluble in methanol into S1, S2, S3, and S4 fractions.
D. Separating again by chromatography the S3 fraction into S31, S32, S33 and S34 fractions (FIG. 7). Isolating by reverse phase chromatography from the S33 fraction the compound of formula I.

In the present application, the terms S1, S2, S3, S4, and S31, S32, S33 and S34 are a way to define the fractions derived from the described steps of the method. However, these terms (S1, S2, S3, S4, and S31, S32, S33 and S34) cover any fractions obtained by similar chromatographic steps and which could be derived from a reaction genipin and glycine, wherein a S3 similar fraction and S3 derived fractions (of similar NMR spectroscopy as shown in FIG. 7) are produced. FIG. 7 shows the NMR spectroscopy of the S3 fraction derived S31, S32, S33 and S34 fractions.

In some embodiments, a colorant composition comprises a substantially pure compound of Formula 1A, 1B, 2, 3'A (Me), and 3'B (Me) isolated from a reaction of genipin and glycine.

In some embodiments, a method of isolating the colorant compound No. 3 comprises:

A. Isolating genipin from *Genipa americana* juice;
B. Reacting glycine with said genipin to obtain a material soluble in methanol;
C. Separating by chromatography the material soluble in methanol into S1, S2, S3, and S4 fractions.
D. Separating again by chromatography the S3 fraction into S31, S32, S33 and S34 fractions (FIG. 7). Isolating by reverse phase chromatography from the S33 fraction the compound 3.

For the purpose of the present Application the terms S1, S2, S3, S4, and S31, S32, S33, S34, and M2S1R, M2S2R, M2S3R, M2S4R, and i1 and i2 are a way to define the fractions derived from the described steps of the method. However, these terms (S1, S2, S3, S4, and S31, S32, S33 and S34) cover any fractions obtained by similar chromatographic steps and which could be derived from a reaction genipin and glycine, wherein a S3 similar fraction and S3 derived fractions (of similar NMR spectroscopy as shown in FIG. 7) are produced. FIG. 7 shows the NMR spectroscopy of the S3 fraction derived S31, S32, S33 and S34 fractions.

Certain embodiments are directed to a substantially purified compound of formula 3'A (Me) or formula 3'B (Me), a geometric isomer thereof, a tautomer thereof, a salt thereof, or a combination thereof:

Formula 3'A (Me)

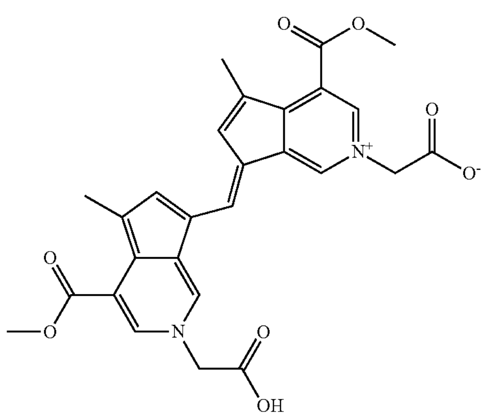

Formula 3'B (Me)

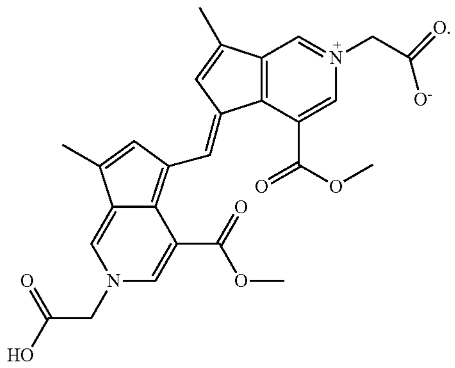

Certain embodiments are directed to a substantially purified compound of formula 1A or formula 1B, a geometric isomer thereof, a tautomer thereof, a salt thereof, or a combination thereof;

Formula 1A

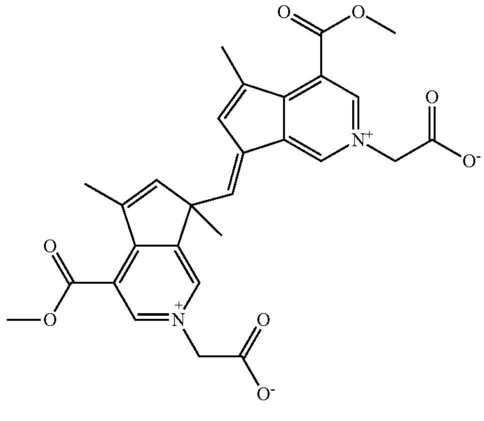

-continued

Formula 1B

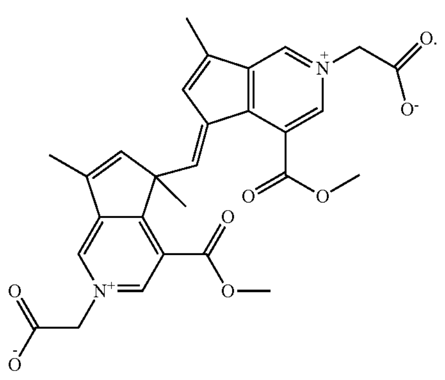

Composition Comprising a Polymer

In certain embodiments, a purified polymer of the disclosure, e.g., a polymer of Formula 4, a geometric isomer thereof, a tautomer thereof, or a salt thereof, can be used as a single or primary colorant by itself or in combination with another colorant (e.g., a dimer of formula 1A, 1B, 2, 3A, 3B, 2', 3'A, 3'B, 3'A (Me), 3'B (Me), or any combination thereof). In some embodiments, a purified polymer of the disclosure, e.g., a polymer of Formula 4, a geometric isomer thereof, a tautomer thereof, or a salt thereof, can be diluted by mixing the polymer with a diluent (e.g., water). In some embodiments, a purified polymer of the disclosure, e.g., a polymer of Formula 4, a geometric isomer thereof, a tautomer thereof, or a salt thereof, can be concentrated by removing a diluent (e.g., a solvent such as methanol, water, etc.) from a composition comprising the polymer and the diluent.

In some embodiments, a colorant composition comprises a polymer of Formula 4:

$$T^1\text{-}(\text{-A-}CH_2\text{---})_n\text{-}T^2 \qquad \text{Formula 4,}$$

a geometric isomer thereof, a tautomer thereof, or a salt thereof, wherein n is an integer from 2 to 200;

wherein each A is independently selected from the group consisting of formula 5A, formula 5B, formula 5C, a geometric isomer thereof, a tautomer thereof, a salt thereof, and a combination thereof:

Formula 5A

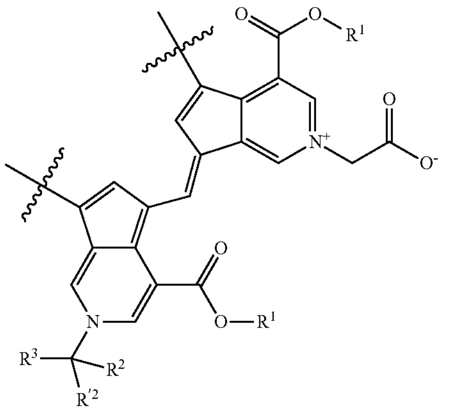

-continued

Formula 5B

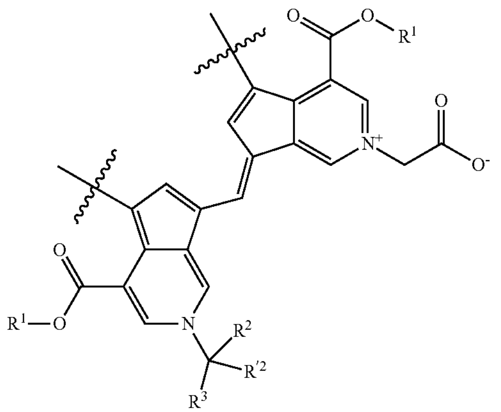

Formula 5C

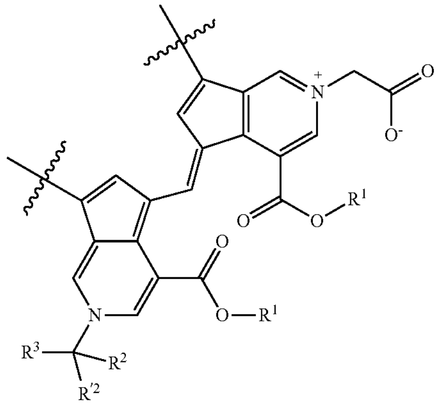

wherein:

$R^1$ is hydrogen, methyl, ethyl, propyl, isopropyl, butyl, sec-butyl, isobutyl, or tert-butyl;

$R^2$ and $R'^2$ are independently hydrogen, or $C_{1-10}$ alkyl;

$R^3$ is hydrogen or COOH;

and wherein $T^1$ is hydrogen or a methyl group; and $T^2$ is hydrogen or A-$T^1$, wherein A and $T^1$ are defined above;

wherein the colorant composition is substantially free of a first additional compound selected from the group consisting of formula 6, formula 7, formula 8, a geometric isomer thereof, a tautomer thereof, and a salt thereof:

Formula 6

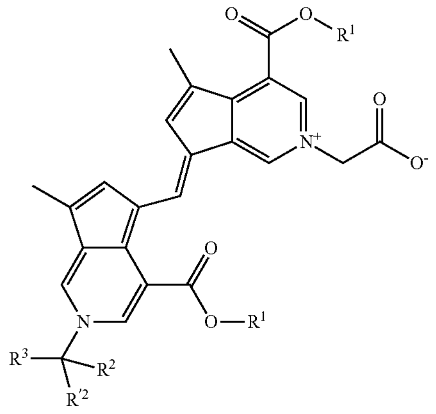

-continued

Formula 7

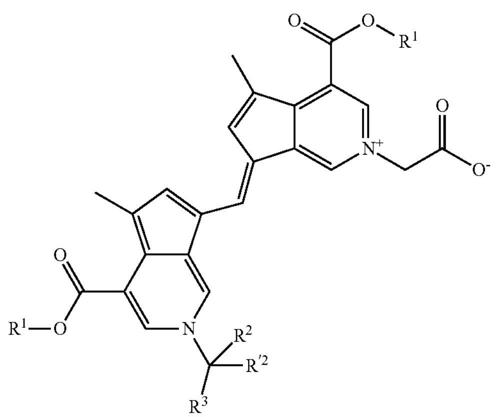

Formula 8

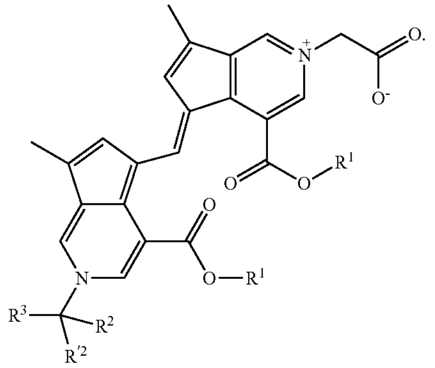

In some embodiments, $R^3$ is H. In some embodiments, $R^3$ is COOH.

In some embodiments, one of $R^2$ and $R'^2$ is hydrogen. In some embodiments, both $R^2$ and $R'^2$ is hydrogen. In some embodiments, one of $R^2$ and $R'^2$ is hydrogen; and the other of $R^2$ and $R'^2$ is an unsubstituted $C_{1-10}$ straight alkyl chain (e.g., methyl, ethyl, propyl, butyl, pentyl, hexyl, etc.), or an $C_{1-10}$ straight alkyl chain substituted with 1-3 methyl group, such as isopropyl, isobutyl, isopentyl, etc.

In some embodiments,

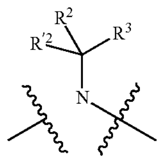

represents an amino acid residue ($R^3$ is COOH and $R^2$ and/or $R'^2$ represents the side chain(s)). In some embodiments, the amino acid residue is a residue of Glycine, Alanine, Valine, Leucine, Isoleucine, Serine, Cysteine, Threonine, Methionine, Proline, Phenylalanine, Tyrosine, Tryptophan, Histidine, Lysine, Arginine, Aspartate, Glutamate, Asparagine, taurine, carnitine, ornithine, citrulline, or Glutamine. In some embodiments, the amino acid residue is a residue of Glycine.

In some embodiments, $R^1$ can be hydrogen, methyl, ethyl, propyl, isopropyl, butyl, sec-butyl, isobutyl, or tert-butyl, for example, $R^1$ can be hydrogen, methyl, or ethyl; or $R^1$ can be methyl.

In some embodiments, $T^1$ can be hydrogen or methyl.

In some embodiments, n is from 2-200, 2-150, 2-100, 2-50, 2-25, 2-20, 2-15, 2-10, or 2-5.

In some embodiments, a colorant composition comprises a polymer of Formula 4:

$$T^1\text{-}(\text{-A-}CH_2\text{—})_n\text{-}T^2 \quad \text{Formula 4,}$$

a geometric isomer thereof, a tautomer thereof, or a salt thereof, wherein n is an integer from 2 to 20;

wherein each A is independently selected from the group consisting of formula 5'A, formula 5'B, formula 5'C, a geometric isomer thereof, a tautomer thereof, a salt thereof, and a combination thereof:

Formula 5'A

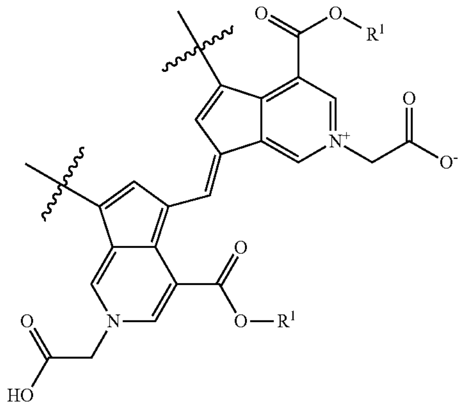

Formula 5'B

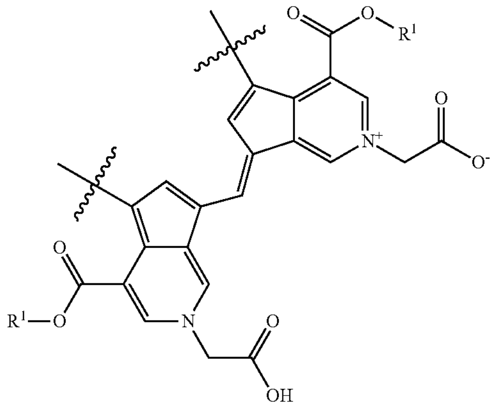

Formula 5'C

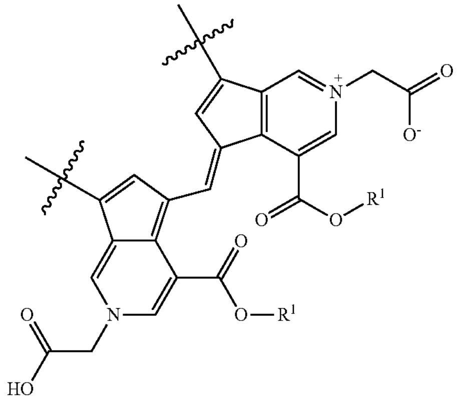

wherein:

$R^1$ is hydrogen, methyl, ethyl, propyl, isopropyl, butyl, sec-butyl, isobutyl, or tert-butyl;

and wherein $T^1$ is hydrogen or a methyl group; and $T^2$ is hydrogen or A-$T^1$, wherein A and $T^1$ are defined above;

wherein the colorant composition is substantially free of a first additional compound selected from the group consisting of formula 2', formula 3'A, formula 3'B, a geometric isomer thereof, a tautomer thereof, and a salt thereof:

Formula 2'

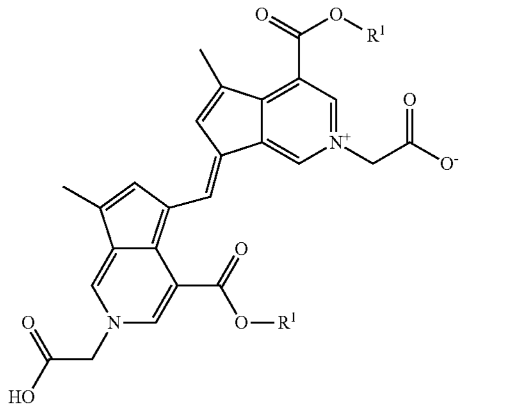

Formula 3'A

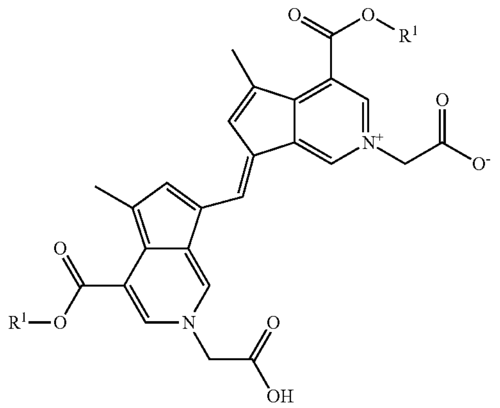

Formula 3'B

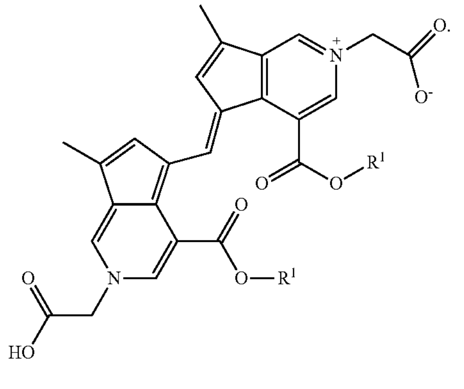

In some embodiments, $R^1$ is methyl.

In some embodiments, suitable polymers of Formula 4, a geometric isomer thereof, a tautomer thereof, or a salt thereof, have various repeating units (i.e., different "A" in Formula 4), various terminal groups (e.g., different $T^1$, $T^2$, or both), and/or various chain lengths. In another embodiment, suitable polymers of Formula 4, a geometric isomer thereof, a tautomer thereof, or a salt thereof, include those having characteristic UV-Vis absorption spectra (e.g., maximum absorption wavelength ($\lambda_{max}$), NMR spectra, IR spectra, average molecular weight (e.g., number average molecular weight ($M_n$)), or a combination thereof. In another embodiment, suitable polymers of Formula 4, a geometric isomer thereof, a tautomer thereof, or a salt thereof, include those having a certain levels of purity.

Polymer Structure

In some embodiments, each A of the polymer of Formula 4 is independently a formula 5'A, formula 5'B, formula 5'C, a geometric isomer thereof, a tautomer thereof, or a salt thereof. In some embodiments, each A in the polymer of Formula 4 is a formula 5'A, a geometric isomer thereof, a tautomer thereof, or a salt thereof. In some embodiments, each A in the polymer of Formula 4 is a formula 5'B, a geometric isomer thereof, a tautomer thereof, or a salt thereof. In some embodiments, each A in the polymer of Formula 4 is a formula 5'C, a geometric isomer thereof, a tautomer thereof, or a salt thereof. In other embodiments, the polymer of Formula 4 can include repeated units comprising both formula 5'A and formula 5'B, both formula 5'A and formula 5'C, both formula 5'B and formula 5'C, or formula 5'A, formula 5'B, and formula 5'C.

Polymers of Formula 4 with various $R^1$ groups (e.g., hydrogen, methyl, ethyl, propyl, isopropyl, butyl, sec-butyl, isobutyl, or tert-butyl) are useful as blue colorant compounds. In some embodiments, $R^1$ can be hydrogen, methyl, or ethyl. In some embodiments, each A in the polymer of Formula 4 is a formula 5'A, a geometric isomer thereof, a tautomer thereof, or a salt thereof, and $R^1$ in formula 5'A is hydrogen. In some embodiments, each A in the polymer of Formula 4 is a formula 5'A, a geometric isomer thereof, a tautomer thereof, or a salt thereof, and $R^1$ in formula 5'A is methyl. In some embodiments, each A in the polymer of Formula 4 is a formula 5'A, a geometric isomer thereof, a tautomer thereof, or a salt thereof, and $R^1$ in formula 5'A is ethyl. In some embodiments, each A in the polymer of Formula 4 is a formula 5'B, a geometric isomer thereof, a tautomer thereof, or a salt thereof, and $R^1$ in formula 5'B is hydrogen. In some embodiments, each A in the polymer of Formula 4 is a formula 5'B, a geometric isomer thereof, a tautomer thereof, or a salt thereof, and $R^1$ in formula 5'B is methyl. In some embodiments, each A in the polymer of Formula 4 is a formula 5'B, a geometric isomer thereof, a tautomer thereof, or a salt thereof, and $R^1$ in formula 5'B is ethyl. In some embodiments, each A in the polymer of Formula 4 is a formula 5'C, a geometric isomer thereof, a tautomer thereof, or a salt thereof, and $R^1$ in formula 5'C is hydrogen. In some embodiments, each A in the polymer of Formula 4 is a formula 5'C, a geometric isomer thereof, a tautomer thereof, or a salt thereof, and $R^1$ in formula 5'C is methyl. In some embodiments, each A in the polymer of Formula 4 is a formula 5'C, a geometric isomer thereof, a tautomer thereof, or a salt thereof, and $R^1$ in formula 5'C is ethyl.

The present disclosure also provides polymers of formula 4 with different terminal groups. In some embodiments, a suitable terminal group is any of those formed according to a reaction shown in Scheme 1. In some embodiments, $T^1$ is hydrogen or methyl group; and $T^2$ is hydrogen or A-$T^1$, wherein A and $T^1$ are described herein.

In some embodiments, purified polymers of formula 4, a geometric isomer thereof, a tautomer thereof, or a salt thereof, with varying degree of polymerization are suitable for the various uses disclosed in the present disclosure. In some embodiments, n in formula 4 is an integer from 2 to 20, from 2 to 18, from 2 to 16, from 2 to 14, from 2 to 12, from 2 to 10, from 2 to 8, from 2 to 6, from 2 to 4, from 4 to 20, from 4 to 18, from 4 to 16, from 4 to 14, from 4 to 12, from 4 to 10, from 4 to 8, from 4 to 6, from 6 to 20, from 6 to 18, from 6 to 16, from 6 to 14, from 6 to 12, from 6 to 10, from 6 to 8, from 8 to 20, from 8 to 18, from 8 to 16, from 8 to 14, from 8 to 12, from 8 to 10, from 10 to 20, from 10 to 18, from 10 to 16, from 10 to 14, or from 10 to 12. In some embodiments, where a purified polymer is a purified single chemical compound of general formula 4, then in formula 4 is 2, 3, 4, 5, 6, 7, 8, 9, 10, 11, 12, 13, 14, 15, 16, 17, 18, 19, or 20.

Characteristics of Polymer

In certain embodiments, polymers, e.g., a polymer of Formula 4, a geometric isomer thereof, a tautomer thereof, or a salt thereof, having certain characteristics are suitable for use in a colorant composition.

In some embodiments, the polymer has a maximum absorption wavelength ($\lambda_{max}$) in the range of about 580 to about 610 nm in a UV-Vis spectrum. In some embodiments, the polymer has a maximum absorption wavelength ($\lambda_{max}$) of about 580, about 585, about 590, about 595, about 600, about 605, or about 610 nm. In some embodiments, the polymer has a maximum absorption wavelength ($\lambda_{max}$) of less than about 580 nm (e.g., about 570, about 560 nm, etc.). In some embodiments, the polymer has a maximum absorption wavelength ($\lambda_{max}$) of greater than about 610 nm (e.g., about 620, about 630 nm, etc.).

In some embodiments, the polymer is characterized by having a HPLC retention time of about 10.3 minutes, e.g., when analyzed by the method described in Example 6. In some embodiments, the polymer is characterized by having a stronger absorption at 590 nm compared to absorption at 240 nm. In some embodiments, the polymer is characterized by having a HPLC trace substantially identical to the spectrum of FIG. 13C.

In certain embodiments, polymers of formula 4, a geometric isomer thereof, a tautomer thereof, or a salt thereof, having different average molecular weight are suitable for use in a colorant composition. In some embodiments, the polymer has an average molecular weight in the range of about 1000 to about 20,000. In some embodiments, the polymer has an average molecular weight in the range of about 3000 to about 15,000, or about 3000 to about 10,000. In some embodiments, the polymer has an average molecular weight in the range of about 4,500 to about 7,500. In some embodiments, the polymer has an average molecular weight of about 5000, about 5500, about 6000, about 6500, or about 7000. In some embodiments, the polymer has an average molecular weight of about 6000. In some embodiments, the average molecular weight is a number average molecular weight ($M_n$). In some embodiments, the average molecular weight is a weight average molecular weight ($M_w$). In some embodiments, the average molecular weight is any average molecular weight known in the art, such as a viscosity average molecular weight ($M_v$), a Z average molecular weight ($M_z$), etc. Methods for measuring and/or calculating average molecular weight (e.g., $M_n$, $M_w$, $M_v$, or $M_z$) are known in the art.

Figure 12:
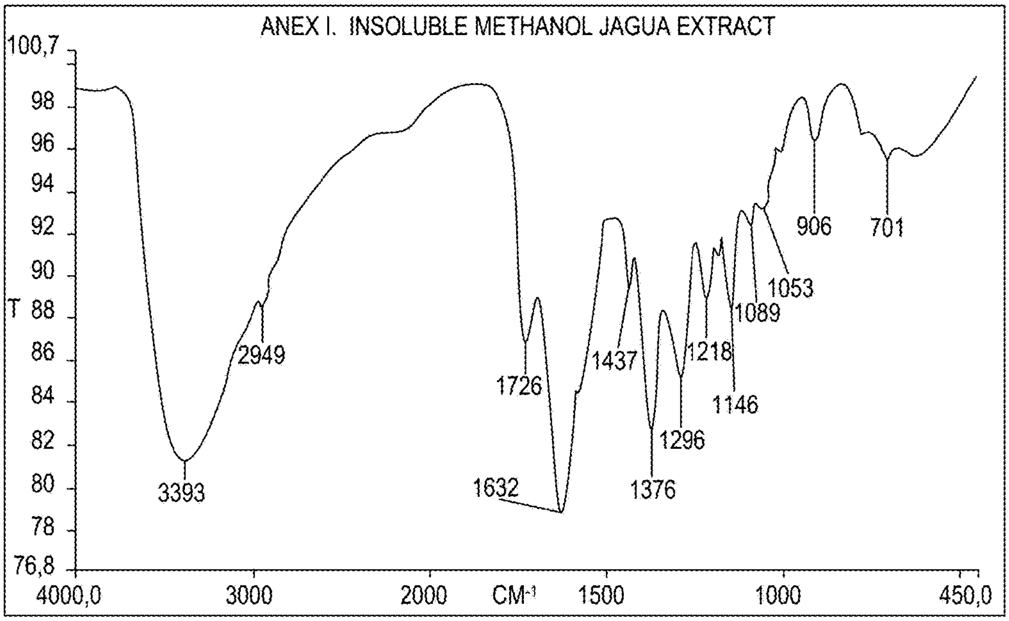
FIG. 12 shows the IR profile of an isolated polymer from a reaction of genipin and glycine.

In certain embodiments, polymers having a specified IR absorption are suitable for use in a colorant composition. In some embodiments, the polymer is characterized by an IR spectrum having the following peaks (±5 $cm^{-1}$): 3393, 2949, 1726, 1630, and 1540 $cm^{-1}$. In some embodiments, the polymer is characterized by having an IR spectrum substantially identical to the spectrum shown in FIG. 12. In some embodiments, the polymer is characterized by an IR spectrum having the following peaks (±5 $cm^{-1}$): 3393, 2949, 1726, 1630, and 1540 $cm^{-1}$, or having an IR spectrum substantially identical to the spectrum shown in FIG. 12.

Figure 9:
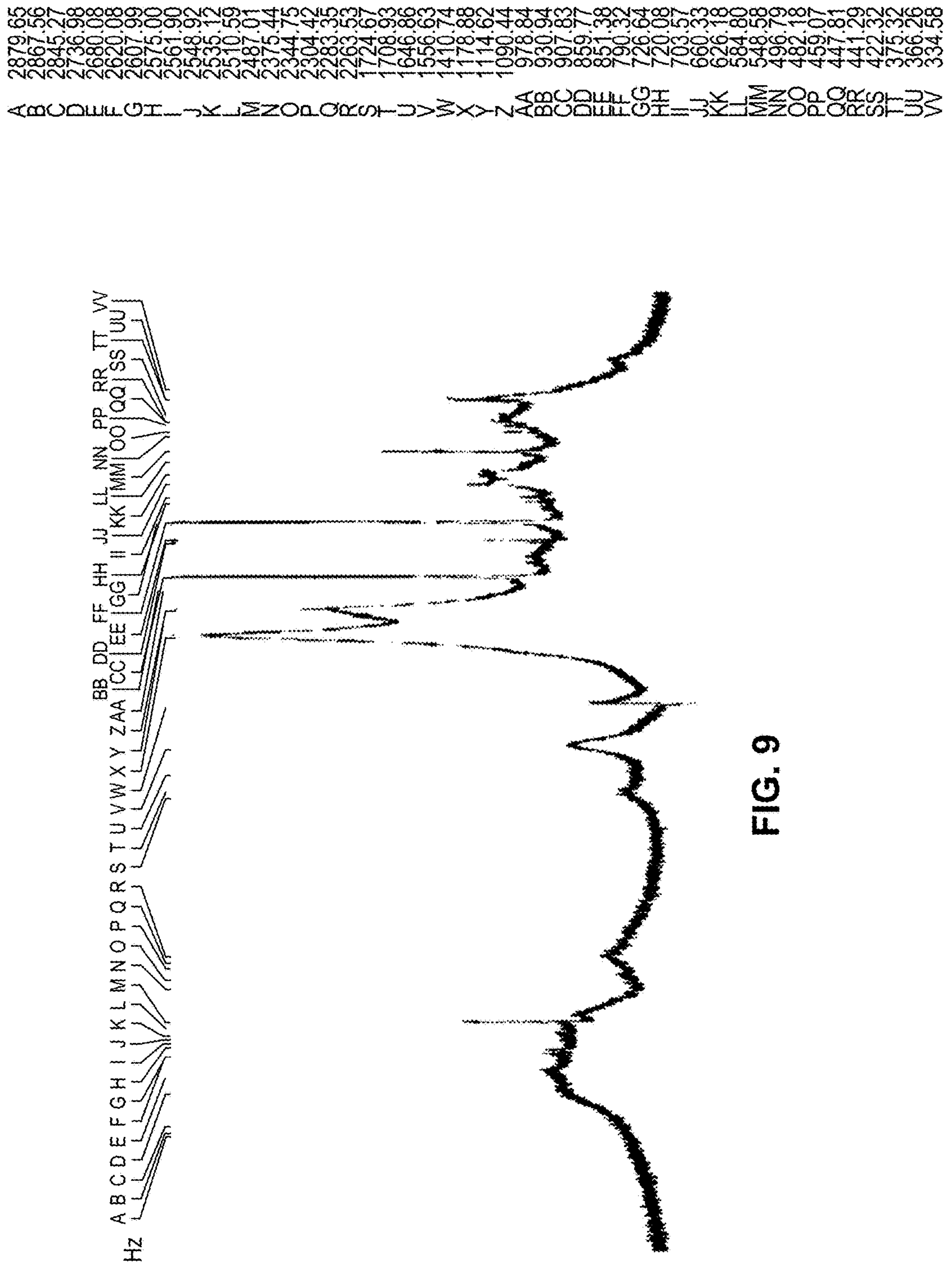
FIG. 9 shows a NMR spectrum for insoluble fraction isolated from a reaction of genipin and glycine.

$^1$H NMR is another spectroscopic method for characterizing a polymer. In some embodiments, the polymer has $^1$H NMR as shown in FIG. 9. In some embodiments, the colorant composition comprises a polymer, wherein the $^1$H NMR of the polymer is substantially identical to the spectrum in FIG. 9. In some embodiments, the polymer has a $^1$H NMR substantially identical to the spectrum in FIG. 9 and/or an IR spectrum substantially identical to the spectrum in FIG. 12.

Mass Spectrometry is yet another method for characterizing a polymer. In some embodiments, the polymers having a MS fragments having a m/e of 701 and/or 475 are used in blue colorant compositions. In some embodiments, the colorant composition comprises a polymer characterized by having a MS fragment (m/e) of 701 or 475. In some embodiments, the polymer is characterized by having MS fragments (m/e) of 701 and 405. In some embodiments, the MS fragments (m/e) 701 and 405 correspond to formula 9, left and right, respectively.

Formula 9

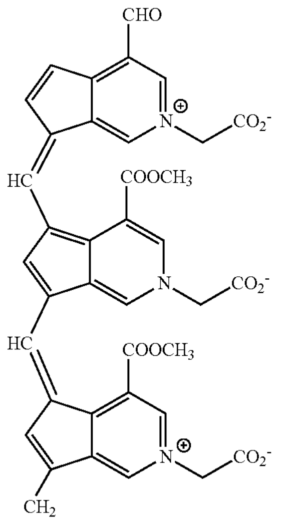

$C_{38}H_{27}N_3O_{11}$
701.1645

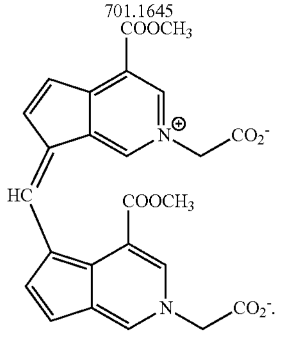

$C_{25}H_{19}N_2O_8$
475.1141

Figure 11:
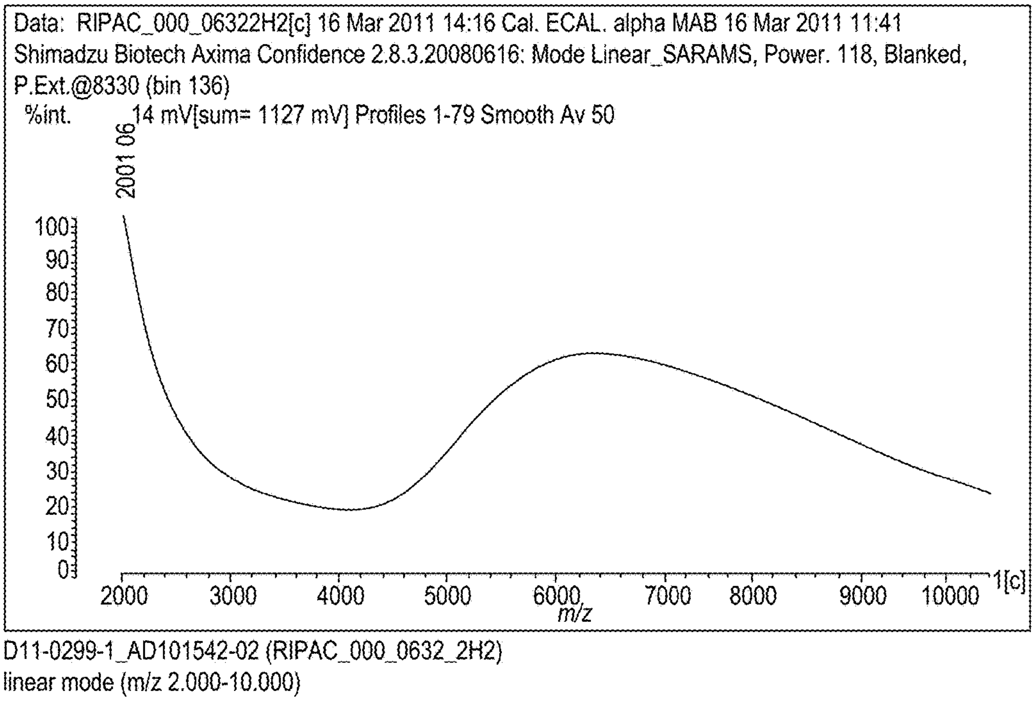
FIG. 11 shows the mass profile obtained by selective molecular weight filtration of an isolated polymer from a reaction of genipin and glycine.

In some embodiments, the polymer is characterized by having MS fragments (m/e) of 701 and 405 also has a substantially identical $^1$H NMR compared to the spectrum in FIG. 9. In some embodiments, the polymer is further characterized by an IR spectrum substantially identical to the spectrum in FIG. 12. In some embodiments, the polymer is characterized by having a mass profile substantially identical to those shown in FIG. 11. In some embodiments, the colorant composition is substantially free of a first additional compound of formula 6, 7, or 8.

Purity of Polymer

In certain embodiments, suitable polymers include, e.g., those described herein with certain levels of purity. In some embodiments, the colorant composition comprises a polymer of formula 4, wherein the colorant composition is substantially free of a first additional compound selected from the group consisting of formula 6, formula 7, formula 8, a geometric isomer thereof, a tautomer thereof, and a salt thereof. In some embodiments, the colorant composition is substantially free of a first additional compound selected from the group consisting of formula 2', formula 3'A, formula 3'B, a geometric isomer thereof, a tautomer thereof, and a salt thereof. In some embodiments, the colorant composition is substantially free of a first additional compound selected from the group consisting of formula 2, formula 3'A (Me), formula 3'B (Me), a geometric isomer thereof, a tautomer thereof, and a salt thereof:

Formula 2

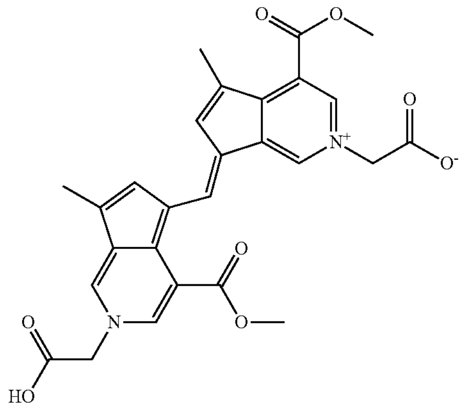

Formula 3'A (Me)

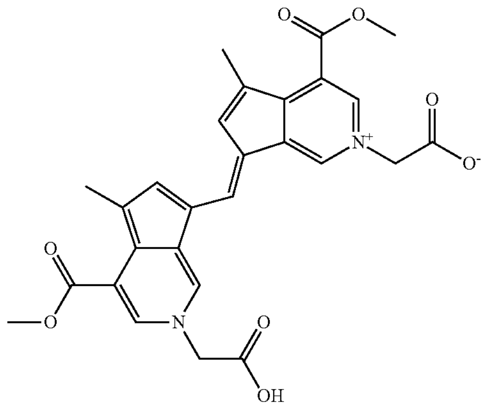

Formula 3'B (Me)

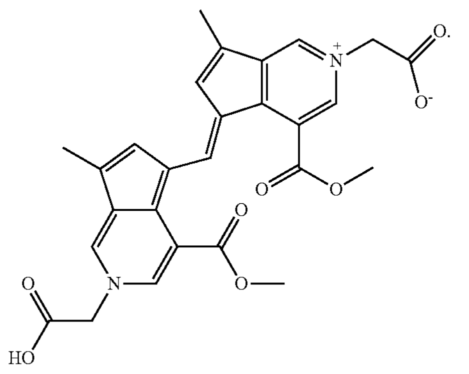

In some embodiments, total weight of the first additional compound is less than 4.5%, less than 4%, less than 3%, less than 2%, less than 1%, less than 0.5%, less than 0.1%, or less than 0.01% by weight of the polymer. In some embodiments, total weight of the first additional compound is less than 1% by weight of the polymer. In some embodiments, total weight of the first additional compound is less than 0.1% by weight of the polymer. In other embodiments, total weight of the first additional compound is less than 0.01% by weight of the polymer. In some embodiments, the colorant composition is free of the first additional compound. In some embodiments, total weight of the first additional compound is 0.01-5%, 0.01-4.5%, 0.01-4%, 0.01-3%, 0.01-2%, 0.01-1%, 0.01-0.5%, or 0.01-0.1% by weight of the polymer.

In some embodiments, the colorant composition comprises a polymer of formula 4, wherein the colorant composition is substantially free of a second additional compound selected from the group consisting of formula 1A, formula 1B, a geometric isomer thereof, a tautomer thereof, and a salt thereof:

Formula 1A

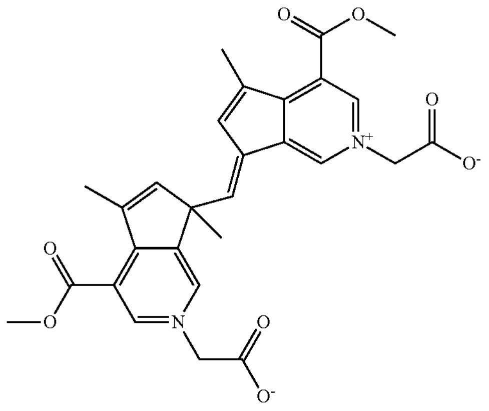

Formula 1B

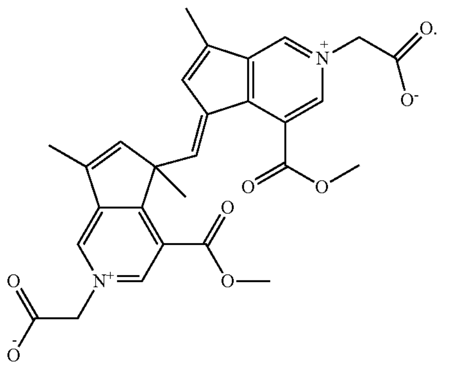

In some embodiments, total weight of the second additional compound is less than 1% by weight of the polymer. In some embodiments, total weight of the second additional compound is less than 0.1% by weight of the polymer. In other embodiments, total weight of the second additional compound is less than 0.01% by weight of the polymer. In some embodiments, the colorant composition is free of the second additional compound. In some embodiments, total weight of the second additional compound is 0.01-5%, 0.01-4.5%, 0.01-4%, 0.01-3%, 0.01-2%, 0.01-1%, 0.01-0.5%, or 0.01-0.1% by weight of the polymer.

In some embodiments, the colorant composition substantially free of a first additional compound is further substantially free of a second additional compound. Suitable weight percentages of the first or second additional compound to that of the polymer are described herein. In some embodiments, combined weight of a first and second additional compound is less than 5% (e.g., less than 4.5%, less than 4%, less than 3%, less than 2%, less than 1%, less than 0.5%, less than 0.1%, less than 0.01%) by weight of the polymer. In some embodiments, the colorant composition is free of the first and second additional compound. In some embodiments, total weight of the first and second additional compound is 0.01-5%, 0.01-4.5%, 0.01-4%, 0.01-3%, 0.01-2%, 0.01-1%, 0.01-0.5%, or 0.01-0.1% by weight of the polymer.

In some embodiments, the colorant composition comprises a polymer of formula 4 substantially free of compounds, other than the polymer, having a maximum absorption wavelength ($\lambda_{max}$) in the range of 580-610 nm. In some embodiments, total weight of the compounds, other than the polymer, having a maximum absorption wavelength ($\lambda_{max}$) in the range of 580-610 nm is less than 5% (e.g., less than 4.5%, less than 4%, less than 3%, less than 2%, less than 1%, less than 0.5%, less than 0.1%, less than 0.01%) by weight of the polymer. In some embodiments, the colorant composition is free of compounds, other than the polymer, having a maximum absorption wavelength ($\lambda_{max}$) in the range of 580-610 nm. In some embodiments, total weight of the compounds, other than the polymer, having a maximum absorption wavelength ($\lambda_{max}$) in the range of 580-610 nm, is 0.01-5%, 0.01-4.5%, 0.01-4%, 0.01-3%, 0.01-2%, 0.01-1%, 0.01-0.5%, or 0.01-0.1% by weight of the polymer.

Certain embodiments are directed to a substantially purified polymer of Formula 4, a geometric isomer thereof, a tautomer thereof, or a salt thereof.

In some embodiments, the substantially purified polymer comprises:

$$T^1\text{-}(\text{-A-CH}_2\text{---})_n\text{-}T^2 \quad \text{Formula 4,}$$

a geometric isomer thereof, a tautomer thereof, or a salt thereof, wherein n is an integer from 2 to 20;

wherein each A is of formula 5'A (Me), a geometric isomer thereof, a tautomer thereof, or a salt thereof:

Formula 5'A (Me)

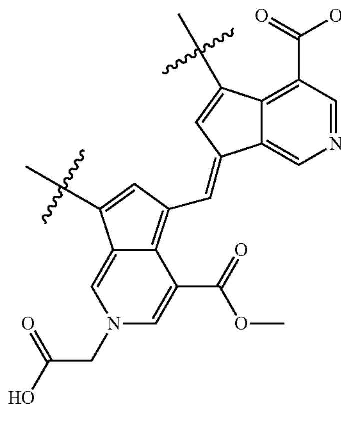

wherein $T^1$ is hydrogen or a methyl group; and $T^2$ is hydrogen or A-$T^1$, wherein A and $T^1$ are defined above. In some embodiments, the substantially purified polymer is characterized by having an average molecular weight described herein (e.g., having a number average molecular weight ($M_n$) of about 6,000). In some embodiments, the substantially purified polymer is characterized by having an IR spectrum described herein (e.g., an IR spectrum having the following peaks (±5 $cm^{-1}$): 3393, 2949, 1726, 1630, and 1540 $cm^{-1}$). In some embodiments, the colorant composition comprises a polymer of Formula 4, wherein the colorant composition is free of or substantially free of carbohydrates, e.g., sugars. In some embodiments, the colorant composition is free of carbohydrates and at least 80%, 85%, 90%, 95%, 99%, or 100% free of other impurities, e.g., monomers, dimers, fatty acids, fat, proteins or organic acids.

Method of Preparing Purified Polymer

In certain embodiments, polymers of the present disclosure are prepared by reacting a genipin derivative (e.g., genipin) with an amine (e.g., glycine) as disclosed in Scheme 1. In some embodiments, purified polymers are obtained by purifying the reaction mixture from a genipin derivative (e.g., genipin) and an amine (e.g., glycine) as disclosed in Scheme 1.

In some embodiments, the polymer is prepared by reacting genipin with an amine.

In some embodiments, the polymer is prepared by reacting genipin with a primary alkyl amine (e.g., methyl amine, ethyl amine, propyl amine, or other $C_{1-10}$ primary amines). In some embodiments, the polymer is prepared by reacting genipin with a secondary alkyl amine (e.g., isopropyl amine, or other $C_{1-10}$ secondary amines). In some embodiments, the polymer is prepared by reacting genipin with an amino acid (e.g., glycine, alanine, valine, leucine, isoleucine, lysine, tyrosine, methionine, proline, phenylalanine, etc.). In some embodiments, the polymer is prepared by reacting genipin with glycine.

In some embodiments, the genipin is a purified genipin, or a juice containing genipin. In some embodiments, the polymer of the present disclosure is a product formed by a reaction of a purified genipin (e.g., more than 80%, 85%, 90%, 95%, or 99% by weight) and glycine. In some embodiments, the polymer of the present disclosure is a purified product obtained from a reaction of glycine and a juice containing genipin. In some embodiments, the juice containing genipin is a fruit juice. In some embodiments, the fruit juice is derived from *Genipa americana*.

In some embodiments, the glycine is a purified glycine. In some embodiments, the glycine is a mixture containing glycine (e.g., a juice containing glycine, or a dry mix containing glycine such as a juice concentrate containing glycine). In some embodiments, the glycine is a juice containing glycine (e.g., a fruit juice such as a juice derived from watermelon, white grape, pineapple, lychee, cantaloupe, banana, orange, apple, pear, lemon, passion fruit, red grape, blueberry, tamarind, peach, papaya, acai, plum, guava, tangerine, borojo, cupuacu, goji, or kiwi). In some embodiments, the glycine is a juice containing glycine, wherein the juice is derived from watermelon. In some embodiments, the glycine is a juice containing glycine, wherein the juice is derived from fresh watermelon.

In some embodiments, the polymer are derived from a reaction of a juice derived from watermelon and genipin. In some embodiments, the polymer are derived from a reaction of a juice derived from watermelon and a juice derived from *Genipa americana*. In some embodiments, the polymer are derived from a reaction of a juice derived from watermelon and a purified genipin (e.g., more than 80%, 85%, 90%, 95%, or 99% by weight).

Certain embodiments are directed to a method of isolating polymers from a reaction mixture of genipin and an amine.

In some embodiments, the method comprises (a) extracting a blue mixture derived from a reaction of genipin and an amine with a solvent (e.g., methanol) to produce a soluble fraction and an insoluble fraction; and (b) purifying the insoluble fraction. In some embodiments, the purifying step (b) comprises subjecting the insoluble fraction to a HPLC purification.

Certain embodiments are directed to a method of isolating polymers from a reaction mixture of genipin and glycine. In some embodiments, the method comprises (a) extracting a blue mixture derived from a reaction of genipin and glycine with methanol to produce a methanol-soluble fraction and a methanol-insoluble fraction; and (b) purifying the methanol-insoluble fraction. In some embodiments, the blue mixture is derived from a reaction of purified genipin (e.g., more than 80%, 85%, 90%, 95%, or 99% by weight) and glycine. In some embodiments, the blue mixture is derived from a reaction of glycine and a juice derived from *Genipa americana*. In some embodiments, the blue mixture is a dry powder (e.g., a lyophilized powder) derived from the reaction of genipin and glycine. In some embodiments, the purifying step comprises subjecting the insoluble fraction to a HPLC purification. In some embodiments, the HPLC purification is a reverse phase HPLC purification. In some embodiments, the purifying step (b) is similar to a purification step disclosed in the Examples section. In some embodiments, the purification method provides a purified polymer as described herein.

In some embodiments, a colorant product is produced by the methods described herein. In some embodiments, the colorant product is produced by (a) extracting a blue mixture derived from a reaction of genipin and glycine with methanol to produce a methanol-soluble fraction and a methanol-insoluble fraction; and (b) purifying the methanol-insoluble fraction to obtain the colorant product. In some embodiments, the blue mixture is a dry powder (e.g., a lyophilized powder) derived from the reaction of genipin and glycine. In some embodiments, the colorant product is substantially free of any compound of Formula 6, 7, or 8 disclosed herein. In some embodiments, the colorant product can be characterized by having (a) a substantially identical NMR spectrum as that shown in FIG. 9; (b) an IR spectrum having the following peaks (±5 $cm^{-1}$): 3393, 2949, 1726, 1630, and 1540 $cm^{-1}$; (c) an average molecular weight (e.g., a number average molecular weight (MO) of about 6,000; (d) a MS spectrum showing MS fragments of 701 and/or 475; or (e) any combination of (a)-(d).

Colorant Composition Substantially Free of Carbohydrates

Certain embodiments are directed to a colorant composition comprising a purified polymer (e.g., a polymer of formula 4), wherein the colorant composition is substantially free of carbohydrates (e.g., monosaccharides, disaccharides, oligosaccharides, or polysaccharides). In some embodiments, the carbohydrate is a sugar (e.g., monosaccharides and disaccharides). In some embodiments, the colorant composition substantially free of carbohydrates is also substantially free of other impurities (e.g., a dimer of formula 1A, 1B, 2, 3A, or 3B). In some embodiments, the colorant composition is free of carbohydrates, e.g., the colorant composition contains no carbohydrates that can be detected, e.g., by the method described in Example 7. The terms "carbohydrate" and "sugar" are used interchangeably herein unless otherwise differentiated.

In some embodiments, the colorant composition free of or substantially free of carbohydrates includes compositions that have additional materials other than the purified polymer, e.g., monomers, dimers, fatty acids, fat, proteins, or organic acids. In some embodiments, the colorant composition free of or substantially free of carbohydrates further comprises an additional compound (e.g., a dimer of formula 1A, 1B, 2, 3A, or 3B, an additional colorant (e.g., a FDA approved color additive)). In some embodiments, the colorant composition free of or substantially free of carbohydrates is also free of or substantially free of, e.g., monomers, dimers (e.g., a dimer of formula 1A, 1B, 2, 3A, or 3B), an additional colorant (e.g., a FDA approved color additive), fatty acids, fat, proteins, or organic acids. In some embodiments, the colorant composition free of or substantially free of carbohydrates is prepared by a process comprising mixing a purified polymer substantially free of carbohydrates with an additional compound (e.g., a dimer of formula 1A, 1B, 2, 3A, or 3B, an additional colorant (e.g., a FDA approved color additive)) that is substantially free of carbohydrates.

In some embodiments, the purified polymer is derived from a reaction of genipin and glycine. In some embodiments, the purified polymer is derived from a reaction of purified genipin (e.g., more than 80%, 85%, 90%, 95%, or 99% by weight) and glycine. In some embodiments, the purified genipin is derived from *Genipa americana*. In some embodiments, the purified polymer is derived from a reaction of a juice containing genipin and glycine. In some embodiments, the purified polymer is derived from a reaction of a fruit juice (e.g., a juice derived from *Genipa americana*, a genipin enriched juice derived from *Genipa americana*)) and glycine. In some embodiments, the purified polymer is derived from a reaction of genipin and a juice (e.g., a fruit juice such as watermelon juice and others as described herein) containing glycine.

In some embodiments, the purified polymer is characterized by having a HPLC retention time of about 10.3 minutes when analyzed, e.g., by the method described in Example 6. In some embodiments, the purified polymer is characterized by having a stronger absorption at 590 nm compared to absorption at 240 nm. In some embodiments, the purified polymer is characterized by having a HPLC trace substantially identical to the spectrum of FIG. 13C.

Figure 13A:
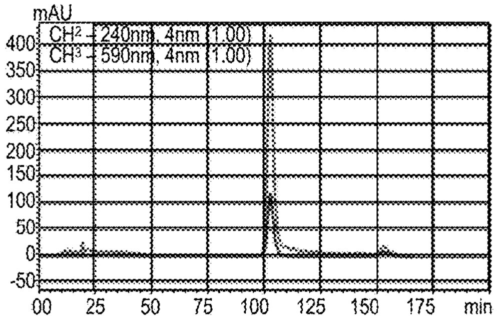
FIGS. 13A-D show high-performance liquid chromatography (HPLC) traces of four samples (A, B, C, and D) containing blue polymer from a reaction of *Genipa americana* juice and glycine. A) pink line 240 nm, blue line 590 nm with lower absorbance; B) almost equal absorbances at 240 and 590 nm; C) bigger absorbance at 590 nm; and D) raw batch with carrier.
Figure 13B:
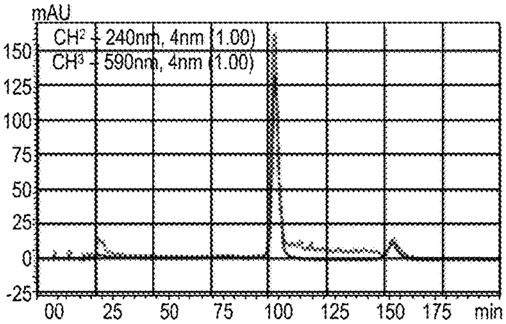

Certain embodiments are directed to a method of preparing a colorant composition substantially free of carbohydrates. In some embodiments, the method comprises purifying a crude colorant composition with column chromatography (e.g., size exclusion column chromatography, reverse phase HPLC etc.); analyzing fractions for the presence of carbohydrates (e.g., by thin layer chromatography); and collecting fractions that are substantially free of carbohydrates. In some embodiments, the crude colorant composition is derived from a reaction of genipin (e.g., a purified genipin, a juice derived from *Genipa americana*, a genipin enriched juice, a genipin enriched juice derived from *Genipa americana*) and glycine. In some embodiments, the method produces a colorant composition having a HPLC trace substantially identical to the spectrum of FIG. 13A, 13B, or 13C. In some embodiments, the method produces a colorant composition having a HPLC trace substantially identical to the spectrum of FIG. 13C.

Certain embodiments are directed to a method of preparing a colorant composition free of sugar. In some embodiments, the method comprises (a) mixing *Genipa americana* juice and an amino acid selected from the group consisting of glycine, valine, lysine, methionine, proline, tyrosine, tryptophan, and any combination thereof (b) removing sugar from the mixture of (a); and (c) isolating a colorant composition from the sugar-free product of (b), wherein the intensity of the colorant composition obtained by the method is greater than, e.g., at least twice, the intensity of a colorant composition obtained from the mixture of steps (a) without removing sugar. In some embodiments, the intensity of the colorant composition is measured by UV-vis absorbance at a certain wavelength (e.g., at $\lambda_{max}$ of the colorant composition, at a wavelength in the range of 580-610 nm, at a wavelength of 590 nm, etc.). In some embodiments, the polymer content is a percentage % (g/100 g sample) and determined by HPLC measurement and the color intensity is determined using an spectrophotometer (e.g., 0.6 absorbance valor). In some embodiments, the method comprises removing sugar (e.g., from the reaction mixture of *Genipa americana* juice and an amino acid (e.g., glycine, valine, lysine, methionine, proline, tyrosine, tryptophan, or any combination thereof)) by fermentation, column chromatography (e.g., size exclusion chromatography, HPLC), reverse osmosis filtration, ultrafiltration, microfiltration, dialysis (e.g., dialysis methods using osmotic gradients), resin mediated separation (e.g., XAD4, XAD7, or XAD8 resin mediated separation), or any combination thereof. In certain embodiments, the microbiological stability of the fermented products is improved by eliminating sugar content, which, e.g., can easily generate mesophilic microbial agents, such as fungi and yeasts.

In some embodiments, the method comprises removing sugar by fermentation. In some embodiments, the fermentation is carried out with yeast (e.g., natural yeast, genetically modified yeasts, such as those with increased efficiency in sugar degradation) or bacteria (including genetically modified bacteria that have increased efficiency in sugar degradation). In some embodiments, the yeast or bacteria is immobilized (e.g., attached to a solid support; encapsulated with micro capsules).

In some embodiments, a method of preparing a colorant composition comprises (a) mixing *Genipa americana* juice and an amino acid selected from the group consisting of glycine, valine, lysine, methionine, proline, tyrosine, tryptophan, and any combination thereof; (b) sterilizing the mixture of step (a); (c) inoculating the sterilized mixture of step (b) with a yeast or a bacteria; (d) incubating the inoculated mixture of step (c) under fermentation conditions to produce a fermentation product; and (e) isolating a colorant composition from the fermentation product of claim (d), wherein the intensity of the colorant composition obtained by the method is greater than, e.g., at least twice, the intensity of a colorant composition obtained from the mixture of steps (a) without fermentation.

In some embodiments, the incubation of step (d) is at least 6 hours (e.g., 6-24, 6-18, 6-12, 6-9, 9-24, 9-18, 9-12, 12-24, 12-18, or more than 24 hours). In some embodiments, the incubation of step (d) is less than 6 hours (e.g., 6, 5, 4, 3, 2, 1, 0.5 hours). Certain embodiments are directed to a method of quantifying a polymer in a sample comprising using a HPLC method with the polymer in a pure form as an external reference. In some embodiments, the polymer is the blue polymer derived from a reaction of genipin and glycine. In some embodiments, the polymer in a pure form as an external reference is substantially free of carbohydrates. In some embodiments, the polymer in a pure form as an external reference is characterized by having an HPLC trace substantially identical to the spectrum of FIG. 13C.

Methods for Producing Colorant Compositions

Certain embodiments are directed to a method of preparing a colorant composition. In some embodiments, a method of preparing of a colorant composition comprises (a) isolating juice from *Genipa americana* fruit; (b) mixing the juice and a first amino acid selected from the group consisting of glycine (GLY), valine (VAL), lysine (LYS), proline (PRO), methionine (MET), tyrosine (TYR), and tryptophan (TRP) and a second amino acid selected from the group consisting of glycine (GLY), valine (VAL), lysine (LYS), proline (PRO), methionine (MET), tyrosine (TYR), and tryptophan (TRP); (c) after (b), isolating a colorant composition. Certain embodiments are directed to colorant compositions comprising a product formed by reacting juice from *Genipa americana* fruit with an amino acid combination, e.g., glycine and methionine. In certain embodiments, fresh fruits are used within one or two days of harvesting (e.g., within about 0-6, 0-12, 0-18, 0-24, 0-36, or 0-48 hours). In other embodiments, fruits are used after storage under refrigeration conditions are used within 1.5 weeks (e.g., within about 1, 2, 3, 4, 5, 6, 7, 8, 9, 10, 11, or 12 days) or within 2 weeks (e.g., within about 1, 2, 3, 4, 5, 6, 7, 8, 9, 10, 11, 12, 13, or 14 days). In another embodiment the fruit is unripe, e.g., fruit that is hard and has uniform skin in contrast to ripe fruit that is soft and has irregular skin. In some embodiments, the colorant composition is blue, blue green, green, purple, red, or black.

In some embodiments, a method of preparing of a colorant composition comprises (a) mixing genipin or a genipin derivative with a first amino acid selected from the group consisting of glycine (GLY), valine (VAL), lysine (LYS), proline (PRO), methionine (MET), tyrosine (TYR), or tryptophan (TRP) and a second amino acid selected from the group consisting of glycine (GLY), valine (VAL), lysine (LYS), proline (PRO), methionine (MET), tyrosine (TYR), or tryptophan (TRP) and isolating a colorant composition formed therefrom. Certain embodiments are directed to colorant compositions comprising a product formed by reacting genipin or a genipin derivative with an amino acid combination, e.g., glycine and methionine. In some embodiments, the colorant composition is blue, blue green, green, purple, red, or black.

Purple Colorant Compositions

The unripe fruits of *Genipa americana* are a source of genipin, an iridoid metabolite that reacts with amines to give blue coloured products. In *Genipa americana* fruits (Jagua), genipin is found in endocarps (pulp) and the rest of the fruit is discarded. Jagua mesocarps (peel) material is discarded because of its low content of genipin.

Certain embodiments are directed to a method of preparing a purple colorant composition. In some embodiments, a method of preparing of a purple colorant composition comprises (a) isolating mesocarps from *Genipa americana* fruit; (b) preparing a juice extract from the mesocarps; (c) mixing the juice extract and glycine; (d) after (c), heating the mixture of juice and glycine; and (e) isolating a purple colorant composition after (d). In some embodiments, the heating in step (d) is at least 90 minutes (e.g., 90 minutes to about 3, 4, 5, or 6 hours, or more than 6 hours). As used herein, "mesocarps" refer to the peel of the fruit, e.g., *Genipa americana* fruit. In certain embodiments, fresh fruits are used within one or two days of harvesting (e.g., within about 0-6, 0-12, 0-18, 0-24, 0-36, or 0-48 hours). In other embodiments, fruits are used after storage under refrigeration conditions are used within 1.5 weeks (e.g., within about 1, 2, 3, 4, 5, 6, 7, 8, 9, 10, 11, or 12 days) or 2 weeks (e.g., within about 1, 2, 3, 4, 5, 6, 7, 8, 9, 10, 11, 12, 13, or 14 days). In another embodiment the fruit is unripe, e.g., fruit that is hard and has uniform skin in contrast to ripe fruit that is soft and has irregular skin.

Certain embodiments are directed to colorant compositions comprising a product formed by reacting an aqueous extract containing a genipin derivative with an amine (e.g. an amino acid such as glycine, valine, proline, lysine, tryptophan, tyrosine, or methionine). In some embodiments, the aqueous extract containing a genipin derivative is prepared by a method comprising (a) isolating mesocarps from *Genipa americana* fruit; and (b) extracting the mesocarps with water. In some embodiments, the colorant composition is a purple colorant composition comprising a product formed by the aqueous extract of mesocarps from *Genipa americana* fruit and glycine. In some embodiments, the aqueous extract has less than 20%, 15%, 10%, 5%, 3%, 2%, 1%, 0.5%, or 0.1% by AUC (area under the curve in an HPLC spectrum) of genipin. In some embodiments, the amino acid is glycine. In some embodiments, the product is formed by mixing the aqueous extract of mesocarps from *Genipa americana* fruit with glycine, and then heating the mixture, wherein the aqueous extract is not preheated. In some embodiments, the colorant composition comprises a genipin precursor comprising a (+)-Geniposide or irodoid B-glycoside precursor of genipin, which is derived from the mesocarps (peel) from *Genipa americana* fruit.

Geniposide is the glycoside of genipin. Geniposide has different kinetics and chemical properties from genipin. Glucose is part of the geniposide structure.

Glucose is present in *Genipa americana* juice in the pulp (endocarps) as free glucose. However, genipin is found in the endocarp, which produces a blue colorant when reacted with glycine. Reacting glycine with the geniposide from the mesocarps resulted in a purple colorant.

Certain embodiments are directed to a method of preparing of a colorant composition comprising (a) isolating mesocarps from *Genipa americana* fruit; (b) isolating geniposide from the mesocarps; (c) mixing the geniposide and amino acid selected from the group consisting of glycine (GLY), valine (VAL), lysine (LYS), proline (PRO), methionine (MET), tyrosine (TYR), tryptophan (TRP), or any combination thereof; and (d) isolating a colorant composition after (c). In some embodiments, the geniposide is stabilized by freeze drying or flash freezing. In some embodiments, the colorant composition is purple.

Green and Black Colorant Compositions

Certain embodiments are directed to a method of preparing a green or black colorant composition. The reaction of *Genipa americana* juice with different amino acids produced different color products, e.g., blue (GLY and LYS), blue green (VAL, MET and TYR), green (TRP) and black (PRO). Some embodiments are directed to a method of preparing of a black colorant composition comprising (a) preparing a juice extract from *Genipa americana* fruit; (c) mixing the juice extract and proline; and (e) isolating a black colorant composition from (c). Some embodiments are directed to a method of preparing of a green colorant composition comprising (a) preparing a juice extract from *Genipa americana* fruit; (c) mixing the juice extract and tryptophan; and (e) isolating a green colorant composition from (c).

Use of Colorant Compositions Comprising a Polymer and/or a Dimer

Certain embodiments are directed to use of a purified polymer (e.g., a polymer of Formula 4, a geometric isomer thereof, a tautomer thereof, or a salt thereof, or a polymer (e.g., a polymer derived from a reaction of genipin and glycine) substantially free of carbohydrates) or a purified dimer (e.g., a substantially pure compound No. 1, 2, 3, or a substantially pure compound of Formula 1A, 1B, 2, 3'A (Me), 3'B (Me), or a combination thereof) to impart a blue color to a substrate (e.g., a food item, a cosmetic, a drug or nutraceutical product, a textile product, or a device such as a medical device).

In some embodiments, the method of imparting a blue color to a substrate (e.g., a food item, a cosmetic, a drug or nutraceutical product, a textile product, a device such as a medical device) comprises contacting the substrate with a colorant composition comprising a purified polymer (e.g., a polymer of Formula 4, a geometric isomer thereof, a tautomer thereof, or a salt thereof, or a polymer (e.g., a polymer derived from a reaction of genipin and glycine) substantially free of carbohydrates) or a purified dimer (e.g., a substantially pure compound No. 1, 2, 3, or a substantially pure compound of Formula 1A, 1B, 2, 3'A (Me), 3'B (Me)), a colorant composition described herein, or any combination thereof. In some embodiments, the colorant composition comprises a polymer of Formula 4, a geometric isomer thereof, a tautomer thereof, or a salt thereof. In some embodiments, the colorant composition comprises a dimer. In some embodiments, the dimer is a substantially purified compound of formula 1A, 1B, 2, 3'A (Me), or 3'B (Me). In some embodiments, the colorant composition is prepared by a process of mixing a compound of Formula 1A, 1B, 2, 3'A (Me), or 3'B (Me) with any of the polymers disclosed herein. In some embodiments, the colorant composition is prepared by mixing a polymer or a dimer disclosed herein with a color additive (e.g. a FDA approved color additive). In some embodiments, the substrate is a food item. In some embodiments, the substrate is a medical device. In some embodiments, the substrate is a drug product. In some embodiments, the substrate is a nutraceutical product. In some embodiments, the substrate is a cosmetic product.

Certain embodiments are directed to a food product comprising a food item and a colorant composition disclosed herein (e.g., a colorant composition comprising a purified polymer disclosed herein, or a colorant composition comprising a purified dimer disclosed herein). The food item can be a solid food item or a liquid food item. In some embodiments, the food item is a dairy product, a bakery product, a soft drink, a confectionery (e.g., candy, or cereal bars, etc.), or a beverage. In some embodiments, the food item is a beverage. In some embodiments, the food item is a carbonated beverage. In some embodiments, the food item is for human consumption. In some embodiments, the food item is a veterinary food item, such as a pet food item (e.g. a cat food, a dog food, etc.) or a farm animal food item (e.g., a cow food). In some embodiments, the food item is a plant food item, such as a fertilizer. In some embodiments, the food item is a unit dosage food item, such as a unit dosage yoghourt, pudding, soup, etc.

Certain embodiments are directed to a drug product comprising a drug (e.g. a FDA approved drug) and a colorant composition disclosed herein (e.g., a colorant composition comprising a purified polymer disclosed herein, or a colorant composition comprising a purified dimer disclosed herein). In some embodiments, the drug is in a liquid dosage form. In some embodiment, the drug is in a solid dosage form. In some embodiments, the drug is in a dosage form selected from the group consisting of tablets, gel caps, beads, pellets, pills, dragees, lozenges, ointments, capsules, powders, liquids, gels, syrups, slurries, and suspensions. In some embodiments, the drug is in a form of a syrup.

Certain embodiments are directed to a nutraceutical product (e.g. vitamins, vitamin supplements, or dietary mixes and packets) comprising a nutraceutical and a colorant composition disclosed herein (e.g., a colorant composition comprising a purified polymer disclosed herein, or a colorant composition comprising a purified dimer disclosed herein). In some embodiments, the nutraceutical is in a liquid dosage form. In some embodiment, the nutraceutical is in a solid dosage form. In some embodiments, the nutraceutical is in a dosage form selected from the group consisting of tablets, gel caps, beads, pellets, pills, dragees, lozenges, ointments, capsules, powders, liquids, gels, syrups, slurries, and suspensions. In some embodiments, the nutraceutical is in a form of a tablet, or a gel cap.

Certain embodiments are directed to a cosmetic product comprising a cosmetic and a colorant composition disclosed herein (e.g., a colorant composition comprising a purified polymer disclosed herein, or a colorant composition comprising a purified dimer disclosed herein). In some embodiments, the cosmetic is a bath product, such as shower gels, bath gels, or a soap. In some embodiments, the cosmetic can be a product for eye and facial makeup, nail polishes, lipsticks, or tattoos. In some embodiments, the cosmetic can be a product for oral care (e.g., mouthwashes, tooth gels, or toothpaste). In some embodiments, the cosmetic can be a product for skin care (e.g., skin conditioners, gels (e.g., a hand gel), lotions and creams, or masks). In some embodiments, the cosmetic can be a product for shaving (e.g., shaving cream). In some embodiments, the cosmetic can be a product for hair care (e.g., hair coloring products).

Certain embodiments are directed to a medical device colored by a colorant composition disclosed herein (e.g., a colorant composition comprising a purified polymer disclosed herein, or a colorant composition comprising a purified dimer disclosed herein). In some embodiments, the medical device is a surgical device (e.g., surgical threads, scissors, gloves etc.).

Certain embodiments are directed to a textile product colored by a colorant composition disclosed herein.

In certain embodiments, the amount of a colorant composition to be incorporated into a food product, a cosmetic product, a drug product, a medical device, or a textile product depends on the final color to be achieved. In some embodiments, the food product, the cosmetic product, the drug product, the medical device, or the textile product comprises a colorant composition disclosed herein in an effective amount, by itself or with another colorant, to impart the food product, the cosmetic product, the drug product, or the medical device a color selected from the group consisting of light blue, Air Force blue, air superiority blue, Alice blue, azure, baby blue, Bley de France, blue, blue-gray, Bondi blue, Brandeis blue, Cambridge blue, Carolina blue, celeste, cerulean, Cobalt blue, Columbia blue, cornflower blue, Cyan, dark blue, deep sky blue, denim, Dodger blue, Duke blue, Egyptian blue, electric blue, Eton blue, Glaucous blue, electric indigo, indigo, international Klein blue, iris, light blue, majorelle blue, maya blue, medium blue, midnight blue, navy blue, non-photo blue, Oxford blue, Palatinate blue, Periwinkle, Persian blue, Phthalo blue, Powder blue, Prussian blue, Royal blue, Sapphire Sky blue, Steel blue, Teal, Tiffany Blue, True Blue, Tufts Blue, Turquoise, UCLA Blue, Ultramarine, Violet-Blue, Yale Blue, and Zaffre. The effectiveness of the colorant composition can be determined by comparing (e.g., by visual comparison) a color to be achieved (e.g., a light blue) with the product or device colored with an amount of the colorant composition.

Although the description presents preferred embodiments of the present invention, additional changes may be made in the form and disposition of the parts without deviating from the ideas and basic principles encompassed by the claims.

EXAMPLES

Example 1. Genipin Isolation from *Genipa americana* Juice

A solid lyophilized (freeze dried) (900 grams) from 10 liters of *Genipa americana* green juice was Soxhlet extracted with dichloromethane; the generated solvent was evaporated under reduced pressure resulting in a brown residue (240 g); an aliquot of 1 g was separated by exclusion chromatography by size using, as mobile phase, a mix of hexane/methanol/dichloromethane (2:2:1) from which there were four resulting fractions; genipin was identified in one of the fractions using fine layer chromatography and by comparing with a previously know genipin patter. The fraction containing the genipin was purified multiple times with a chromatographic silica gel column and a hexane/ethyl acetate mobile phase until a pure product (200 mg of genipin) was obtained according to NMR spectra.

Example 2. Reaction of Genipin and Glycine

Glycine (2 g) dissolved in water (200 mL) was heated a 70°. Then, genipin (5 g) in methanol (10 mL) was added and the mix was stirred for four hours. The reaction mix was lyophilized (freeze dry) and the blue powder was extracted with ethyl-acetate in order to eliminate genipin excess and other low polar components.

Example 3. Fractioning of Components

The blue powder (5.7 g) was extracted with methanol (5×100 mL), the generated solvent was evaporated under reduced pressure and a blue resin (2.2 g) was obtained. The blue resin dissolved in methanol 90% was separated in a Sephadex® LH 20 (methanol mobile phase) resulting in four fractions which were denominated (for purposes of this patent Application) S1 (1.5 g), S2 (0.3 g), S3 (100 mg) and S4 (5 mg).

The S1 fraction was separated using an adsorption resin (Amberlite® XAD-7) using initially 15% ethanol and ending with pure water. Three fractions were separated with identical IR and NMR spectra. The three fractions were combined and determined to be a polymer.

Figure 5:
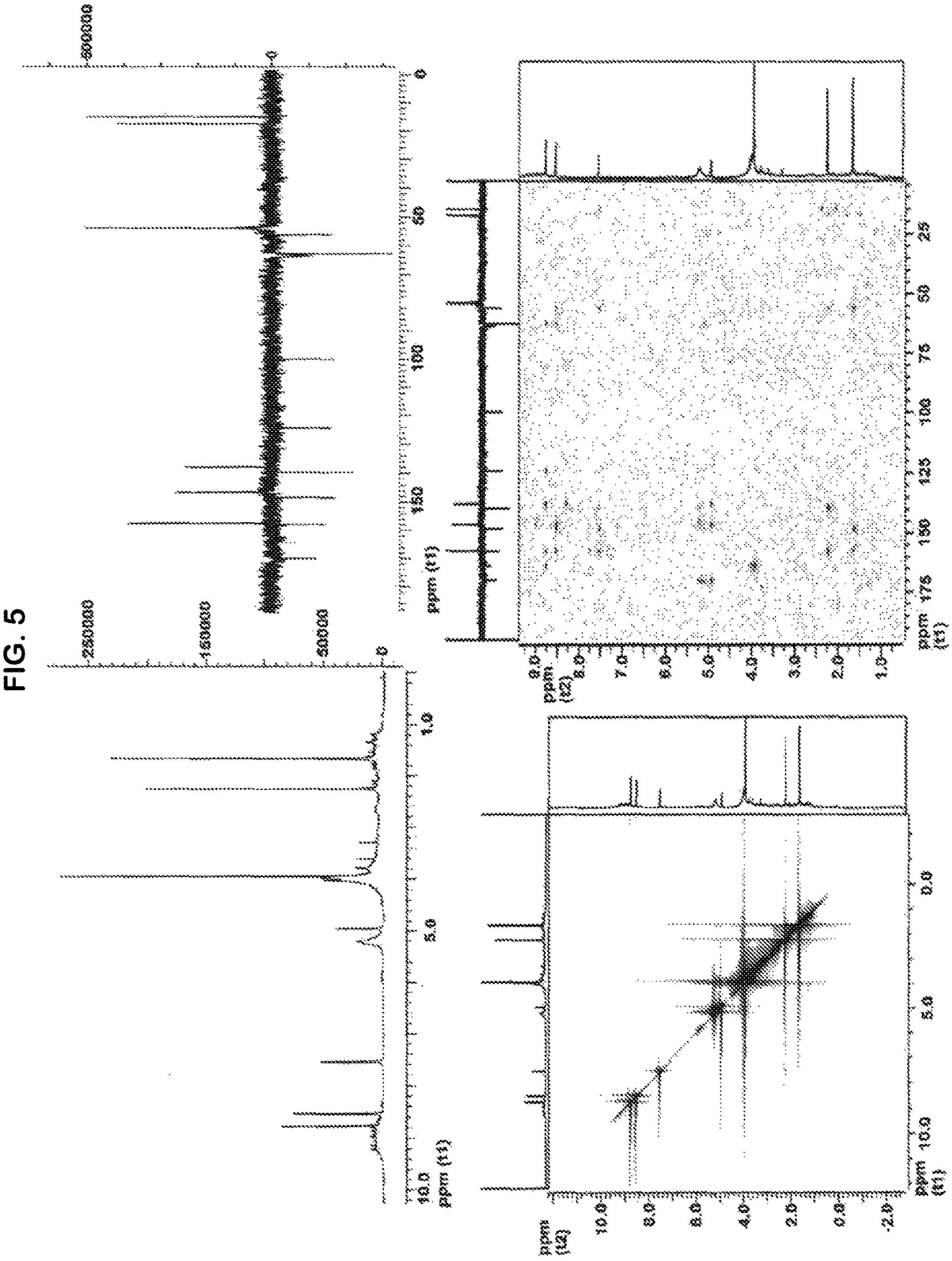
FIG. 5 shows a nuclear magnetic resonance (NMR) spectroscopy spectra of a compound 1 isolated from a reaction of genipin and glycine.

The S2 fraction was separated using an adsorption resin (Amberlite® XAD-7) using initially 15% ethanol and ending with 95% ethanol. Four sub-fractions were generated from S2. These S2 sub-fractions were denominated (for purposes of this patent Application) M2S1R, M2S2R, M2S3R and M2S4R. The M2S1R was RP-C18 separated several times with different mobile phases (mixes of ethanol-water and methanol-water) until a two compound were obtained, one of those two compounds was denominated compound No. 1 (7 mg). Spectroscopic characteristics of compound No. 1 (FIG. 5) are:

$^1$H NMR (400 MHz, $D_2O$). δ 8.77, 8.53, 7.54, 5.30-4.95, 3.94, 2.25, 1.66 ppm.

$^{13}$C NMR (100 MHz). δ 170.0, 164.16, 157.80, 157.44, 148.29, 146.41, 139.76, 137.83, 124.16, 63.35, 62.6, 56.19, 53.89, 17.43, 14.93 ppm.

Further analysis of compound No. 1 showed that:

In $^1$H NMR displayed a few signals: two aromatic protons as singlets at δ 8.77 and 8.53, a vinylic proton at 7.54, a singlet at 4.95, (2H) and three singlets integrating for 3H each one at 3.94 ($OCH_3$), 2.25 (vinylic methyl group), and 1.66.

The JMOD experiment displayed the following signals: three methyl groups at 14.93, 17.43 and 53.89, one methylene at 62.68, assignable to a methylene derived from glycine, three methine at 157.44, 146.41, 137.83 and finally, seven quaternary carbon atoms at 170.00 (carboxylic), 164.16 (methyl ester carbonyl), 157.80, 148.29, 139.76, 124.16 and 53.89. So, the genipin moiety and glycine residue has been conserved, but molecule now is aromatic with a pyridil residue, due to position of the protons and carbons atoms in NMR spectra. However, a new methyl group appeared in the structure and its position was assignable on the basis of JMOD, HMQC and HMBC experiments. So, COSY 1H-1H showed an allylic connectivity between methyl group at 2.25 with vinylic proton at 7.54; in the HMBC experiment this proton displayed 3J coupling to these methyl (157.44 in 13C NMR) and the aliphatic methyl group at 14.93 (1.66 in $^1$H NMR), which in turn, establish a correlation to the quaternary carbon atom at 53.89 and aromatic at 157.80 and 148.29. Other long range connectivities detected were: N—CH2 (62.68) to both aromatic protons at 8.77 and 8.53, and the former to methylester carbonyl. Finally, MS exhibited a m/z 522 [$M^+$+H] indicating a symmetric dimeric molecule, as can be seen in FIGS. 1A-1B and 2A-2B. The connecting bridge between monomers was deduced through C-8 and C-8' carbon atoms, since apparition of a methyl group as a singlet, which is mutually coupled to the other methyl group in the HMBC experiment. There are two possible isomers, such as having a formula 1A or 1B (see FIGS. 1A, 1B, 2A, and 2B).

The S3 fraction was separated by chromatography with Sephadex® using a 95% methanol mobile phase generating four S3 fractions that for the purpose of this patent Application were denominated S31, S32, S33, and S34. The S33 fraction was separated several times by RP-C18 reverse chromatography using different mobile phases (mixes of ethanol-water and methanol-water) until a compound, which was denominated compound No. 3 (4 mg) was obtained. The Spectroscopic characteristics of compound No. 3 (FIG. 6) are:

$^1$H NMR (400 MHz, $D_2O$). δ 8.6, 8.0, 7.9, 6.7, 3.90, 1.8 ppm.

$^{13}$C NMR (100 MHz). δ 172.2, 166.3, 138.8, 135.6, 135.1, 133.3, 131.4, 127.1, 120.46, 118.9, 61.0, 53.3, 11.2 ppm.

m/z 505 [M+H]

Further analysis of compound No. 3 showed that:

The mass spectra of the compound 3 displayed m/z=505 $[M+H]^+$ in mass spectrometry, so indicating an isomer of the compound previously described. However, the $^1$H and $^{13}$CNM spectra were very different to that one. In the proton spectra, the following singlets were detected: δ 8.0, δ 7.9, and δ 6.7 (2H each one) and one additional singlet at δ 8.6 integrating for 1H. Other signals were a singlet at δ 4.7 (N—CH2) and two methyl groups at δ 3.9 ($OCH_3$) and δ 1.8 ($CH_3$ vinyl. According to JMOD experiment, the following carbon atoms were observed too: a carboxyl group at δ 172.2, a methyl ester at δ 166.3, (COOH), five quaternary carbon atoms at δ 138.8, δ 135.1, δ 127.1, δ 120.4, δ 118.9, four methines at δ 135.6, δ 133.3, δ 131.4, δ 131.4, one methylene (N—$CH_2$) at δ 61.0 and two methyl groups at δ 53.3 ($OCH_3$) and δ 11.2 ($CH_3$ vinyl). The structure of each monomer unit was assigned according to HMBC experiment: signals at δ 7.9 and δ 8.0 were assigned to protons of the pyridil group, since a long range correlation to the N-methylene group at δ 61.0 was detected; additionally the last proton display $^3$J coupling to the methyl ester carbonyl at δ 172.2. Besides other important coupling was shown between the singlet at δ 131.4 (C-7) with protons of the methyl group. The low amounts of aromatic and vinyl proton indicated the presence of a symmetric dimeric molecule such as is showed in FIGS. 3A-3B. Two structures could be assigned to this molecule, according to the relative orientation of the methylester group (FIGS. 3A-3B), but structure B has a low probability due to steric hindrance.

Example 4. Purification of Methanol Insoluble Fraction

The insoluble methanol components were separated using Sephadex LH-20, eluting with MeOH-water and sub-fractions i1 (3.1 g) and i2 (100 mg) were collected. Subfraction i2 was separated using repeated RP-C18 column, eluting with MeOH/water to obtain pure Compound No. 2 (25 mg). Compound 2 was shown to have the structure of Formula 2.

Figure 8:
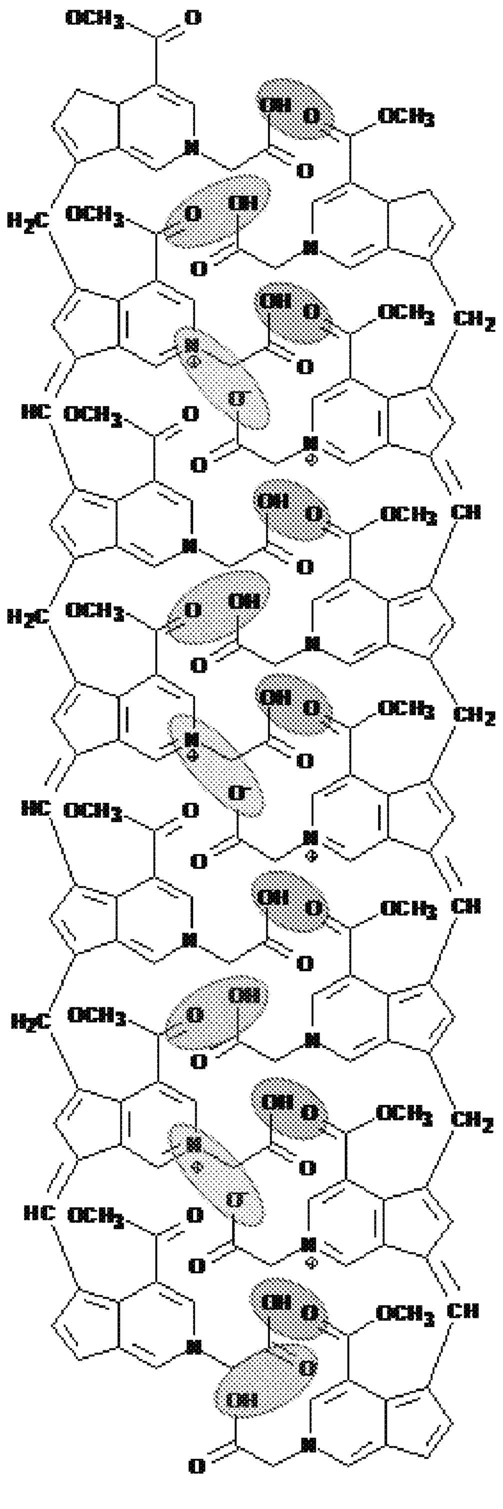
FIG. 8 is a schematic drawing of a polymer structure having Formula 4.

Sub-fraction 11 was separated into two main fractions using a RP-C18 column. The two fractions however have the identical IR and NMR spectra and are combined to yield a purified polymer. A schematic structure of the purified polymer is shown in FIG. 8.

NMR, IR and Mass spectroscopy analysis of the purified polymer show:

The IR spectra (FIG. 12) showed bands assignable to carboxylic acid (3393 $cm^{-1}$), aliphatic CH (2949), ester (1726) and aromatic pyridinium system (1630, 1540).

The $^1$H and $^{13}$C NMR fingerprint of small blue molecules, specifically dimers isolated and identified previously, and genipin, was constructed. The $^1$H NMR (FIG. 9) displayed the following signals: δ 9.50 (double bond bridge proton), δ 8.00-9.00 (aromatic pyridine derivatives or conjugated double bonds), δ 5.0-7.0 (double bond in cyclopentane ring), δ 5.0-4.5 ($CH_2$ attached to quaternary nitrogen), δ 3.8-4.1 ($OCH_3$), δ 1.5-2.3 ($CH_3$). The $^{13}$C NMR displayed signals at δ 160-175 (carboxylic and ester groups), δ 150.0-120.0 (aromatic and/or double bonds), δ 60.0-62.0 ($CH_2$ attached to quaternary nitrogen), δ 50.0-55.0 ($OCH_3$), δ 42.0-48.0 ($CH_2$) and finally δ 10.0-15.0 ($CH_3$).

Figure 10:
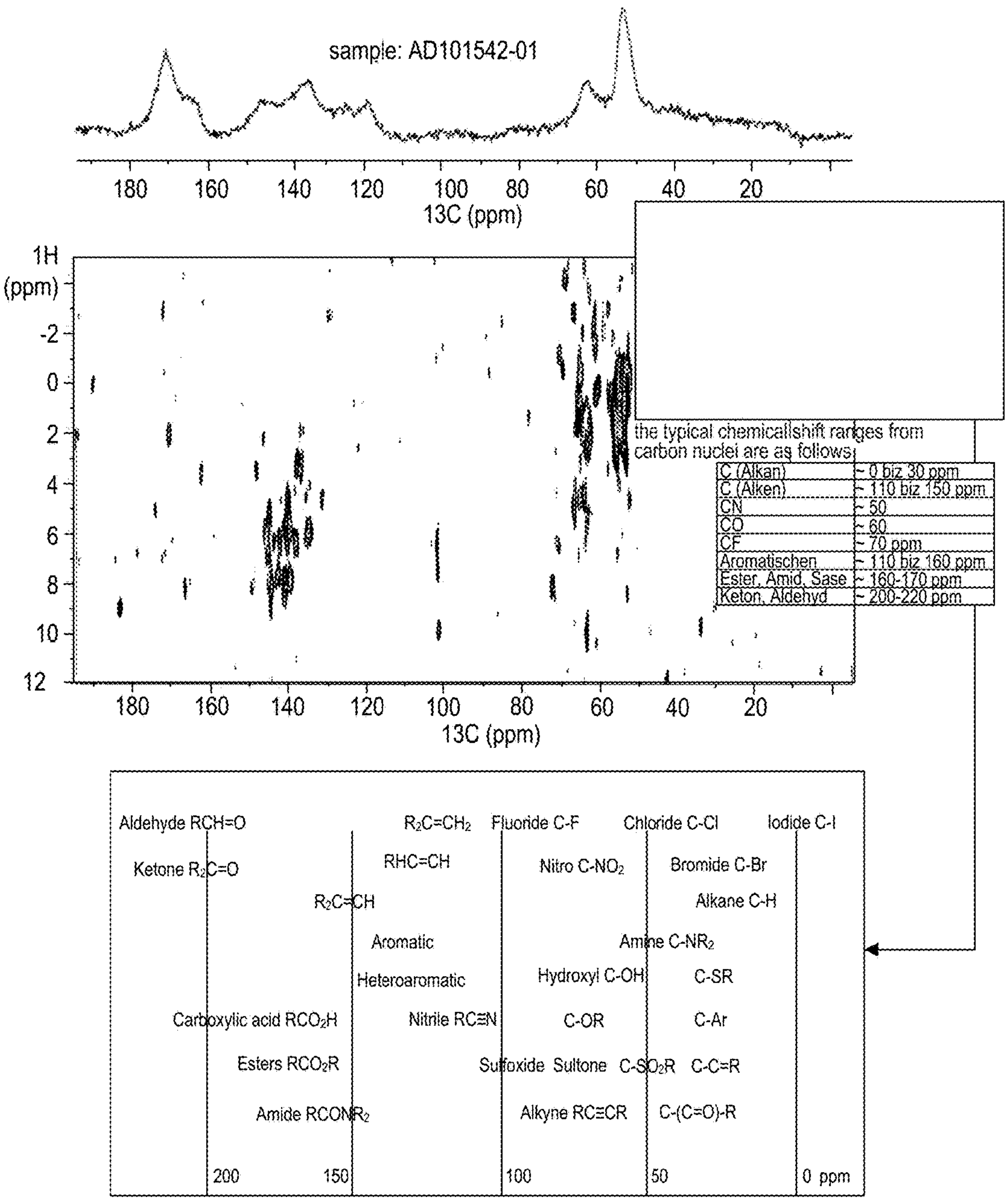
FIG. 10 shows a $^{1}H$-$^{13}C$ solid NMR spectrum of an isolated polymer from a reaction of genipin and glycine.

Subsequently, a solid state $^1$H-$^{13}$C NMR spectra (FIG. 10) was obtained and characteristic band or peaks were detected: carbonyl, aromatic, double bonds, N-methylene, methoxy, and methylene groups. Methyl groups or exocyclic methylene signals were absent, indicating the participation of an original exocycle methylene (or hydromethyl group) in the polymerization process.

The HPLC/MALDI analysis showed the purified polymer have a molecular weight of about 6000, about 12 units of a dimer. MS fragments corresponding to m/e of 701 and 475 were observed, see structure shown in formula 9.

Example 5. Reaction of *Genipa americana* Juice and Glycine

The raw liquid juice (100 mL) was mixed with glycine (0.8 g, the amount of glycine may be adjusted depending on the genipin content of the raw liquid juice so that the molar ratio of glycine and genipin is about 1:1) and the reaction temperature was maintained at 70° C. for 2 hours. After that, the solvent was evaporated and reduced pressure, or lyophilized to yield a dark blue powder mixture.

The dark blue powder was then extracted first with ethyl acetate and then more exhaustively with methanol. The soluble component in methanol (800 mg) was separated by column chromatography using Sephadex LH-20, and methanol. In the first fraction, the majority of the deep blue product (600 mg) was obtained as a purified polymer after evaporation of methanol. Small amounts of compounds 1 (1 mg), compound 2 (1.5 mg) and compound 3 (1 mg) were also obtained from the methanol soluble fraction.

The methanol insoluble fraction (1.2 g) was also separated using a Sephadex LH-20 column, eluting with methanol:water (9:1). Afterwards, a reverse phase C-18 separation was carried out to yield a purified polymer. The purified polymer from the methanol insoluble fraction was combined with the purified polymer from the methanol soluble fraction to yield 1.8 grams of polymer in total. Analytical data of the polymer obtained by reacting *Genipa americana* juice and Glycine are identical to those obtained from reacting purified genipin with glycine.

Example 6. Quantification of Polymer

A HPLC/PDA method was developed in order to evaluate the purity of the blue polymer and to quantify its content in Jagua Extract (obtained from reaction of *Genipa americana* juice and Glycine).

A Shimadzu Prominence UFLC with an online degasser (DGU-20 A5), a quaternary pump (LC 20AT), an auto sampler (SIL 20A HT), a column oven (CTO 20A), and a photodiode array detector (SPD M20A) controlled by a communication bus module (CBM 20A) was used for this analytical studies.

Several columns were used, such as reverse phase Luna C18 (Phenomenex) 150×4.6 mm 5 μm, supelcosil (Sigma) C8, 150×4.6 mm 5 μm, and Luna PFP 150×4.6 mm 5 μm.

The highly polar nature of the polymer in the Jagua extract limited the use of normal phase columns.

Acetonitrile and methanol were used in a number of ratios ranging from 100% to 100% water.

A flow rate of 1 mL/min was used and no modifications were done through the development process.

A PDA detector was used and wavelengths were monitored from 200 to 800 nm in max plot mode and at 590 nm to detect the blue polymer.

Although several columns and detector cell temperatures were evaluated, the best results were obtained using the Luna PFP column. The results from the analysis carried out with other columns were not satisfactory since only unretained peaks were observed regardless of the solvent mixture, column and detector temperature, flow speed or injection volume were used.

After column selection the solvent gradient was evaluated, the best results in separation were obtained with methanol and water as eluents but the peak shape and width needed to be improved at this stage, several trials with different column oven temperatures allowed to have a good shape and width without an effect on retention time.

A summary of the best separation conditions included the following:

Column Luna PFP 100A (Phenomenex) with security guard cartridge:

| | |
|---|---|
| Length | 150 mm |
| Internal Diameter | 4.6 mm |
| Particle size | 5 μm. |

Mobile phase: Eluent A: Water and Eluent B: Methanol

Linear Gradient:

| Linear Gradient (minutes) | % A | % B |
|---|---|---|
| 0 | 80 | 20 |
| 5 | 80 | 20 |
| 6 | 0 | 100 |
| 10 | 0 | 100 |
| 11 | 80 | 20 |
| 20 | 80 | 20 |

Flow rate: 1 mL/min

Temperatures:

$T_{Samples}$: Ambient (20-24° C.)

$T_{Column}$: 40° C.

$T_{Detector\ cell}$: 40° C.

Detection: Maxplot 230-800 nm (Extract profile); Maxplot 590 nm (quantification of blue polymer).

Sample Preparation: In a 10 or 25 mL volumetric flask; weigh 10 mg of the batch sample to be analyzed and complete volume with deionized water. 10 μL of this solution is injected using an auto sampler.

System Performance: In the standard method blue polymer was eluted at 10.3 minutes.

Example 7. Purification of Blue Polymer Free of Sugars

The blue polymer free of sugars was purified by column chromatography using Sephadex LH-20.

10 g of freeze-dried Jagua extract (obtained from reaction of *Genipa americana* juice and Glycine) were dissolved in 10 mL of deionized water and filtered. Afterwards the solution of the colorant was applied to the top of the column. The mobile phase composition was 100% methanol, 80% methanol, 50% methanol and 100% water. A total of 14 fractions were collected and checked by thin layer chromatography for sugar content eluting with isopropanol: water: acetic acid (2:0.5:0.5) solution. The plate was sprayed with sulphuric acid (5%) and heated at 105° C. The fractions eluting first and without sugars were mixed and dried under vacuum conditions and then submitted to a purification step using the same eluting conditions described above until the desired purity was detected by HPLC.

An aliquot of the fractions was diluted and filtered through 0.45 μm using a Nylon membrane filter (Acrodisc, Pall) prior to analysis by HPLC using the method of Example 6.

The selection criteria for a the desired purity of blue polymer from Jagua extract used UV-vis and HPLC standards, i.e., the fractions of the Sephadex column was free of sugar under TLC method, and the absorbance of the main peak detected at 590 nm was equal to or greater than the absorbance at 240 nm, respectively.

Figure 13C:
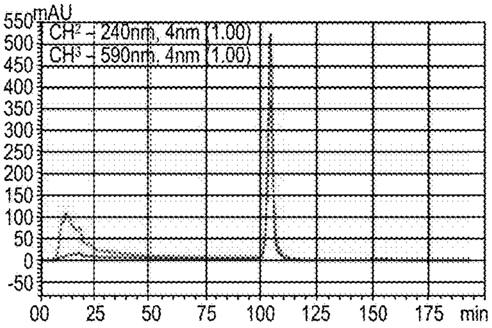
Figure 13D:
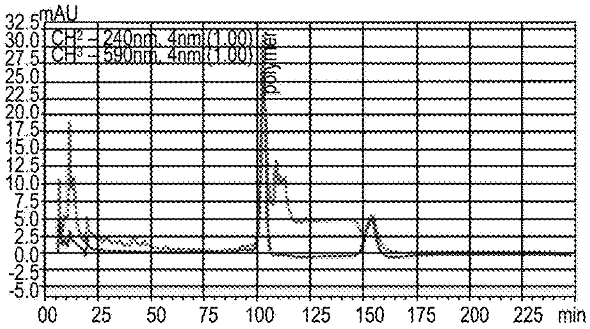
Figure 14A:
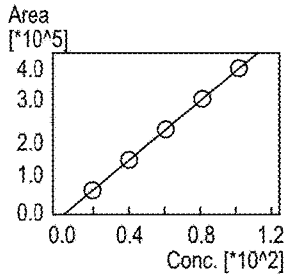
FIGS. 14A-F show calibration curves 1-6, respectively, for blue polymer reference standard solutions.
Figure 14B:
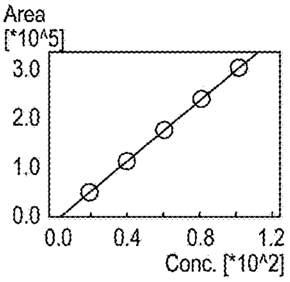
Figure 14C:
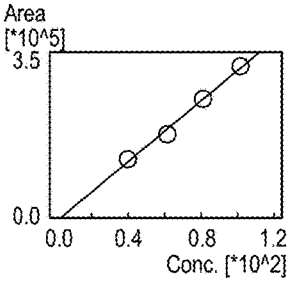
Figure 14D:
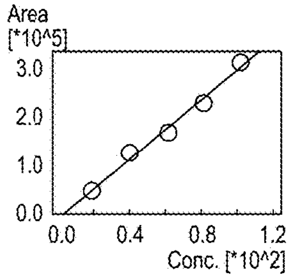
Figure 14E:
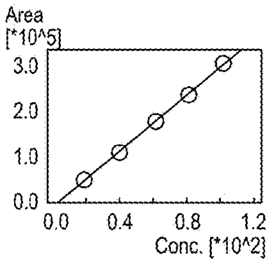
Figure 14F:
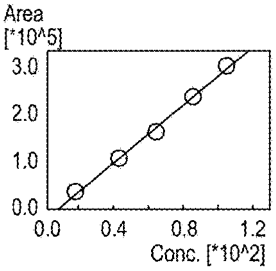

FIGS. 13A-D show HPLC traces (spectra) of the raw batch and three fractions with different purity. FIG. 13C represents a HPLC trace of pure blue polymer (used as a "reference standard") free of sugars.

Example 8. Quantification of Blue Polymer Content in Jagua Extract Samples

Reference standard blue polymer free of sugars prepared in Example 7 was used as an external standard for quantifying the blue polymer content in Jagua Extract samples using the analytical method described in Example 6.

Calibration Curves

Reference standard solutions were prepared from the blue polymer reference standard. Each area under the curve (AUC) from the reference standard was plotted versus concentration and linear regression was applied to obtain the calibration curve equation.

The reference standard solutions were injected in triplicate for five concentrations and in some cases more injections were done.

The method was found to be linear in the range of 20-100 μg/mL.

Six different calibration curves were obtained. Calibration curves 1-6 are shown in FIGS. 14A-F, respectively.

Limits of Detection and Quantification

The method developed to measure blue polymer concentration in Jagua extract was able to detect signals at 10.2 min monitored at 590 nm at a lower limit concentration of 2 μg/mL. According to the formula 2H/h, where H is the Height of the standard reference peak and h is the height at the retention time in a blank chromatogram (10 μL of methanol or water was injected). The value (2×3423/2836=2.4) is the lower limit to be accepted as limit of detection. Mean values of standard reference peak height and blank chromatograms were used for calculations.

The limit of quantification for blue polymer was determined to be 20 μg/mL.

Quantification of Blue Polymers in Jagua Extract Samples

Blue polymer from Jagua Extract was quantified as percentage using the external standard method.

Each batch was weighed in triplicate to get three independent measurements of the dilution at 10 mL in two days; the dilution at 25 mL was performed in triplicate for only one day. For the batch 5312005 only the 10 mL dilution was analyzed, since the purpose of the two volumes of the sample dilution was to evaluate if the concentration was a parameter to take into account when Jagua Extract is analyzed. In Table 1, results from batches 5312001 to 5312004 are shown for the 25 and 10 mL dilutions where mean values can be compared.

The following formula was used to calculate blue polymer concentration when the sample is diluted to 10 mL:

$$\% = \frac{y-b}{a} \times \frac{10}{1000} \times \frac{100}{w}, \text{ or}$$

$$\% = \frac{y-b}{a} \times \frac{25}{1000} \times \frac{100}{w},$$

when sample is diluted to 25 mL; y=assay peak area of blue polymer at 590 nm; b=intercept of the regression line; a=slope of the regression line; w=weight (mg) of the sample.

The percentages in the samples were calculated for each calibration curve generated. Data from calibration curve 1 was excluded. When data from the six calibration curve equations were obtained for each batch analyzed, results from calibration curve 1 were different from other values, and if they were averaged the % RSD increase, probably by errors in the dilution and sample preparation or in the weighing step.

TABLE 1

Percentage of blue polymer in Jagua Extract.

| Batch | Dilution Volume (mL) | Average % (n = 5) | SD | % RSD |
|---|---|---|---|---|
| 5312001 | 10 | 27.88 | 1.48 | 5.32 |
| | 25 | 29.44 | 1.65 | 5.61 |
| 5312002 | 10 | 31.59 | 2.22 | 7.04 |
| | 25 | 31.24 | 1.90 | 6.08 |
| 5312003 | 10 | 31.00 | 2.67 | 8.63 |
| | 25 | 30.93 | 1.85 | 5.98 |
| 5312004 | 10 | 24.43 | 1.54 | 6.34 |
| | 25 | 22.97 | 1.19 | 5.20 |
| 5312005 | 10 | 32.29 | 2.32 | 7.19 |

Example 9. Sugar Removal by Fermentation

Jagua Extract (4.5 L, obtained from the reaction of *Genipa americana* juice and Glycine, Batch 5113003) was sterilized in a vertical autoclave Tuttnauer 3870 ELV (85 liters) (Tuttnauer Europe BV, Netherlands) at 121° C., 15 psi for 20 min. The sterilized Jagua Extract was then allowed to cool inside the autoclave. The resulting broth was inoculated with 25 g of yeast (*Saccharomyces cerevisiae*) commercial grade (Levapan, Colombia), which were previously activated in the same sterile broth at 30° C. Fermentation was carried out in a 7 L bioreactor with 5 L working volume.

The mixture was incubated for 24 hours in the bioreactor BioFlo 110 (New Brunswick Scientific, USA), using the software Biocommand 6.1.7601 Batch Control variables for monitoring. Four samples of 500 mL were tested (every 3 hours for the first 12 hours of incubation). After which, the operating volume was about 2.5 L of broth.

Operating conditions for the fermentation process are shown in Table 2. The system began in anaerobiosis and no external oxygen was added during the fermentation process. The detected percent of oxygen ($DO_2$ (%)) shows the oxygen present in the sample without addition of external oxygen. During the fermentation process, the temperature was kept constant at 30±2° C.

TABLE 2

Bioreactor operating conditions

| Time (HH:MM:SS) | Agitation (rpm) | $DO_2$ (%) | pH | Temperature (° C.) |
|---|---|---|---|---|
| 0:01:06 | 149.80 | 11.55 | 5.61 | 32.59 |
| 23:19:07 | 150 | 9.13 | 5.53 | 29.99 |

After 23 hours 19 minutes, the fermentation process was terminated. The reaction mixture was cooled and subject to centrifuging in Labofuge Thermo Scientific at 200-4800 rpm for 20 minutes (Thermo Fisher Scientific, NJ, USA). Yeast was subsequently removed.

The centrifuged samples were analyzed for soluble solids (° Brix) using a digital refractometer Atago PAL-3 (Atago Co. Ltd. Tokyo, Japan) and for moisture content using MA35M Brand Sartorius (The Sartorius Group, Goettingen, Germany). Sugar content of the samples was analyzed by TLC method with aluminum plates coated with Silica Gel 60 F254 4×5 cm, eluting with a mixture of isopropanol: acetic acid: water (2:0.5:0.5). The TLC plates were sprayed with 10% sulfuric acid in ethanol and heated to 110° C. Pure glucose, fructose and sucrose were used as standards. Analysis of reaction mixtures at 3, 6, 9, and 12 hours showed that 6 hours of fermentation was sufficient to remove all sugars. No sugar was observed by the TLC method described above in the reaction mixture after 6 hours of fermentation.

Example 10. Comparison of Characteristics of Fermented Products and Non-Fermented Products Sample Preparation The fermented Jagua Extract prepared in Example 9 (centrifuged and filtered) were concentrated in a rotary evaporator, and then spray dried with Büchi B-290 (BÜCHI Labortechnik AG, Flawil, Switzerland), with or without carrier vehicle (modified food starch (Capsul®)). The drying conditions were: 150° C. inlet temperature and 103-110° C. outlet temperature; pumping 25% (290 mL/h), air dry flow rate 400 and aspirator 85%.

Non-fermented Jagua Extract (from the same batch used for preparation of the fermented products) was dried under the same conditions as described herein for the fermented products.

In sum, three products were prepared:

(1) PF: a fermented product, centrifuged and concentrated, without vehicle;

(2) FC: a fermented product, centrifuged and concentrated, with vehicle (Capsul®) as a vehicle (60% total solids from product—40% total solids from vehicle);

(3) PC: a non-fermented product, with vehicle (Capsul®) (60% total solids from product −40% total solids from vehicle).

The characteristics of the three powder products (PF, FC, and PC) were analyzed for moisture content, polymer content, color intensity, and stability in a buffer solution at pH 3. Microbiological stability of the products will also be tested.

Polymer Content

Figure 15:
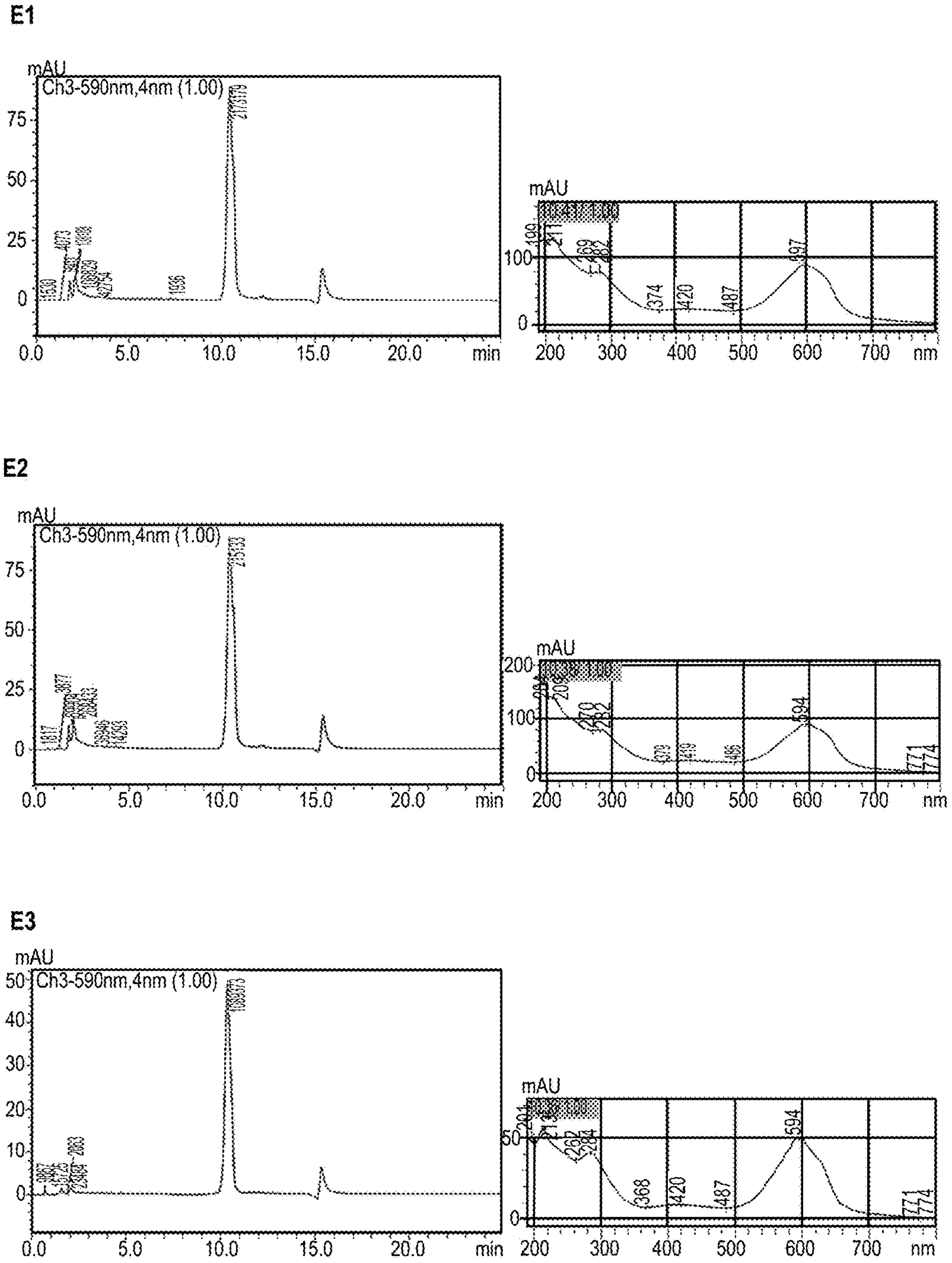
FIG. 15 shows HPLC spectra and UV absorptions of samples PF, FC, and PC (See Example 10 for definition of PF, FC, and PC).

The polymer content of PF, FC, and PC was measured by a HPLC method as described in Examples 6-8. The HPLC results were shown in Table 3. The HPLC chromatograms are shown in FIG. 15.

TABLE 3

| Quantification results of the polymer | | | | | |
|---|---|---|---|---|---|
| Sample | Weight | AUC | % Polymer | Mean | Deviation |
| E1- PFR1 | 10 | 2173179 | 74.36 | 74.01 | 0.38 |
| E1- PFR2 | 10 | 2164260 | 74.06 | | |
| E1- PFR3 | 10 | 2151113 | 73.61 | | |
| E2- FCR1 | 10.2 | 1280814 | 43.16 | 42.26 | 0.81 |
| E2- FCR2 | 10.2 | 1247237 | 42.04 | | |
| E2- FCR3 | 10.2 | 1233766 | 41.59 | | |
| E3- PCR1 | 10 | 1089373 | 37.51 | 37.09 | 0.39 |
| E3- PCR1 | 10 | 1074862 | 37.02 | | |
| E3- PCR1 | 10 | 1066861 | 36.75 | | |

Color Intensity

Color Parameters

Figure 16:
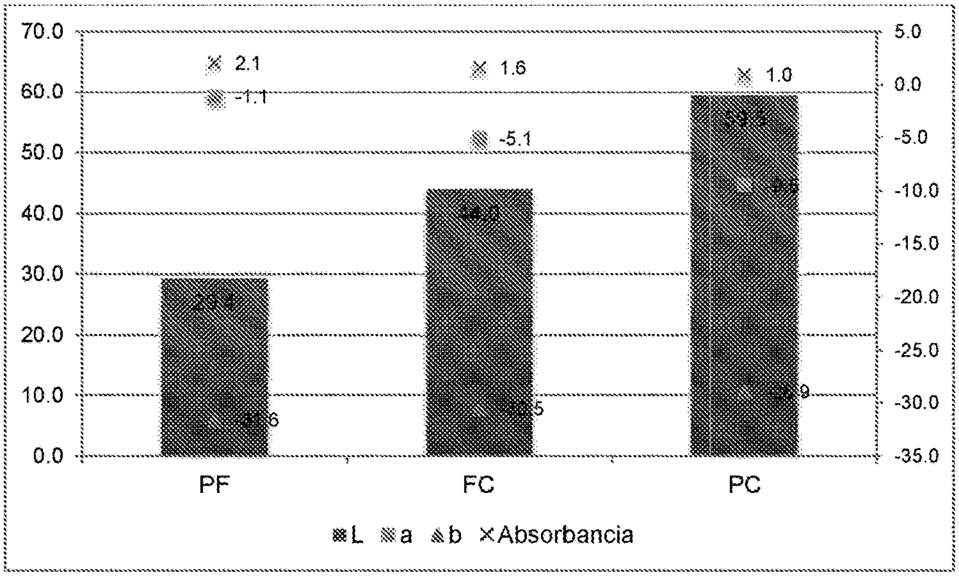
FIG. 16 shows color parameters of samples PF, FC, and PC.

Aqueous dye solutions (0.015 g powder/40 mL) of PF, FC, and PC were analyzed in triplicates with GENESYS 10S UV-VIS spectrometer with VISIONlite software for CIELab parameters. The color parameters of the three samples are shown in FIG. 16.

The CIELab parameters showed that the fermented products (PF and FC) had a blue color that was more intense than the unfermented product. Both PF and FC had lower L values (less brightness), less negative a values (which could mean a more violet color), but similar b values compared to PC. FIG. 16 also shows that PF had the strongest absorbance, twice that of PC; and FC had an absorbance 1.6 times stronger than that of PC.

Stability of Products in a Buffer Solution at pH 3

The stability of PF, FC, and PC was evaluated in a buffer solution at pH 3.0 under three storage conditions: refrigerator (6° C.), temperature (20° C.), and chamber (45° C.) for 19 days.

The products (PF, FC, and PC) were each tested in triplicate at a concentration of 15 mg of sample in 40 mL of buffer. The samples were monitored in the same spectrophotometer from 350 to 800 nm (measured in 2 nm steps). Color changes were determined by CIELab parameters using VISIONlite software version 2 with $D_{65}$ and an observation angle of 10°. Color changes were calculated using equation [1] (shown below) using the parameters L (light, white 0/black 100), a (−green/red+), and b (−blue/yellow+).

$$\Delta E_{ab} = \sqrt{(Li-Lo)^2+(ai-ao)^2+(bi-bo)^2} \quad [1]$$

The color-related parameters, A (absorbance), L, a, b, and $\Delta E_{ab}$ of PF, FC, and PC were monitored over time.

Half-life was calculated according to first order kinetics from the reaction rate constant (slope obtained from plot of Ln (blue area)$_t$/(blue area)$_0$ vs time). Statistical analysis was performed using Statgraphics Centurion XV trial. Fisher least significant difference (LSD) was used to discriminate among the means.

Table 4 shows the results of half-life in days for PF, FC, and PC.

TABLE 4

| Average Half-Life in days | | | | | |
|---|---|---|---|---|---|
| | | Method: 95.0 percent LSD | | | |
| Condition | P-Valor | Sample | Replica | Media | |
| Chamber (45° C.) | 0.0002 | PF | 3 | 25.4233 | X |
| | | FC | 3 | 25.7067 | X |
| | | PC | 3 | 29.7767 | X |
| Ambient (20° C.) | 0.0122 | FC | 3 | 63.5767 | X |
| | | PF | 3 | 66.6967 | X |
| | | PC | 3 | 95.8833 | X |
| Refrigerator (6° C.) | 0.0004 | FC | 3 | 121.697 | X |
| | | PF | 3 | 146.747 | X |
| | | PC | 3 | 169.267 | X |

The moisture content for PF, FC, and PC, as determined by a moisture analyzer (Sartorius Brand MA35M), was 4.12%, 3.24%, and 3.15%, respectively.

The fermentation process efficiently removed all sugars from Jagua extracts within six hours. The resulting fermented products (PF and PC) had a more intense blue color. PF had a blue color twice intense as that of the non-fermented product PC.

The fermented product PF was stable when spray dried without the addition of a vehicle encapsulant (e.g., starch).

The microbiological stability of the fermented products will be tested by adding a known quantity of a microorganism (e.g., a bacteria, fungus, or yeast) to the fermented products and then (e.g., after 7 days) measuring microbiological stability of the fermented products (e.g., by measuring activity of the added microorganism).

Example 11. Removal of Sugar from Jagua Extract by XAD-7

Figure 17:
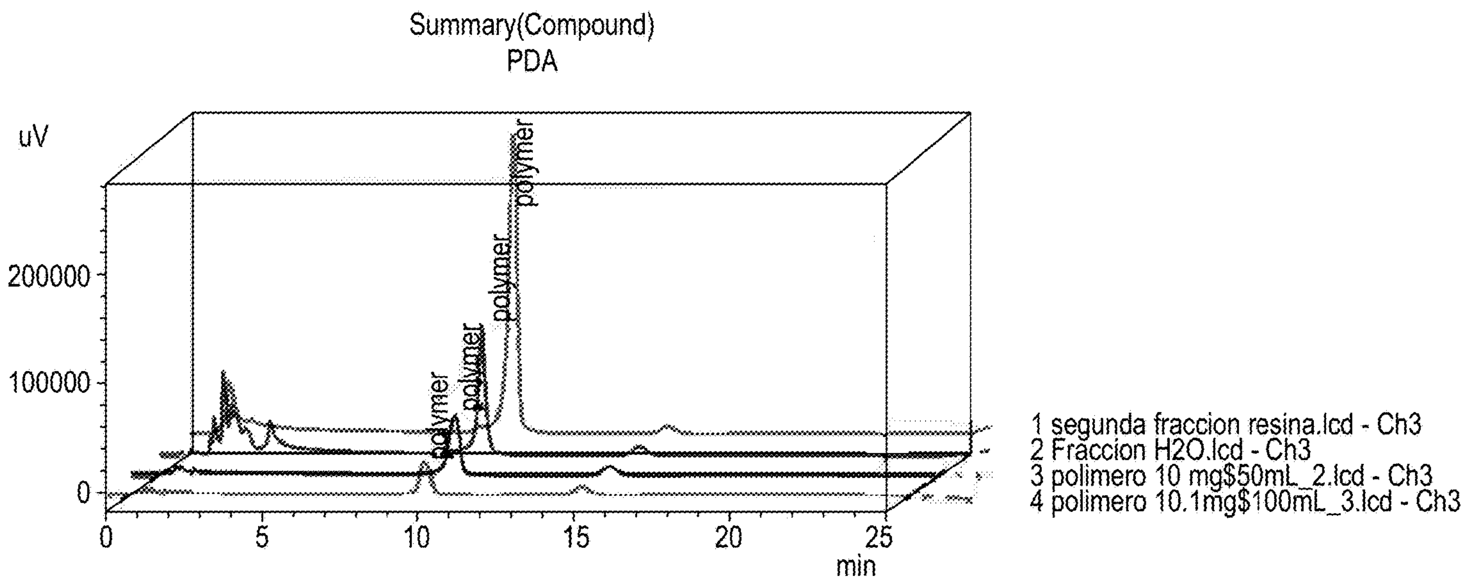
FIG. 17 shows the HPLC spectra of the polymer fraction and the aqueous fraction eluted from XAD-7 resin.

Crude *Genipa americana* juice (150 mL) was reacted with glycine (1.5 g) for 2 hours at 70° C. The reaction mixture was the allowed to cool to room temperature. XAD-7 resin (100 g) were then added to the cooled reaction mixture. After 24 hours, the XAD-7 resin were filtered off The resulting resin were first eluted with water to generate an aqueous fraction and then eluted with a mixture of water and ethanol to generate a polymer fraction. The identity of the polymer in the polymer fraction was confirmed by HPLC analysis using a method of Example 6. Sugar content of the polymer fraction was determined by the TLC method described in Example 9. Analysis by TLC showed absence of sugars in the polymer fraction. The aqueous fraction, on the other hand, was rich in sugars. HPLC analysis also suggested that the aqueous fraction contained some polymer. FIG. 17 shows the HPLC spectra of the polymer fraction and the aqueous fraction.

Table 5 shows the spectrophotometric characteristics of the fractions obtained by purification with HP XAD7 resin.

TABLE 5

Spectrophotometric characteristics of the fractions obtained by purification with HP XAD7 resin

| Sample | L | a | b | Absorbance 590 nm |
|---|---|---|---|---|
| POL | 6.3 | 6.7 | −27.2 | 9.9999 |
| H₂O | 95 | −0.6 | −2.9 | 0.0768 |
| RN | 93 | −2.8 | −6.2 | 0.1267 |

RN: Reaction of *Genipa americana* juice with glycine.
POL: Polymer Fraction; eluted with ethanol, containing majority of the polymer.
H$_2$O: Aqueous Fraction; eluted with water, rich in sugars

Example 12. Reaction of *Genipa americana* Juice with Different Amino Acids

*Genipa americana* juice was reacted with certain amino acids to determine the resulting color profiles. *Genipa americana* juice (50 mL) in a 100 mL Erlenmeyer flask (2.42% genipin content determined by HPLC on a Shimadzu Prominence UFLC (Japan) coupled to a diode array detector and PDA) was mixed with equimolar amounts of glycine (GLY), valine (VAL), lysine (LYS), proline (PRO), methionine (MET), tyrosine (TYR), or tryptophan (TRP). The resulting juice+amino acid mixtures were stirred for 2 hours at 70° C. The reactions were monitored using thin layer chromatography in aluminum plates coated with silica gel F254 4×5 cm, eluting with a mixture of methanol-water 4:1. The reaction products were analyzed by HPLC by a method described in Example 6. Spectrophotometric characterization of the reaction products was performed on GENESYS 10S Spectrophotometer UV-VIS with VISIONlite software version 2.0. For characterization experiments, samples were prepared by diluting 20 μL of the reaction solution in 5 mL of deionized water, except in the case of reactions with tryptophan and proline, samples were prepared by diluting 100 and 200 μL of reaction solution in 5 mL of deionized water, respectively.

The stability of the reaction products produced was evaluated similar to the method described in Example 10 in a buffer solution at pH 3.0, except that in the current Example the reaction products were also subject to irradiation with an ultraviolet lamp UVGL-58 Handheld UV (Ultra-Violet Products Ltd, Cambridge, UK) at 254 nm for 7.46 hours. The reaction products were tested in triplicate at a concentration of 40 μL of the reaction product per 10 mL of buffer at pH 3.0.

Figure 18:
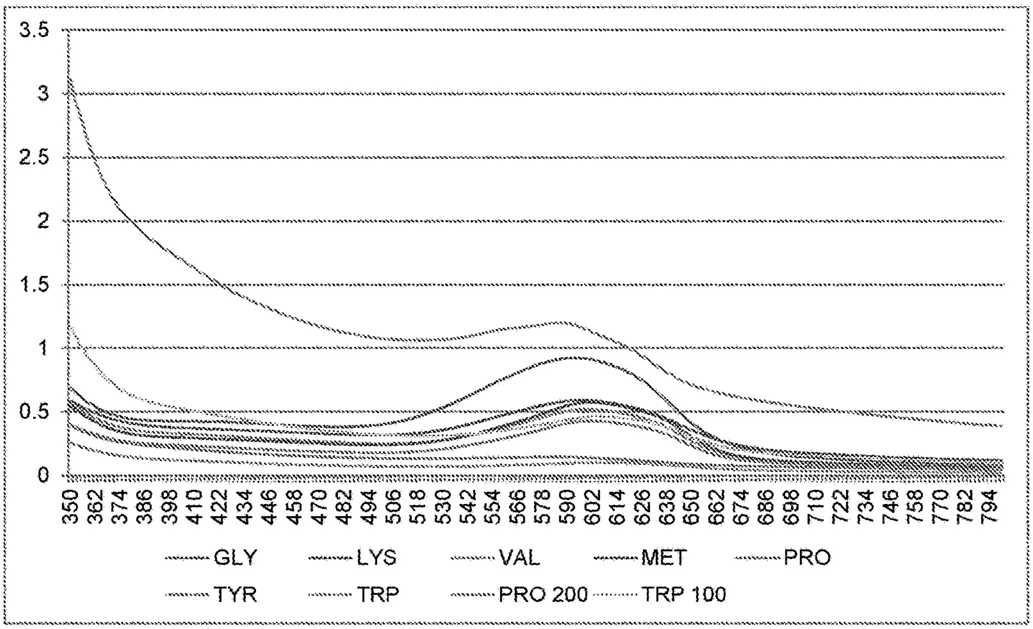
FIG. 18 shows the UV-vis absorption spectra of reaction products of *Genipa americana* juice with different amino acids.

FIG. 18 shows the absorption spectra of reaction products of *Genipa americana* juice with different amino acids. The color parameters of these products are shown in Table 6.

TABLE 6

Color parameters for the reaction products of *Genipa americana* juice with different amino acids

| Amino Acids | L* | a* | b* | $\lambda_{max}$ | Absorbance $\lambda_{max}$ |
|---|---|---|---|---|---|
| GLY | 56.5 | −9.5 | −22.1 | 594 | 0.9217 |
| LYS | 67.6 | −10.4 | −9.7 | 596 | 0.5904 |
| VAL | 72.9 | −12.4 | −7.6 | 598 | 0.5205 |
| MET | 72.3 | −14.7 | −11.1 | 602 | 0.575 |

TABLE 6-continued

Color parameters for the reaction products of *Genipa americana* juice with different amino acids

| Amino Acids | L* | a* | b* | $\lambda_{max}$ | Absorbance $\lambda_{max}$ |
|---|---|---|---|---|---|
| PRO | 88.6 | −0.7 | 3.4 | 350 | 0.3902 |
| TYR | 78.4 | −12.1 | −9 | 602 | 0.4272 |
| TRP | 93.1 | −2.9 | 1.4 | 350 | 0.2582 |
| PRO 200* | 34.2 | 0.9 | 11.1 | 350 | 3.1127 |
| TRP 100* | 72.1 | −10.4 | 4.3 | 350 | 1.1678 |

*For PRO200, 200 microliters of crude reaction mixture were used, whereas in PRO, 20 microliters were used. For TRP100, 100 microliters of crude reaction mixture were used, whereas in TRP, 20 microliters were used.

Figure 19A:
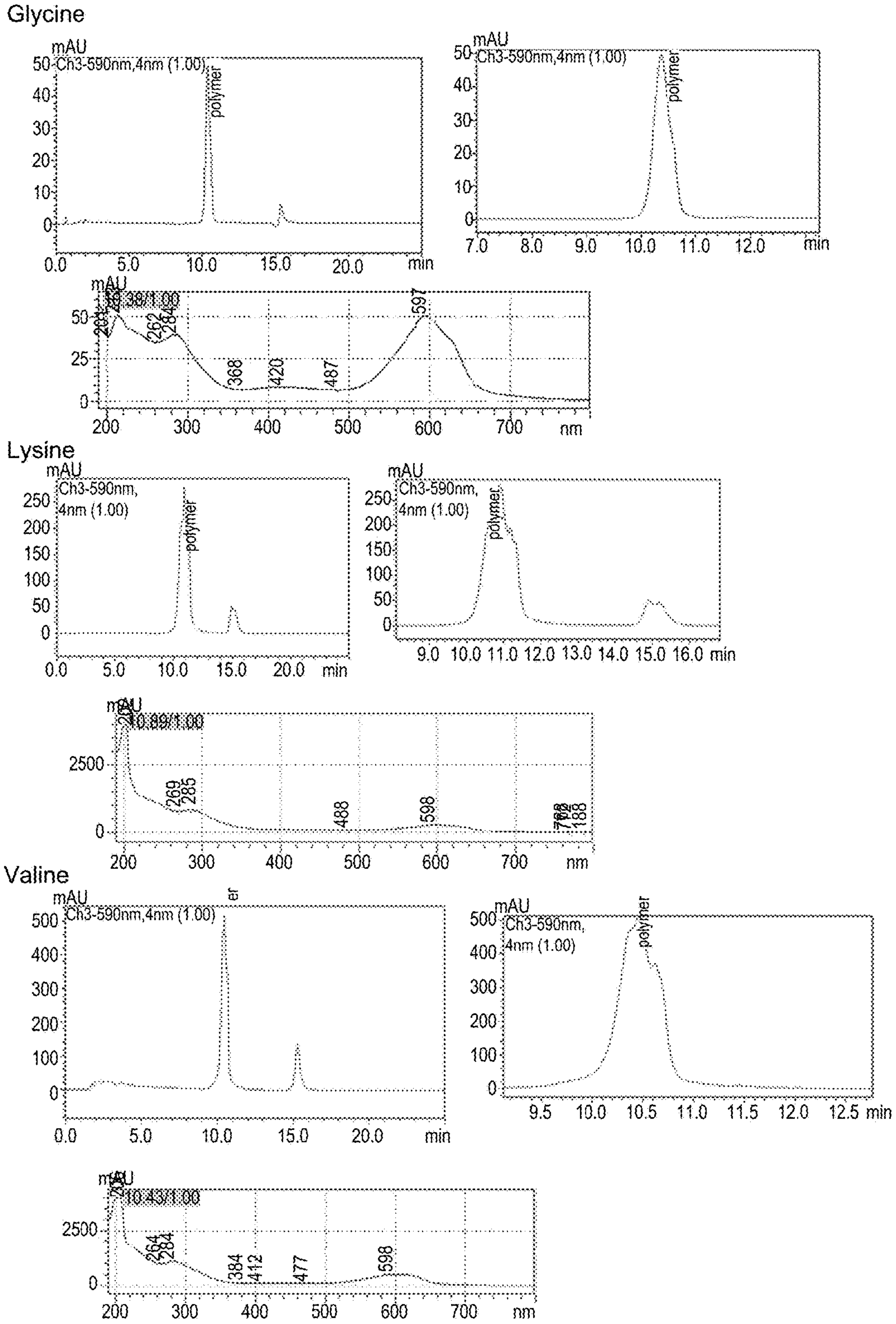
FIGS. 19A-C show HPLC analysis of reaction products of *Genipa americana* juice with different amino acids, categorized according to the amino acids.
Figure 19B:
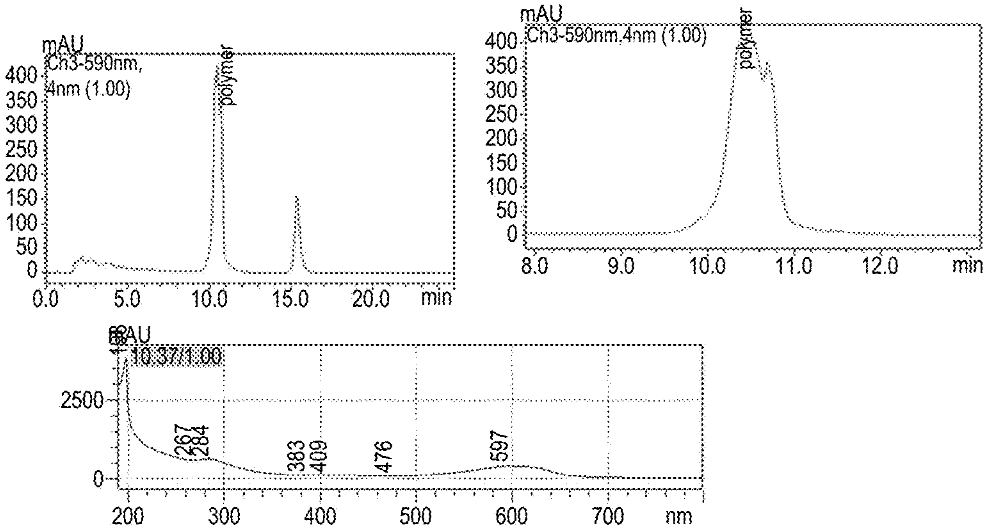
Figure 19B:
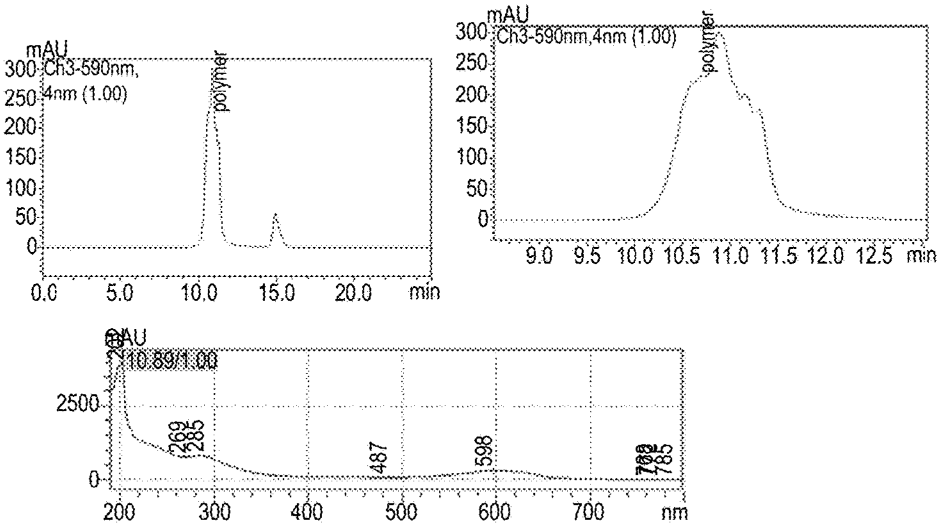
Figure 19C:
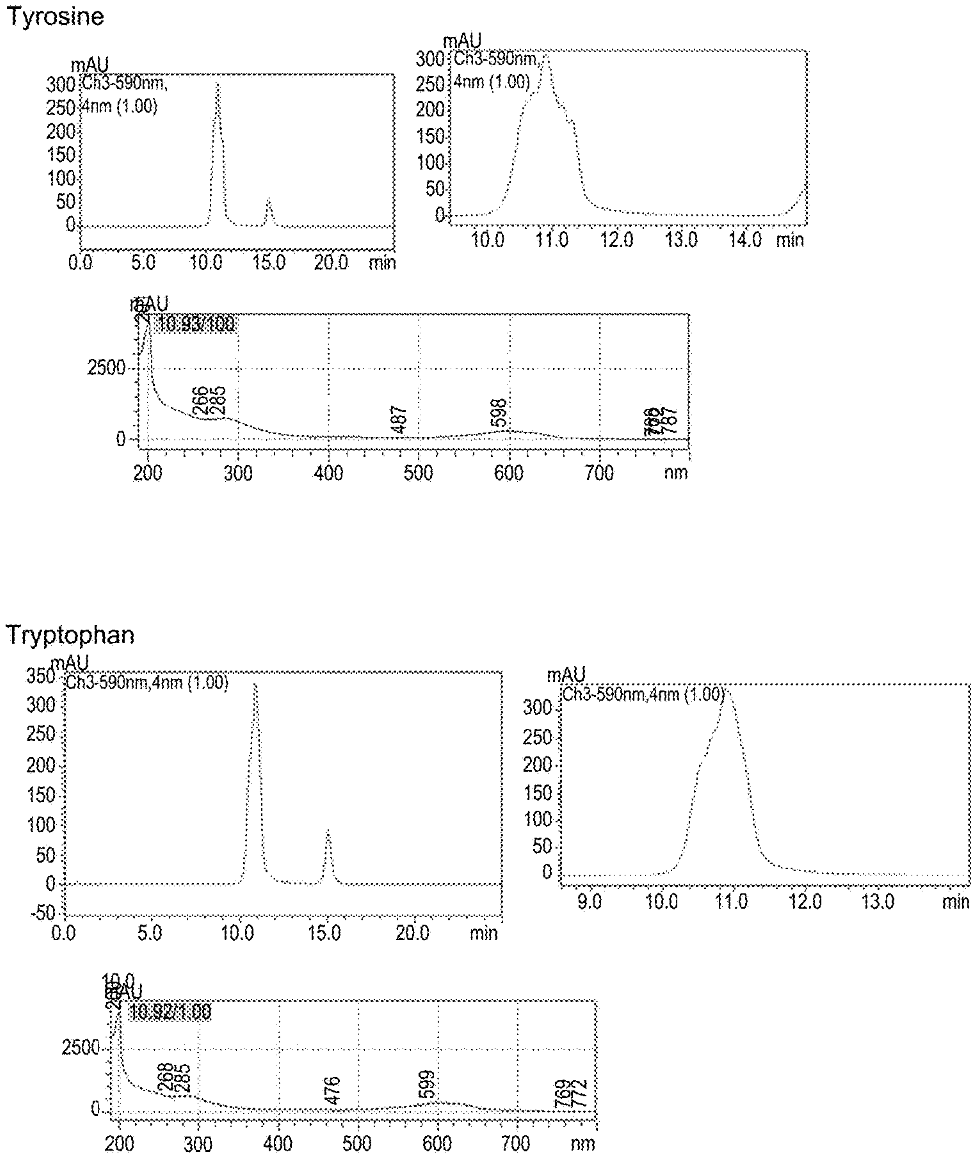

FIGS. 19A-C show HPLC analysis of reaction products of *Genipa americana* juice with different amino acids, categorized according to the amino acids. FIGS. 19A-C show, for each amino acids, HPLC spectra of reaction products of *Genipa americana* juice with the amino acid using a method of Example 6; an enlarged view of HPLC region where a polymer is identified; and UV-vis spectra of selected signal.

The reaction products from amino acids LYS, VAL, MET, and PRO and *Genipa americana* juice have retention times within the range of 10.3 minutes (10.3 minutes±5%). This retention time is similar to the retention time observed for the polymer derived from *Genipa americana* juice and glycine, however, the signals for products of the reaction of *Genipa americana* juice and amino acids LYS, VAL, MET, and PRO were more complex than the signals observed for products of the reaction of *Genipa americana* juice and glycine (see FIGS. 19A-B). Without being bound by theory, these results may indicate the formation of greater number of compounds or polymer chains of different size with the use of amino acids LYS, VAL, MET, and PRO.

The reaction of *Genipa americana* juice and tyrosine or tryptophan did not form products with retention time within the range of 10.3 minutes (i.e., 10.3 minutes±5%). The maximum absorption wavelength ($\lambda_{max}$) for these products was over 600 nm (see FIG. 19C).

Figure 20:
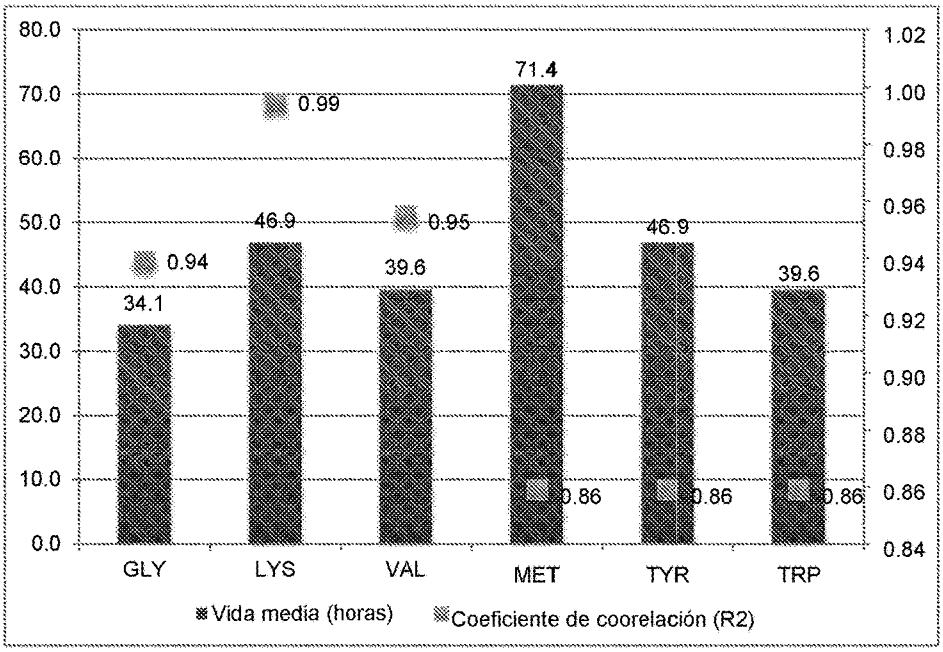
FIG. 20 shows stabilities (expressed in half-lives) of reaction products of different amino acids with *Genipa americana* juice in buffer solution at pH 3.0 with UV irradiation at 254 nm.

FIG. 20 shows stabilities (expressed in half-lives) of reaction products of different amino acids with *Genipa americana* juice in buffer solution at pH 3.0 with UV irradiation at 254 nm.

The reaction of *Genipa americana* juice with different amino acids produced different color products: blue (GLY and LYS), blue green (VAL, MET and TYR), green (TRP) and black (PRO).

The product formed from the reaction of methionine (MET) with *Genipa americana* juice was twice as pH stable as a product derived from glycine (GLY) and *Genipa americana* juice, when tested in buffer solution at pH 3.0 with UV irradiation at 254 nm for 7.46 hours.

HPLC analysis showed that the reaction of *Genipa americana* juice and tyrosine (TYR) or tryptophan (TRP) formed compounds with a slightly lower polarity when compared to the polymer derived from glycine (GLY) and *Genipa americana* juice (as indicated by the higher retention times for the products from reactions with TYR and TRP compared to GLY).

Example 13. Colors Produced from Reaction of Extracts of *Genipa americana* Fruit Mesocarp with Glycine Aqueous Extracts of *Genipa americana* Fruit Mesocarp Aqueous extracts from *Genipa americana* fruit mesocarp (i.e., the peel of the fruit) were prepared. Unripe fruits, which were hard and had skin that was uniform in contrast to ripe fruits, which are soft and have skin that is irregular, were used. Mesocarps of fresh (i.e., within 1-2 days after harvesting) *Genipa americana* fruits (76 g) were liquefied with 300 mL of deionized water. This juice was filtered and analyzed by TLC and HPLC (on a Shimadzu Prominence UFLC coupled to a diode array detector (DAD)) to determine the content of genipin and other iridoid genipin. For comparison, intact fruits of the same age were left at room temperature for three days (non-fresh fruit) before extracting with deionized water as described above. The resulting juice was also analyzed by TLC and HPLC to determine the content of genipin and other iridoid genipin.

Figure 21A:
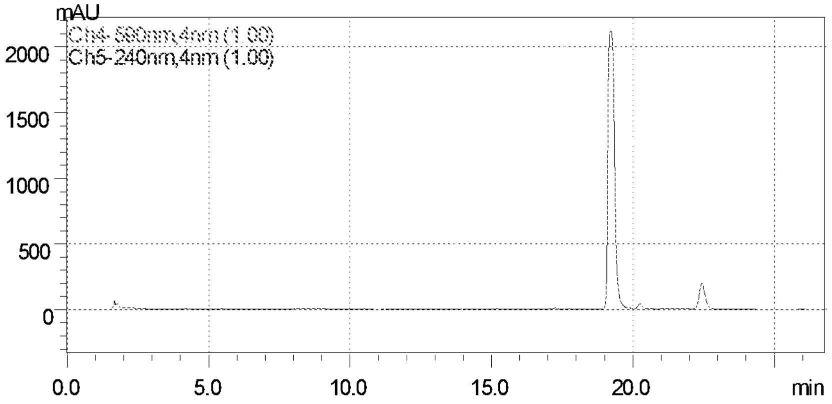
FIG. 21A shows an HPLC spectrum of an aqueous extract of the mesocarps of fresh *Genipa americana* fruits, which has a peak with a retention time of 19 to 20 minutes, near the retention time of genipin (22-23 minutes), with a maximum absorption wavelength at 240 nm.

FIG. 21A shows an HPLC spectrum of an aqueous extract of the mesocarps of fresh *Genipa americana* fruits, which had a peak with a retention time of 19 to 20 minutes, which was near the retention time of genipin (22-23 minutes), with a maximum absorption wavelength at 240 nm.

Figure 21B:
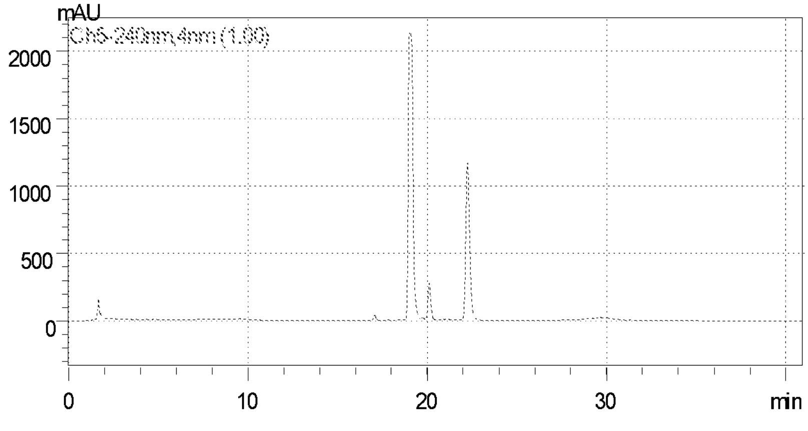
FIG. 21B shows an HPLC spectrum of an aqueous extract of the mesocarps (peels) of *Genipa americana* fruits that are of the same age as in FIG. 21A, but were left at room temperature for three days before extraction. The spectrum has peaks with retention time of 19-20 minutes and 22-23 minutes.

FIG. 21B shows an HPLC spectrum of an aqueous extract of the mesocarps of *Genipa americana* fruits that are of the same age as in FIG. 21A, but were left at room temperature for three days (non-fresh) before extraction. The spectrum had peaks with retention time of 19-20 minutes and 22-23 minutes.

Reaction of Aqueous Extract of Mesocarps (Peel) with Glycine

An aqueous extract of mesocarps (filtered juice, 300 mL) prepared as described above was mixed with glycine (450 mg) in a 500 mL Erlenmeyer flask. Next, the resulting mixture was stirred for 90 minutes at 4000 rpm and 75° C. on a hot plate with magnetic stirring (VELP, Italy). This method produced a product with a deep purple color.

Figure 22:
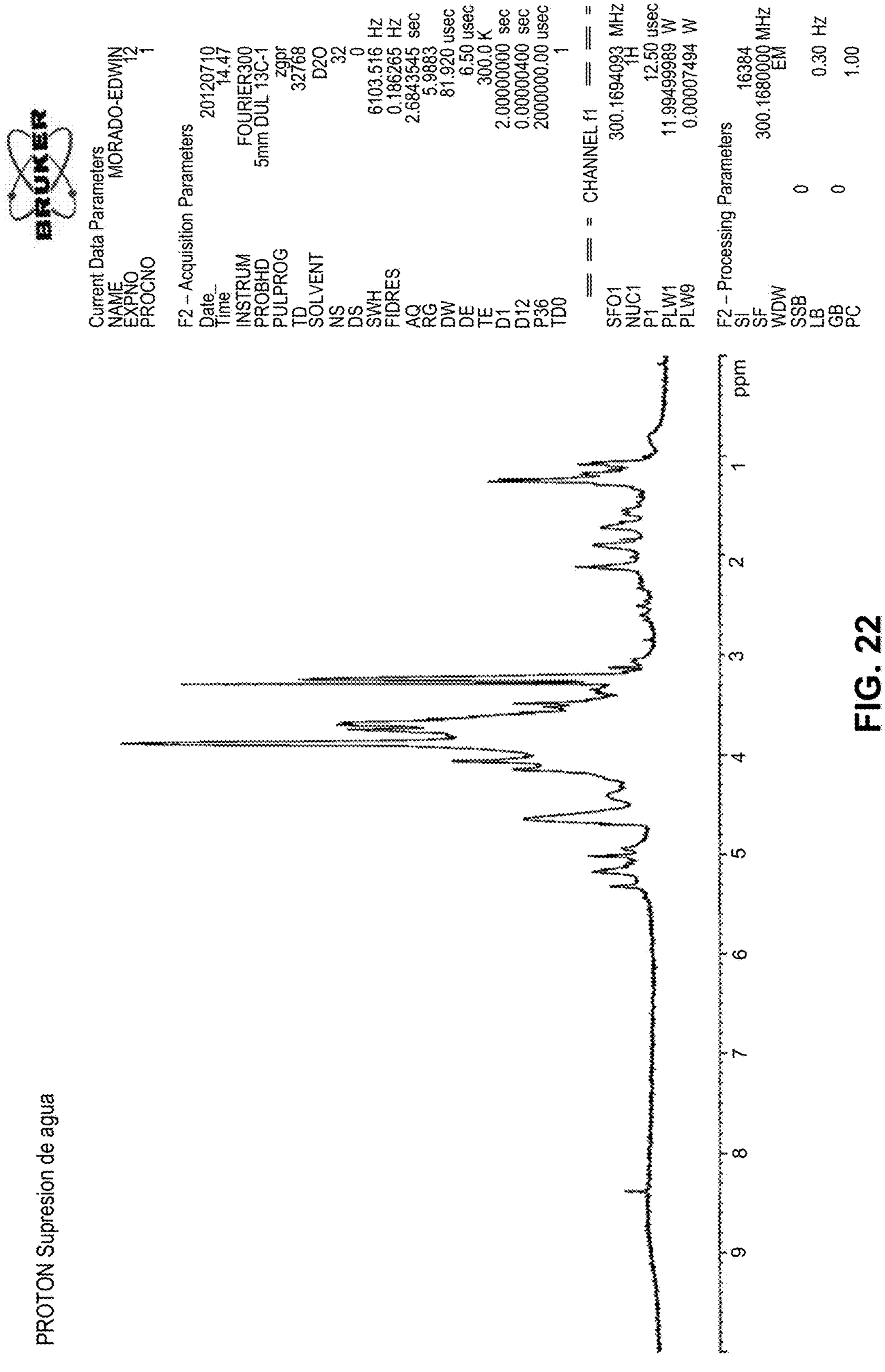
FIG. 22 shows a $^{1}H$ NMR of the purple product obtained from the aqueous extract of *Genipa americana* fruit mesocarps (peels) with glycine.

The reaction product was filtered and characterized with GENESYS 10S brand spectrophotometer UV-VIS with VISIONlite software version 2.0. The crude reaction product was characterized by $^{1}H$ NMR and mass spectrometry (MS). FIG. 22 shows a $^{1}H$ NMR of the purple product obtained from this method of mixing aqueous extract with glycine.

Table 7 shows some signals detected in the purple dye mixture.

TABLE 7

Signals detected in the purple dye mixture analyzed

| | Molecular Mass | Average Mass | | Absolute Abundance |
|---|---|---|---|---|
| A | 15375.9 | 15375.9 | [M + H]+ | 87.09 |
| B | 3619.7 | 3619.7 | [M + H]+ | 72.58 |
| C | 2510.9 | 2510.9 | [M + H]+ | 57.10 |
| D | 10512.7 | 10512.7 | [M + H]+ | 100.00 |
| E | 11100.4 | 11100.4 | [M + H]+ | 60.96 |
| F | 4617.0 | 4617.0 | [M + H]+ | 77.03 |
| G | 6276.6 | 6276.6 | [M + H]+ | 91.86 |
| H | 15503.8 | 15503.8 | [M + H]+ | 61.33 |
| I | 2720.1 | 2720.1 | [M + H]+ | 64.16 |
| J | 8447.5 | 8447.5 | [M + H]+ | 94.78 |

Deconvolution made in Table 7 shows the component signal deconvolution at m/z 257.2.

Figure 23:
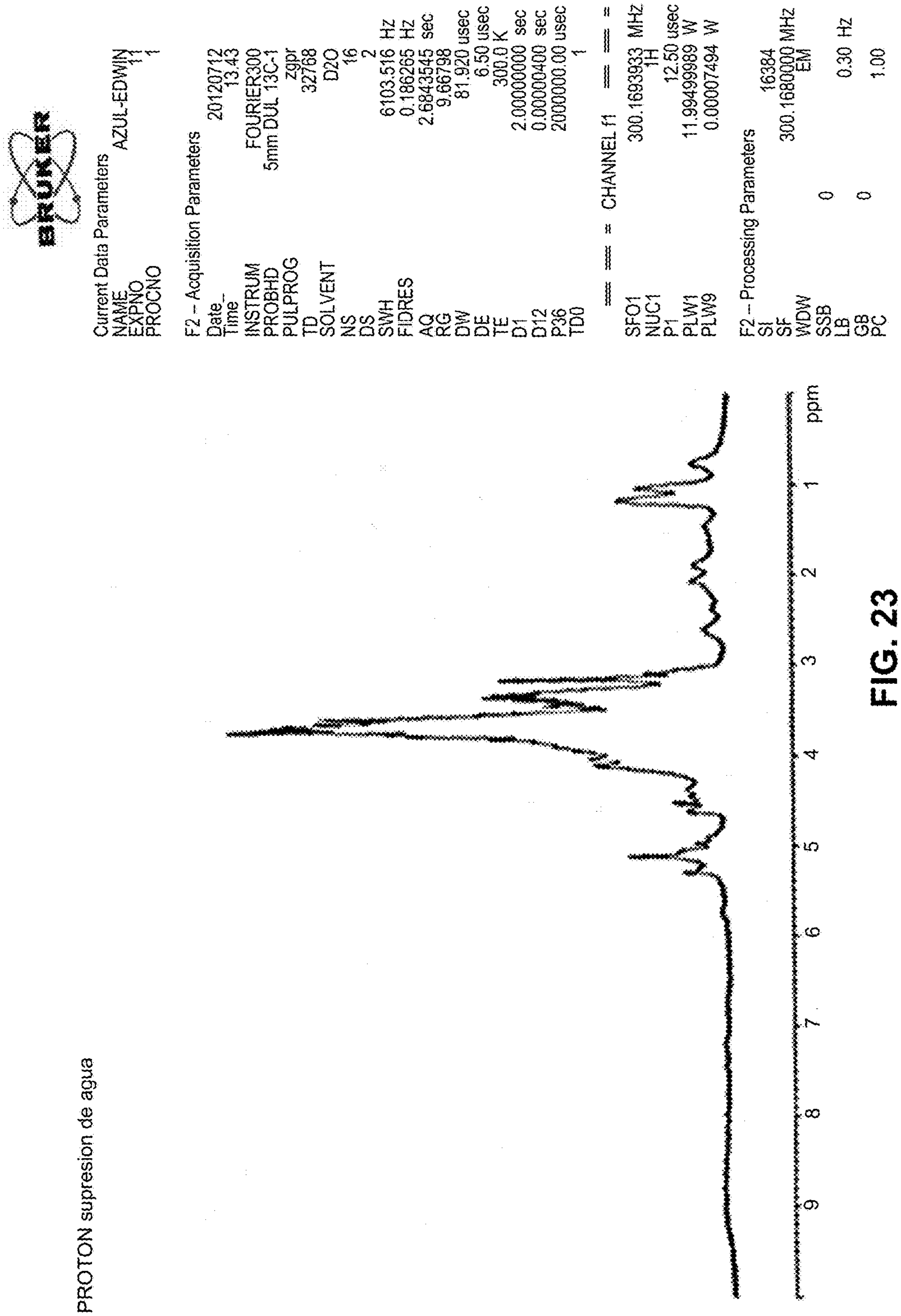
FIG. 23 shows a $^{1}H$ NMR of the blue product obtained from a method of reacting a preheated aqueous extract of *Genipa americana* fruit mesocarps (peels) with glycine.

Alternatively, the method was performed where the aqueous extract was preheated to 70° C. before adding glycine, the product obtained had a blue color. The product was the same blue color as obtained from the mixture of genipin and glycine. FIG. 23 shows a $^{1}H$ NMR of the blue product obtained from this method of mixing the preheated aqueous extract with glycine.

These results show that the reaction product of the juice obtained from *Genipa americana* fruit mesocarps and glycine depended on whether the aqueous extract was preheated before adding glycine. Following the procedure where glycine was mixed with aqueous extract (no preheating), the product formed had a deep purple color. Following the procedure where the aqueous extract was preheated to 70° C. before adding glycine, the product formed had a blue color.

Characterization of Genipin Precursor from the Aqueous Extract of Mesocarps

I. Water Extraction and Freeze Drying Method

Figure 24:
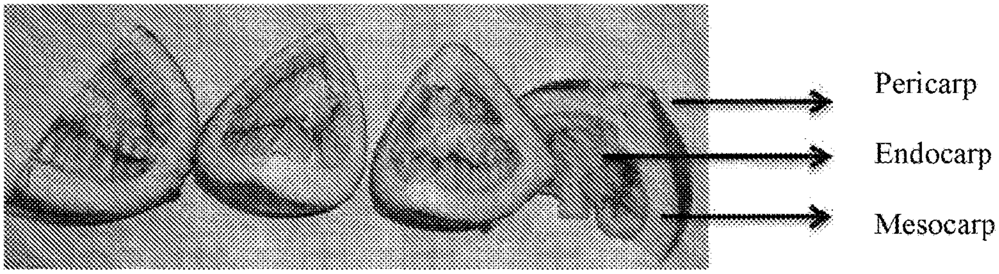
FIG. 24 shows unripe fruits of *Genipa americana* (Jagua) with the pericarp (outer peel), endocarp (pulp) and mesocarp (peel) labeled.

Fresh unripe fruits (two days from harvesting) of *Genipa americana* were cut into four pieces and the mesocarps (peel) were separated from endocarps (pulp) and pericaps (outer peel). An image of the unripe *Genipa americana* is shown in FIG. 24. 360 g of mesocarps were crushed with 300 mL of deionizated water in a blender and the resulting juice was vacuum filtered through cotton, and the juice was immediately freeze dried overnight using a LABCONCO apparatus.

50 mg of the freeze dried product was extracted with 1 mL of $CD_3OD$ under sonication for 5 minutes and filtered. The solution was analyzed by $^{1}H$ and $^{13}C$ NMR at 300 and 75 MHz, respectively, on a Bruker Fourier 300 with water suppression.

II. Liquid Nitrogen Freezing Method

Fresh cut mesocarps were crushed after freezing with liquid nitrogen and 50 mg of the resulting powder was extracted with 1 mL of $CD_3OD$ under sonication for 5 minutes and filtered, the solution was analyzed by $^{1}H$ and $^{13}C$ NMR at 300 and 75 MHz, respectively, on a Bruker Fourier 300 with water suppression.

III. Results

Figure 25A:
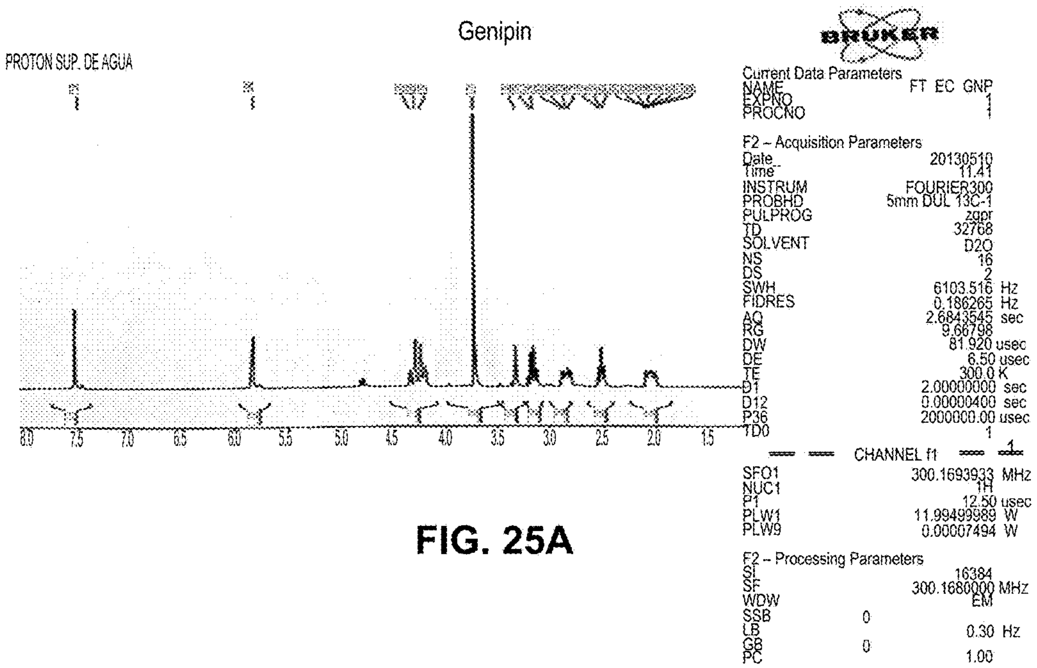
FIG. 25A-B shows $^1$H NMR spectra in $CD_3OD$ (with water suppression) of genipin (25A) and the precursor found in mesocarps (25B).
Figure 25B:
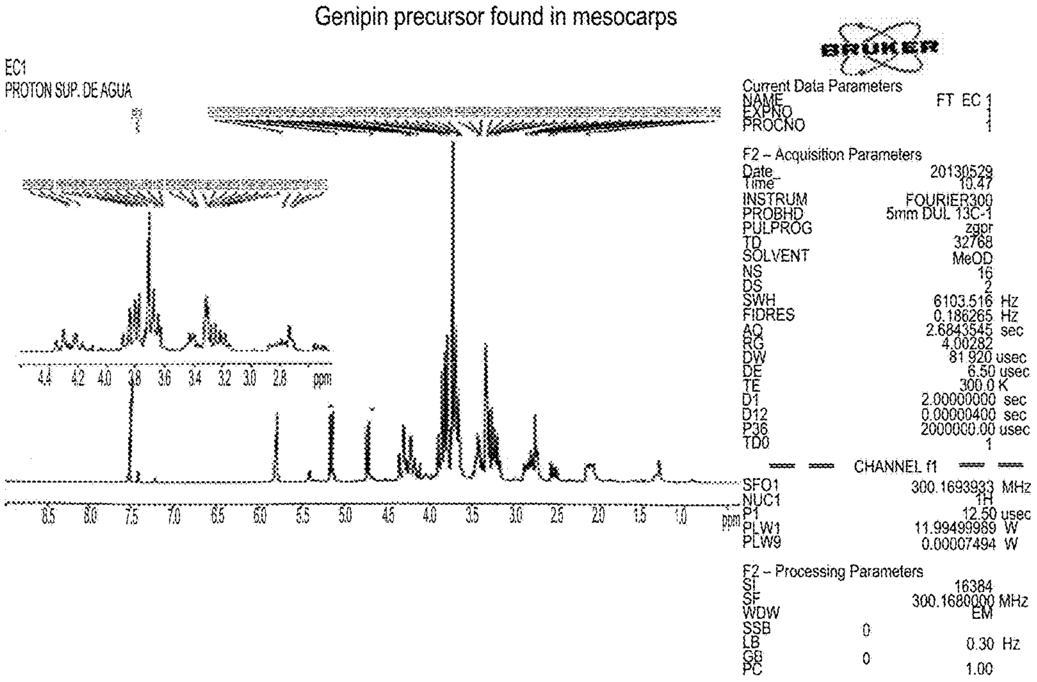

The $^{1}H$ NMR results for freeze dried and nitrogen frozen mesocarps showed a very good resolved spectrum with a similar pattern of genipin fingerprint (FIG. 25A-B).

Figure 26A:
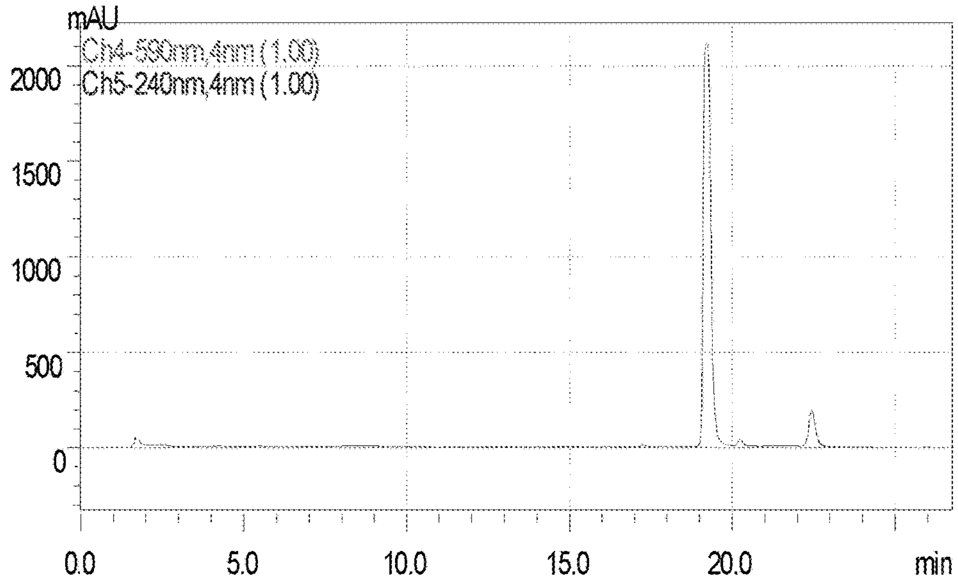
FIG. 26A-B shows HPLC profiles (240 nm) of water mesocarps extract (26A) and ethyl acetate solvent partition of the water extract (26B).
Figure 26B:
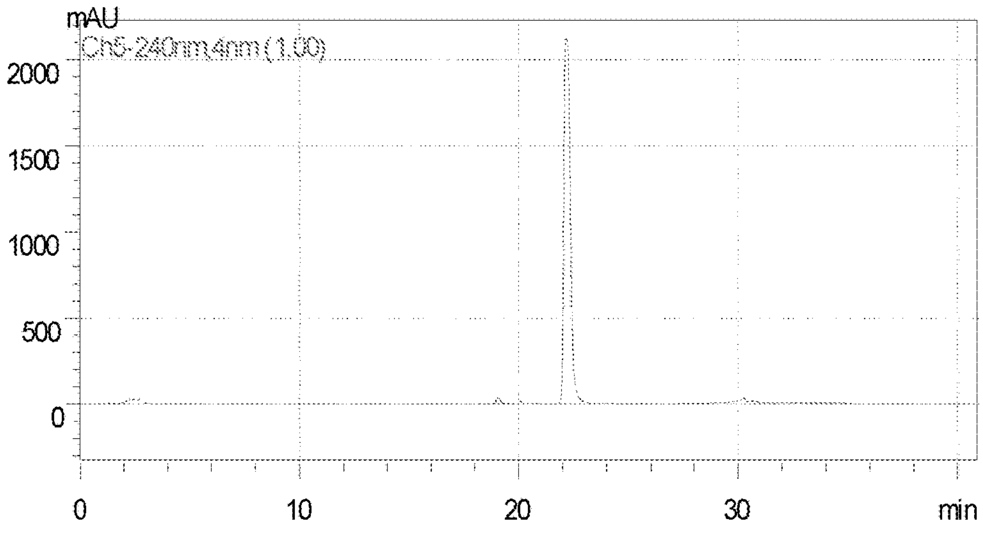

The water extract of Jagua mesocarps had a HPLC (240 nm) peak at 19 minutes that disappeared after heating or extracting with ethyl acetate. The genipin peak 21-22 minutes was be detected. FIG. 26A-B show the HPLC profiles (240 nm) of water mesocarps extract and ethyl acetate solvent partition of the water extract, respectively.

Figure 27:
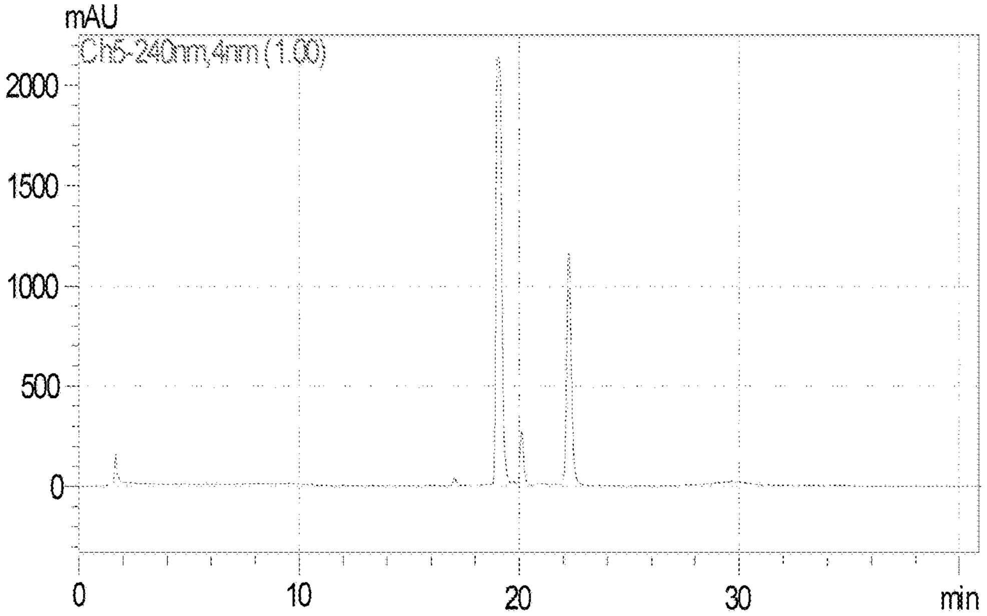
FIG. 27 shows HPLC profile (240 nm) of a water extract mesocarps from Jagua fruits kept at room conditions during several days after harvesting.

The formation of genipin from the precursor in the mesocarp of Jagua fruits was spontaneous as determined by HPLC profiles of water extracts prepared with fruits kept at room conditions during several days after the analysis presented in FIG. 26A. Genipin was seen at 21-22 minutes, and its precursor at 19 minutes could be detected at 240 nm (FIG. 27).

Figure 28:
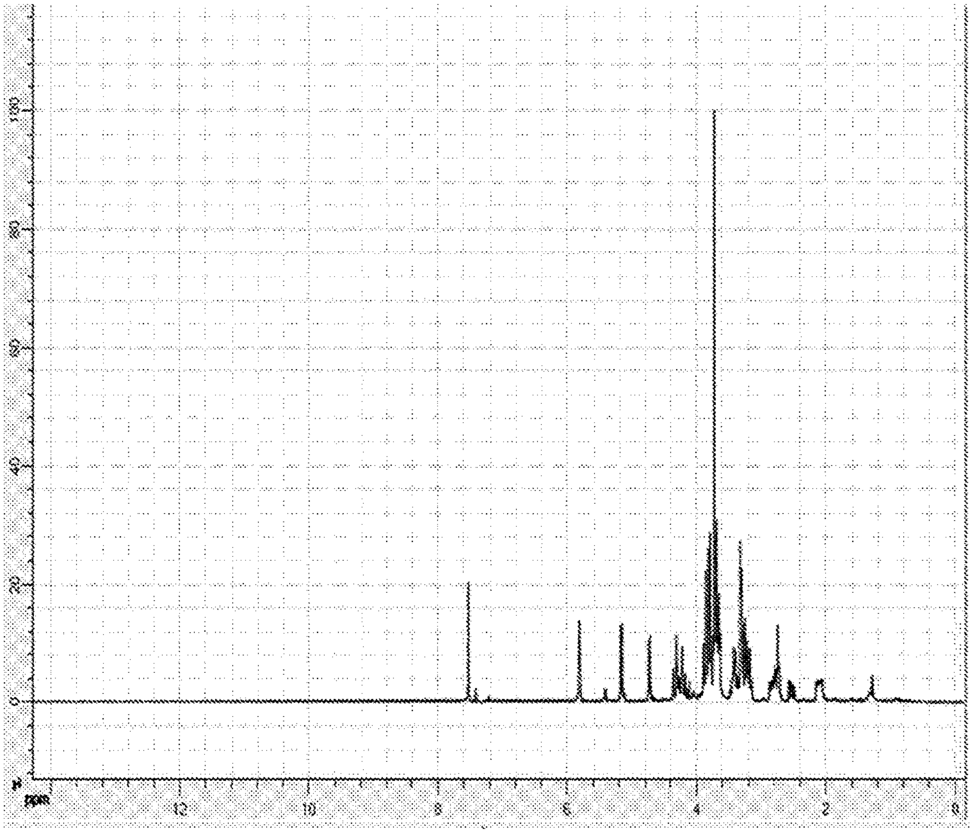
FIG. 28 shows $^1$H NMR experiment for the water extract of the mesocarp, the field was expanded to show the region where aldehyde peaks are expected to be.

The fast and spontaneous formation of genipin from its precursor found in Jagua mesocarps indicated both an structural change (i.e. formation of the hemiacetal ring) of the precursor triggered by oxygen or heat, leading to genipin or an enzymatic cleavage of the precursor molecule to release genipin to the endocarp of the fruit. The $^{1}H$ NMR experiment for the water extract of the mesocarp do not display an aldehyde proton (12 ppm), see FIG. 28.

Figure 29:
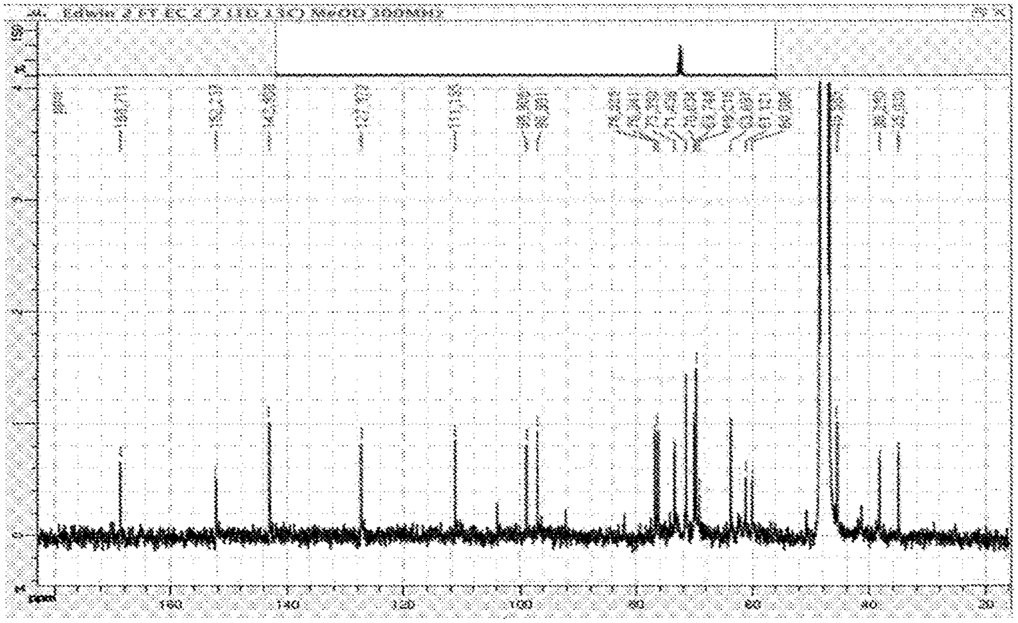
FIG. 29 shows $^{13}$C NMR spectrum for genipin precursor found in Jagua mesocarps.
Figure 30:
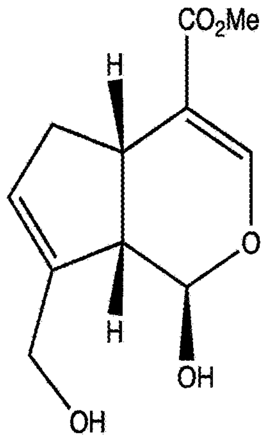
FIG. 30 shows chemical structures of Genipin (1) and geniposide (2)
Figure 30:
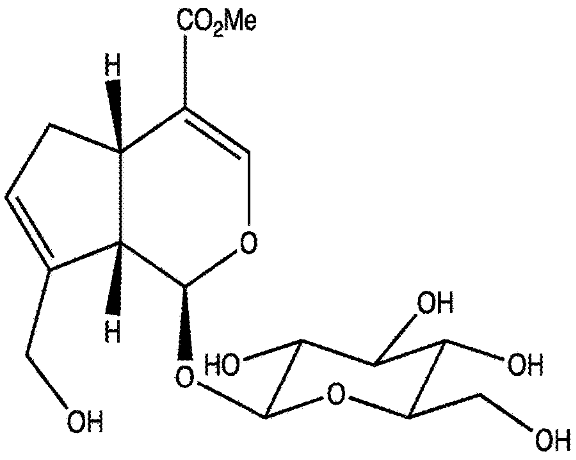

Two doublets at 5.1 and 4.7 ppm and carbon signals at 100 and 70-80 ppm, were detected, which were not present in genipin and are characteristic of anomeric protons and CHO moieties in sugars, supporting that the precursor was a glycoside of genipin. The $^{1}H$ (FIG. 29) and $^{13}C$ (FIG. 30) data for genipin precursor match the molecule (+)-Geniposide and irodoid B-glycoside precursor of genipin.

Spectral Data for (+)-Geniposide:

$^{1}H$ NMR: (300 MHz, $CD_3OD$): δ 7.53 (s, 1H), δ 5.81 (s, 1H), δ 5.17 (d, J=7.6 1H), δ4.73 (d, J=7.8 Hz, 1H), δ4.33 (d, J=14.6 Hz, 1H), δ4.20 (d, J=14.3 Hz, 1H), δ3.83 (d, J=11.7 Hz, 1H), δ3.72 (s, 3H), δ3.66 (dd, j=12.2, 5.7 Hz, 1H),

δ3.39-3.42 (m, 1H), δ3.15-3.28 (m, 3H), δ2.83 (dd, 16.5, 8.4 Hz, 1H), δ 2.53 (dd, J=7.95, 15.75 Hz, 1H), δ2.05-2.14 (m, 1H)

$^{13}C$ NMR: (75 MHz, $CD_3OD$): δ168.71, 152.23, 142.98, 127.37, 111.15, 98.90, 96.99, 76.82, 76.34, 73.39, 71.43, 61.12, 60.00, 50.77, 45.58, 38.29, 35.03.

Example 14. Addition of Methionine and Glycine to *Genipa americana* Juice

*Genipa americana* juice was reacted with methionine and glycine to determine the resulting color profiles. *Genipa americana* juice (50 mL) was added to a mixture of 100 mg methionine and 100 mg of glycine, and the reaction was maintained at 70° C. for 2 hours.

In a second experiment, *Genipa americana* juice (50 mL) was initially added to 100 mg methionine and after one hour of reaction, an additional 100 mg of glycine was added, and the reaction was maintained for another hour.

The color resulting from each of these reactions was measured from aqueous solutions of dyes in powder to 0.015 g/40 mL in GENESYS 10S spectrophotometer UV-vis absorption in the range between 400 and 700 of wavelength to determine the maximum absorbance and the CIELab parameters.

Independent of the order of addition of amino acids the result is the formation of a deep blue color. Thin layer chromatography showed the formation of polymer, and shows that the main compound was the same regardless of the order of addition of reactants and the color was the same whether methionine or glycine alone or a mixtures of methionine and glycine was used. TLC showed blue dye formation. The reaction products were analyzed spectrophotometrically as shown in Table 8.

TABLE 8

CIELab parameters for the reactions between *Genipa americana* juice and mixtures of methionine and glycine and glycine

| Sample | L | a | b | Absorbance 590 nm |
|---|---|---|---|---|
| M + G | 87 | −3.6 | −11.2 | 0.2374 |
| 1 + 2 | 88.1 | −4.2 | −10.5 | 0.221 |
| RN | 93 | −2.8 | −6.2 | 0.1267 |

M + G: Simultaneous Reaction *Genipa americana* juice with glycine and methionine
1 + 2: Reaction of methionine with *Genipa americana* juice followed by glycine.
RN: *Genipa americana* juice reaction with glycine.

Figure 31:
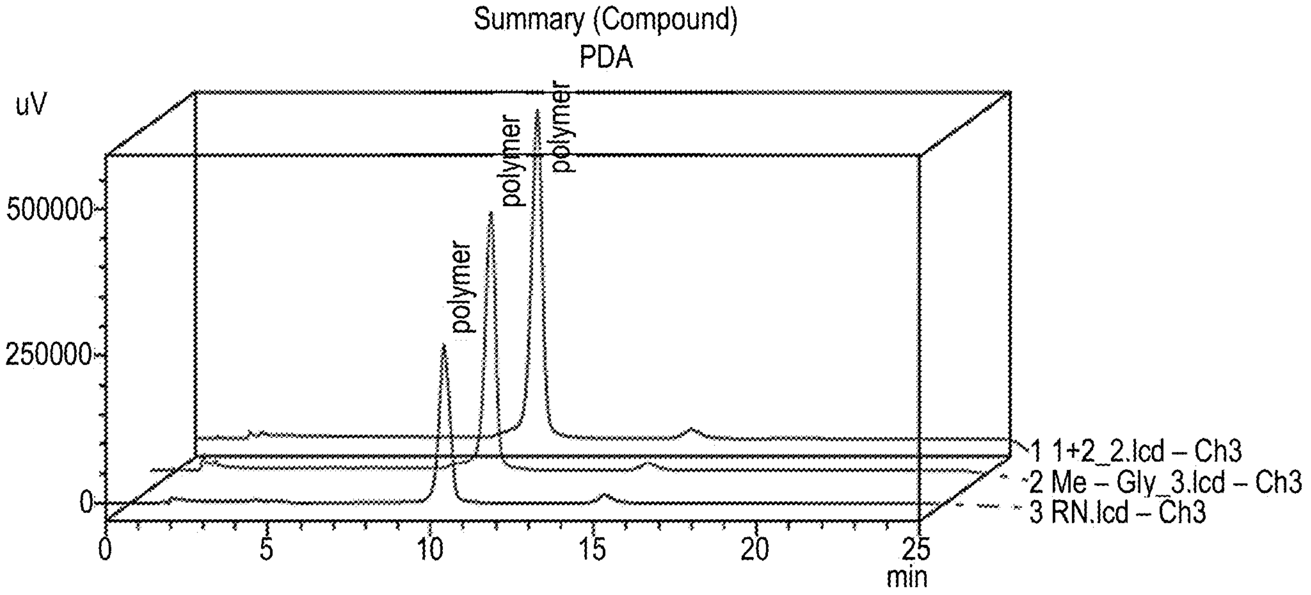
FIG. 31 shows chromatograms obtained by Me-Gly: simultaneous reaction of *Genipa americana* juice with glycine and methionine; 1+2: reaction of methionine with *Genipa americana* juice followed by glycine; and RN: reaction of *Genipa americana* juice with glycine alone.

The retention time in the HPLC chromatogram of the polymer was identified in the majority of the *Genipa americana* juice and amino acid mixture and was the same as the dye produced by the reaction between glycine and *Genipa americana* juice only. The absorption maximum was 590 nm. Glycine and methionine spiked simultaneously *Genipa americana* juice. Chromatograms obtained by reactions between *Genipa americana* juice and the amino acids glycine and methionine as well as glycine alone are shown in FIG. 31.

The invention claimed is:

1. A method of preparing of a black colorant composition comprising
(a) preparing a juice extract from *Genipa americana* fruit, wherein the juice extract is raw liquid *Genipa americana* juice;
(b) mixing the juice extract and proline to form a mixture; and
(c) isolating a black colorant composition from the mixture of (b).

2. A black colorant composition prepared by the method of claim 1.

3. A method of preparing of a green colorant composition comprising
(a) preparing a juice extract from *Genipa americana* fruit, wherein the juice extract is raw liquid *Genipa americana* juice;
(b) mixing the juice extract and tryptophan to form a mixture; and
(c) isolating a green colorant composition from the mixture of (b).

4. A green colorant composition prepared by the method of claim 3.

5. A food product comprising a food item and the black colorant composition of claim 2.

6. The food product of claim 5, wherein the food item is a solid food item or a liquid food item.

7. The food product of claim 6, wherein the food item is a beverage.

8. A food product comprising a food item and the green colorant composition of claim 4.

9. The food product of claim 8, wherein the food item is a solid food item or a liquid food item.

10. The food product of claim 9, wherein the food item is a beverage.

11. A drug or nutraceutical product comprising a drug or nutraceutical and the green colorant composition of claim 4.

12. The drug or nutraceutical product of claim 11, wherein the drug or nutraceutical is in a dosage form selected from the group consisting of tablets, gel caps, beads, pellets, pills, dragees, lozenges, ointments, capsules, powders, liquids, gels, syrups, slurries, and suspensions.

13. A cosmetic product comprising the green colorant composition of claim 4.

14. The method of claim 1, further comprising heating the mixture of juice extract and proline after step (b).

15. The method of claim 3, further comprising heating the mixture of juice extract and tryptophan after step (b).

16. The method of claim 1, further comprising purifying the black colorant composition of (c).

17. The method of claim 3, further comprising purifying the green colorant composition of (c).

18. The method of claim 3, wherein no additional ingredients are added to the raw liquid *Genipa americana* juice prior to step (b).

19. The method of claim 3, wherein the tryptophan is in an isolated form.

20. The method of claim 3, wherein the tryptophan is mixed with the juice extract in an equimolar amount relative to the amount of genepin in the juice extract.

21. The method of claim 1, wherein no additional ingredients are added to the raw liquid *Genipa americana* juice prior to step (b).

22. The method of claim 1, wherein the proline is in an isolated form.

23. The method of claim 1, wherein the proline is mixed with the juice extract in an equimolar amount relative to the amount of genepin in the juice extract.

24. A drug or nutraceutical product comprising a drug or nutraceutical and the black colorant composition of claim 2.

* * * * *

UNITED STATES PATENT AND TRADEMARK OFFICE

CERTIFICATE OF CORRECTION

PATENT NO. : 10,266,698 B2
APPLICATION NO. : 15/807435
DATED : April 23, 2019
INVENTOR(S) : Vargas Cano et al.

It is certified that error appears in the above-identified patent and that said Letters Patent is hereby corrected as shown below:

In the Specification

In Column 2, Line 11, delete “Chem” and insert -- Chem. --, therefor.

In Column 9, Line 66, delete “shows” and insert -- show --, therefor.

In Column 11, Line 15, delete “geniposide (2)” and insert -- geniposide (2). --, therefor.

In Column 16, Line 33, delete “fractions.” and insert -- fractions; --, therefor.

In Column 16, Line 35, delete “fractions.” and insert -- fractions; --, therefor.

In Column 16, Line 51, delete “[M+H]” and insert -- $[M+H]^+$ --, therefor.

In Column 16, Line 62, delete “N-CH2” and insert -- N-$CH_2$ --, therefor.

In Column 17, Line 26, delete “fractions.” and insert -- fractions; --, therefor.

In Column 17, Line 53, delete “fractions.” and insert -- fractions; --, therefor.

In Column 19, Lines 5-15, delete “ 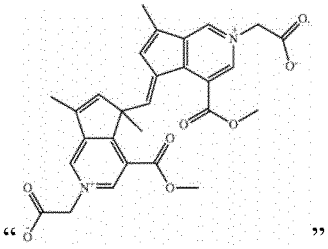 ” and insert

Signed and Sealed this
Fifteenth Day of September, 2020

Andrei Iancu
*Director of the United States Patent and Trademark Office*

--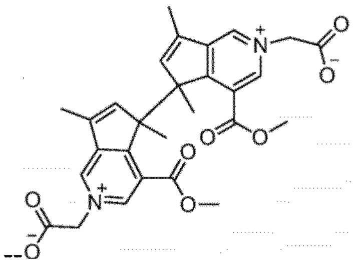 --, therefor.

In Column 28, Lines 40-55, delete "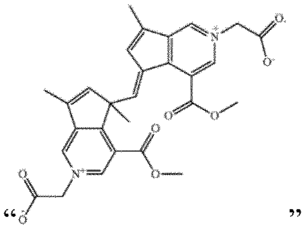" and insert

--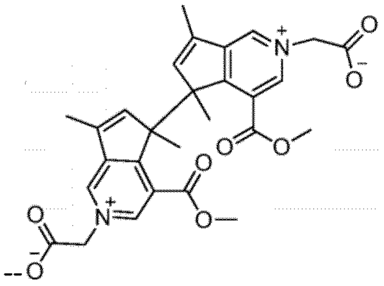 --, therefor.

In Column 31, Line 45, delete "(MO)" and insert -- (MW)) --, therefor.

In Column 39, Line 5, delete "1H – 1H" and insert -- $^{1}H$ – $^{1}H$ --, therefor.

In Column 39, Line 8, delete "13C" and insert -- $^{13}C$ --, therefor.

In Column 39, Line 12, delete "N-CH2" and insert -- N-$CH_2$ --, therefor.

In Column 39, Line 14, delete "[$M^{+}$+H]" and insert -- $[M+H]^{+}$ --, therefor.

In the Claims

In Column 52, Claim 20, Line 54, delete "genepin" and insert -- genipin --, therefor.

In Column 52, Claim 23, Line 62, delete "genepin" and insert -- genipin --, therefor.